(12) United States Patent
Shaolian et al.

(10) Patent No.: US 12,076,241 B2
(45) Date of Patent: Sep. 3, 2024

(54) ADJUSTABLE IMPLANT SYSTEM

(71) Applicant: NuVasive Specialized Orthopedics, Inc., San Diego, CA (US)

(72) Inventors: Samuel Shaolian, Newport Beach, CA (US); Scott Pool, Laguna Hills, CA (US); Ross Tsukashima, San Diego, CA (US); Daniel Anderson, Brea, CA (US)

(73) Assignee: NuVasive Specialized Orthopedics, Inc., San Diego, CA (US)

( * ) Notice: Subject to any disclaimer, the term of this patent is extended or adjusted under 35 U.S.C. 154(b) by 78 days.

(21) Appl. No.: 17/524,133

(22) Filed: Nov. 11, 2021

(65) Prior Publication Data

US 2022/0061989 A1   Mar. 3, 2022

Related U.S. Application Data

(63) Continuation of application No. 16/103,710, filed on Aug. 14, 2018, now Pat. No. 11,202,707, which is a
(Continued)

(51) Int. Cl.
*A61F 2/24*   (2006.01)

(52) U.S. Cl.
CPC .......... *A61F 2/2442* (2013.01); *A61F 2/2448* (2013.01); *A61F 2/2445* (2013.01);
(Continued)

(58) Field of Classification Search
CPC .... A61F 2/2442; A61F 2/2445; A61F 2/2448; A61F 2/24
See application file for complete search history.

(56) References Cited

U.S. PATENT DOCUMENTS

| | | | |
|---|---|---|---|
| 2,702,031 | A | 2/1955 | Wenger |
| 3,111,945 | A | 11/1963 | Solbrig |

(Continued)

FOREIGN PATENT DOCUMENTS

| | | | |
|---|---|---|---|
| CN | 1697630 | A | 11/2005 |
| CN | 101040807 | A | 9/2007 |

(Continued)

OTHER PUBLICATIONS

Abe et al., "Experimental external fixation combined with percutaneous discectomy in the management of scoliosis.", SPINE, 1999, pp. 646-653, 24, No. 7.
(Continued)

*Primary Examiner* — Seema Mathew

(57) ABSTRACT

Systems and methods treat a heart valve using a magnetically adjustable annuloplasty ring attached to or near a cardiac valve annulus. A changing magnetic field may be used to selectively increase or decrease a circumference of, or otherwise modify the shape of, the implanted annuloplasty ring. The adjustable annuloplasty ring includes a tubular body member, one or more adjustable members, and an internal magnet within the tubular body member. The tubular body member and the one or more adjustable members form a ring shape. The internal magnet is configured to rotate in response to a rotating external magnetic field. The internal magnet is coupled to the one or more adjustable members to change a dimension of the ring shape as the internal magnet rotates. A system for treating a heart valve may include an external adjustment device having one or more external magnets to generate the rotating external magnetic field.

15 Claims, 38 Drawing Sheets

Related U.S. Application Data continuation of application No. 14/885,749, filed on Oct. 16, 2015, now Pat. No. 10,076,413, which is a continuation of application No. 13/625,725, filed on Sep. 24, 2012, now Pat. No. 9,198,755, which is a continuation of application No. 12/411,107, filed on Mar. 25, 2009, now abandoned.

(60) Provisional application No. 61/039,349, filed on Mar. 25, 2008.

(52) U.S. Cl.
CPC . *A61F 2210/009* (2013.01); *A61F 2250/0001* (2013.01); *A61F 2250/0004* (2013.01)

(56) References Cited

U.S. PATENT DOCUMENTS

| | | |
|---|---|---|
| 3,372,476 A | 3/1968 | Peiffer |
| 3,377,576 A | 4/1968 | Langberg |
| 3,512,901 A | 5/1970 | Law |
| 3,597,781 A | 8/1971 | Eibes |
| 3,900,025 A | 8/1975 | Barnes, Jr. |
| 3,915,151 A | 10/1975 | Kraus |
| RE28,907 E | 7/1976 | Eibes et al. |
| 3,976,060 A | 8/1976 | Hildebrandt et al. |
| 4,010,758 A | 3/1977 | Rockland et al. |
| 4,056,743 A | 11/1977 | Clifford et al. |
| 4,068,821 A | 1/1978 | Morrison |
| 4,078,559 A | 3/1978 | Nissinen |
| 4,204,541 A | 5/1980 | Kapitanov |
| 4,357,946 A | 11/1982 | Dutcher et al. |
| 4,386,603 A | 6/1983 | Mayfield |
| 4,448,191 A | 5/1984 | Rodnyansky et al. |
| 4,486,176 A | 12/1984 | Tardieu et al. |
| 4,501,266 A | 2/1985 | McDaniel |
| 4,522,501 A | 6/1985 | Shannon |
| 4,537,520 A | 8/1985 | Ochiai et al. |
| 4,550,279 A | 10/1985 | Klein |
| 4,561,798 A | 12/1985 | Elcrin et al. |
| 4,573,454 A | 3/1986 | Hoffman |
| 4,592,355 A | 6/1986 | Antebi |
| 4,595,007 A | 6/1986 | Mericle |
| 4,642,257 A | 2/1987 | Chase |
| 4,658,809 A | 4/1987 | Ulrich et al. |
| 4,700,091 A | 10/1987 | Wuthrich |
| 4,747,832 A | 5/1988 | Buffet |
| 4,854,304 A | 8/1989 | Zielke |
| 4,904,861 A | 2/1990 | Epstein et al. |
| 4,931,055 A | 6/1990 | Bumpus et al. |
| 4,940,467 A | 7/1990 | Tronzo |
| 4,957,495 A | 9/1990 | Kluger |
| 4,973,331 A | 11/1990 | Pursley et al. |
| 5,010,879 A | 4/1991 | Moriya et al. |
| 5,030,235 A | 7/1991 | Campbell, Jr. |
| 5,041,112 A | 8/1991 | Mingozzi et al. |
| 5,064,004 A | 11/1991 | Lundell |
| 5,074,882 A | 12/1991 | Grammont et al. |
| 5,092,889 A | 3/1992 | Campbell, Jr. |
| 5,133,716 A | 7/1992 | Plaza |
| 5,142,407 A | 8/1992 | Varaprasad et al. |
| 5,156,605 A | 10/1992 | Pursley et al. |
| 5,263,955 A | 11/1993 | Baumgart et al. |
| 5,290,289 A | 3/1994 | Sanders et al. |
| 5,306,275 A | 4/1994 | Bryan |
| 5,330,503 A | 7/1994 | Yoon |
| 5,334,202 A | 8/1994 | Carter |
| 5,336,223 A | 8/1994 | Rogers |
| 5,356,411 A | 10/1994 | Spievack |
| 5,356,424 A | 10/1994 | Buzerak et al. |
| 5,364,396 A | 11/1994 | Robinson et al. |
| 5,403,322 A | 4/1995 | Herzenberg et al. |
| 5,429,638 A | 7/1995 | Muschler et al. |
| 5,437,266 A | 8/1995 | McPherson et al. |
| 5,466,261 A | 11/1995 | Richelsoph |
| 5,468,030 A | 11/1995 | Walling |
| 5,480,437 A | 1/1996 | Draenert |
| 5,509,888 A | 4/1996 | Miller |
| 5,516,335 A | 5/1996 | Kummer et al. |
| 5,527,309 A | 6/1996 | Shelton |
| 5,536,269 A | 7/1996 | Spievack |
| 5,549,610 A | 8/1996 | Russell et al. |
| 5,573,012 A | 11/1996 | McEwan |
| 5,575,790 A | 11/1996 | Chen et al. |
| 5,582,616 A | 12/1996 | Bolduc et al. |
| 5,620,445 A | 4/1997 | Brosnahan et al. |
| 5,620,449 A | 4/1997 | Faccioli et al. |
| 5,626,579 A | 5/1997 | Muschler et al. |
| 5,626,613 A | 5/1997 | Schmieding |
| 5,632,744 A | 5/1997 | Campbell, Jr. |
| 5,659,217 A | 8/1997 | Petersen |
| 5,662,683 A | 9/1997 | Kay |
| 5,672,175 A | 9/1997 | Martin |
| 5,672,177 A | 9/1997 | Seldin |
| 5,700,263 A | 12/1997 | Schendel |
| 5,704,938 A | 1/1998 | Staehlin et al. |
| 5,704,939 A | 1/1998 | Justin |
| 5,720,746 A | 2/1998 | Soubeiran |
| 5,743,910 A | 4/1998 | Bays et al. |
| 5,762,599 A | 6/1998 | Sohn |
| 5,771,903 A | 6/1998 | Jakobsson |
| 5,810,815 A | 9/1998 | Morales |
| 5,827,286 A | 10/1998 | Incavo et al. |
| 5,830,221 A | 11/1998 | Stein et al. |
| 5,879,375 A | 3/1999 | Larson, Jr. et al. |
| 5,902,304 A | 5/1999 | Walker et al. |
| 5,935,127 A | 8/1999 | Border |
| 5,945,762 A | 8/1999 | Chen et al. |
| 5,961,553 A | 10/1999 | Coty et al. |
| 5,976,138 A | 11/1999 | Baumgart et al. |
| 5,979,456 A | 11/1999 | Magovern |
| 6,022,349 A | 2/2000 | McLeod et al. |
| 6,033,412 A | 3/2000 | Losken et al. |
| 6,034,296 A | 3/2000 | Elvin et al. |
| 6,102,922 A | 8/2000 | Jakobsson et al. |
| 6,106,525 A | 8/2000 | Sachse |
| 6,126,660 A | 10/2000 | Dietz |
| 6,126,661 A | 10/2000 | Faccioli et al. |
| 6,138,681 A | 10/2000 | Chen et al. |
| 6,139,316 A | 10/2000 | Sachdeva et al. |
| 6,162,223 A | 12/2000 | Orsak et al. |
| 6,183,476 B1 | 2/2001 | Gerhardt et al. |
| 6,200,317 B1 | 3/2001 | Aalsma et al. |
| 6,234,956 B1 | 5/2001 | He et al. |
| 6,241,730 B1 | 6/2001 | Alby |
| 6,245,075 B1 | 6/2001 | Betz et al. |
| 6,315,784 B1 | 11/2001 | Djurovic |
| 6,319,255 B1 | 11/2001 | Grundei et al. |
| 6,331,744 B1 | 12/2001 | Chen et al. |
| 6,336,929 B1 | 1/2002 | Justin |
| 6,343,568 B1 | 2/2002 | McClasky |
| 6,358,283 B1 | 3/2002 | Hogfors et al. |
| 6,375,682 B1 | 4/2002 | Fleischmann et al. |
| 6,389,187 B1 | 5/2002 | Greenaway et al. |
| 6,400,980 B1 | 6/2002 | Lemelson |
| 6,402,753 B1 | 6/2002 | Cole et al. |
| 6,409,175 B1 | 6/2002 | Evans et al. |
| 6,416,516 B1 | 7/2002 | Stauch et al. |
| 6,499,907 B1 | 12/2002 | Baur |
| 6,500,110 B1 | 12/2002 | Davey et al. |
| 6,508,820 B2 | 1/2003 | Bales |
| 6,510,345 B1 | 1/2003 | Van Bentem |
| 6,537,196 B1 | 3/2003 | Creighton, IV et al. |
| 6,554,831 B1 | 4/2003 | Rivard et al. |
| 6,565,573 B1 | 5/2003 | Ferrante et al. |
| 6,565,576 B1 | 5/2003 | Stauch et al. |
| 6,582,313 B2 | 6/2003 | Perrow |
| 6,583,630 B2 | 6/2003 | Mendes et al. |
| 6,616,669 B2 | 9/2003 | Ogilvie et al. |
| 6,626,917 B1 | 9/2003 | Craig |
| 6,656,135 B2 | 12/2003 | Zogbi et al. |
| 6,656,194 B1 | 12/2003 | Gannoe et al. |
| 6,667,725 B1 | 12/2003 | Simons et al. |
| 6,673,079 B1 | 1/2004 | Kane |

(56) References Cited

U.S. PATENT DOCUMENTS

| | | |
|---|---|---|
| 6,702,816 B2 | 3/2004 | Buhler |
| 6,706,042 B2 | 3/2004 | Taylor |
| 6,709,293 B2 | 3/2004 | Mori et al. |
| 6,730,087 B1 | 5/2004 | Butsch |
| 6,761,503 B2 | 7/2004 | Breese |
| 6,769,499 B2 | 8/2004 | Cargill et al. |
| 6,789,442 B2 | 9/2004 | Forch |
| 6,796,984 B2 | 9/2004 | Soubeiran |
| 6,802,844 B2 | 10/2004 | Ferree |
| 6,809,434 B1 | 10/2004 | Duncan et al. |
| 6,835,207 B2 | 12/2004 | Zacouto et al. |
| 6,852,113 B2 | 2/2005 | Nathanson et al. |
| 6,918,838 B2 | 7/2005 | Schwarzler et al. |
| 6,918,910 B2 | 7/2005 | Smith et al. |
| 6,921,400 B2 | 7/2005 | Sohngen |
| 6,923,951 B2 | 8/2005 | Contag et al. |
| 6,971,143 B2 | 12/2005 | Domroese |
| 7,001,346 B2 | 2/2006 | White |
| 7,008,425 B2 | 3/2006 | Phillips |
| 7,011,658 B2 | 3/2006 | Young |
| 7,029,472 B1 | 4/2006 | Fortin |
| 7,029,475 B2 | 4/2006 | Panjabi |
| 7,041,105 B2 | 5/2006 | Michelson |
| 7,060,080 B2 | 6/2006 | Bachmann |
| 7,063,706 B2 | 6/2006 | Wittenstein |
| 7,105,029 B2 | 9/2006 | Doubler et al. |
| 7,105,968 B2 | 9/2006 | Nissen |
| 7,114,501 B2 | 10/2006 | Johnson et al. |
| 7,115,129 B2 | 10/2006 | Heggeness |
| 7,135,022 B2 | 11/2006 | Kosashvili et al. |
| 7,160,312 B2 | 1/2007 | Saadat |
| 7,163,538 B2 | 1/2007 | Altarac et al. |
| 7,189,005 B2 | 3/2007 | Ward |
| 7,191,007 B2 | 3/2007 | Desai et al. |
| 7,218,232 B2 | 5/2007 | DiSilvestro et al. |
| 7,238,191 B2 | 7/2007 | Bachmann |
| 7,241,300 B2 | 7/2007 | Sharkawy et al. |
| 7,243,719 B2 | 7/2007 | Baron et al. |
| 7,255,682 B1 | 8/2007 | Bartol, Jr. et al. |
| 7,282,023 B2 | 10/2007 | Frering |
| 7,285,087 B2 | 10/2007 | Moaddeb et al. |
| 7,302,015 B2 | 11/2007 | Kim et al. |
| 7,302,858 B2 | 12/2007 | Walsh et al. |
| 7,314,443 B2 | 1/2008 | Jordan et al. |
| 7,333,013 B2 | 2/2008 | Berger |
| 7,357,037 B2 | 4/2008 | Hnat et al. |
| 7,357,635 B2 | 4/2008 | Belfor et al. |
| 7,360,542 B2 | 4/2008 | Nelson et al. |
| 7,390,007 B2 | 6/2008 | Helms et al. |
| 7,390,294 B2 | 6/2008 | Hassler, Jr. |
| 7,402,134 B2 | 7/2008 | Moaddeb et al. |
| 7,402,176 B2 | 7/2008 | Malek |
| 7,429,259 B2 | 9/2008 | Cadeddu et al. |
| 7,445,010 B2 | 11/2008 | Kugler et al. |
| 7,458,981 B2 | 12/2008 | Fielding et al. |
| 7,485,143 B2 | 2/2009 | Webler et al. |
| 7,485,149 B1 | 2/2009 | White |
| 7,489,495 B2 | 2/2009 | Stevenson |
| 7,530,981 B2 | 5/2009 | Kutsenko |
| 7,531,002 B2 | 5/2009 | Sutton et al. |
| 7,553,298 B2 | 6/2009 | Hunt et al. |
| 7,561,916 B2 | 7/2009 | Hunt et al. |
| 7,611,526 B2 | 11/2009 | Carl et al. |
| 7,618,435 B2 | 11/2009 | Opolski |
| 7,658,754 B2 | 2/2010 | Zhang et al. |
| 7,666,184 B2 | 2/2010 | Stauch |
| 7,666,210 B2 | 2/2010 | Franck et al. |
| 7,678,136 B2 | 3/2010 | Doubler et al. |
| 7,678,139 B2 | 3/2010 | Garamszegi et al. |
| 7,708,737 B2 | 5/2010 | Kraft et al. |
| 7,708,762 B2 | 5/2010 | McCarthy et al. |
| 7,727,143 B2 | 6/2010 | Birk et al. |
| 7,753,913 B2 | 7/2010 | Szakelyhidi, Jr. et al. |
| 7,753,915 B1 | 7/2010 | Eksler et al. |
| 7,762,998 B2 | 7/2010 | Birk et al. |
| 7,763,080 B2 | 7/2010 | Southworth |
| 7,766,855 B2 | 8/2010 | Miethke |
| 7,775,215 B2 | 8/2010 | Hassler, Jr. et al. |
| 7,776,068 B2 | 8/2010 | Ainsworth et al. |
| 7,776,075 B2 | 8/2010 | Bruneau et al. |
| 7,787,958 B2 | 8/2010 | Stevenson |
| 7,794,476 B2 | 9/2010 | Wisnewski |
| 7,811,328 B2 | 10/2010 | Molz, IV et al. |
| 7,835,779 B2 | 11/2010 | Anderson et al. |
| 7,837,691 B2 | 11/2010 | Cordes et al. |
| 7,862,586 B2 | 1/2011 | Malek |
| 7,867,235 B2 | 1/2011 | Fell et al. |
| 7,875,033 B2 | 1/2011 | Richter et al. |
| 7,901,381 B2 | 3/2011 | Birk et al. |
| 7,909,852 B2 | 3/2011 | Boomer et al. |
| 7,918,844 B2 | 4/2011 | Byrum et al. |
| 7,938,841 B2 | 5/2011 | Sharkawy et al. |
| 7,985,256 B2 | 7/2011 | Grotz et al. |
| 7,988,709 B2 | 8/2011 | Clark et al. |
| 8,002,809 B2 | 8/2011 | Baynham |
| 8,011,308 B2 | 9/2011 | Picchio |
| 8,034,080 B2 | 10/2011 | Malandain et al. |
| 8,043,299 B2 | 10/2011 | Conway |
| 8,043,338 B2 | 10/2011 | Dant |
| 8,057,473 B2 | 11/2011 | Orsak et al. |
| 8,057,513 B2 | 11/2011 | Kohm et al. |
| 8,083,741 B2 | 12/2011 | Morgan et al. |
| 8,092,499 B1 | 1/2012 | Roth |
| 8,095,317 B2 | 1/2012 | Ekseth et al. |
| 8,105,360 B1 | 1/2012 | Connor |
| 8,114,158 B2 | 2/2012 | Carl et al. |
| 8,123,805 B2 | 2/2012 | Makower et al. |
| 8,133,280 B2 | 3/2012 | Voellmicke et al. |
| 8,147,549 B2 | 4/2012 | Metcalf, Jr. et al. |
| 8,162,897 B2 | 4/2012 | Byrum |
| 8,162,979 B2 | 4/2012 | Sachs et al. |
| 8,177,789 B2 | 5/2012 | Magill et al. |
| 8,197,490 B2 | 6/2012 | Pool et al. |
| 8,211,149 B2 | 7/2012 | Justis |
| 8,211,151 B2 | 7/2012 | Schwab et al. |
| 8,221,420 B2 | 7/2012 | Keller |
| 8,226,690 B2 | 7/2012 | Altarac et al. |
| 8,236,002 B2 | 8/2012 | Fortin et al. |
| 8,241,331 B2 | 8/2012 | Arnin |
| 8,246,630 B2 | 8/2012 | Manzi et al. |
| 8,252,063 B2 | 8/2012 | Stauch |
| 8,267,969 B2 | 9/2012 | Altarac et al. |
| 8,278,941 B2 | 10/2012 | Kroh et al. |
| 8,282,671 B2 | 10/2012 | Connor |
| 8,323,290 B2 | 12/2012 | Metzger et al. |
| 8,357,182 B2 | 1/2013 | Seme |
| 8,366,628 B2 | 2/2013 | Denker et al. |
| 8,372,078 B2 | 2/2013 | Collazo |
| 8,386,018 B2 | 2/2013 | Stauch et al. |
| 8,394,124 B2 | 3/2013 | Biyani |
| 8,403,958 B2 | 3/2013 | Schwab |
| 8,414,584 B2 | 4/2013 | Brigido |
| 8,425,608 B2 | 4/2013 | Dewey et al. |
| 8,435,268 B2 | 5/2013 | Thompson et al. |
| 8,439,926 B2 | 5/2013 | Bojarski et al. |
| 8,444,693 B2 | 5/2013 | Reiley |
| 8,469,908 B2 | 6/2013 | Asfora |
| 8,470,004 B2 | 6/2013 | Reiley |
| 8,486,070 B2 | 7/2013 | Morgan et al. |
| 8,486,076 B2 | 7/2013 | Chavarria et al. |
| 8,486,147 B2 | 7/2013 | De Villiers et al. |
| 8,494,805 B2 | 7/2013 | Roche et al. |
| 8,496,662 B2 | 7/2013 | Novak et al. |
| 8,518,062 B2 | 8/2013 | Cole et al. |
| 8,523,866 B2 | 9/2013 | Sidebotham et al. |
| 8,529,474 B2 | 9/2013 | Gupta et al. |
| 8,529,606 B2 | 9/2013 | Alamin et al. |
| 8,529,607 B2 | 9/2013 | Alamin et al. |
| 8,556,901 B2 | 10/2013 | Anthony et al. |
| 8,556,911 B2 | 10/2013 | Mehta et al. |
| 8,556,975 B2 | 10/2013 | Ciupik et al. |
| 8,562,653 B2 | 10/2013 | Alamin et al. |
| 8,568,457 B2 | 10/2013 | Hunziker |
| 8,617,220 B2 | 10/2013 | Skaggs |

(56) References Cited

U.S. PATENT DOCUMENTS

| | | |
|---|---|---|
| 8,579,979 B2 | 11/2013 | Edie et al. |
| 8,585,595 B2 | 11/2013 | Heilman |
| 8,585,740 B1 | 11/2013 | Ross et al. |
| 8,591,549 B2 | 11/2013 | Lange |
| 8,591,553 B2 | 11/2013 | Eisermann et al. |
| 8,613,758 B2 | 12/2013 | Linares |
| 8,623,036 B2 * | 1/2014 | Harrison ............... A61B 17/11 606/153 |
| 8,632,544 B2 | 1/2014 | Haaja et al. |
| 8,632,548 B2 | 1/2014 | Soubeiran |
| 8,632,563 B2 | 1/2014 | Nagase et al. |
| 8,636,771 B2 | 1/2014 | Butler et al. |
| 8,636,802 B2 | 1/2014 | Serhan et al. |
| 8,641,719 B2 | 2/2014 | Gephart et al. |
| 8,641,723 B2 * | 2/2014 | Connor ............... A61B 17/7016 606/57 |
| 8,657,856 B2 | 2/2014 | Gephart et al. |
| 8,663,285 B2 | 3/2014 | Dall et al. |
| 8,663,287 B2 | 3/2014 | Butler et al. |
| 8,668,719 B2 | 3/2014 | Alamin et al. |
| 8,709,090 B2 | 4/2014 | Makower et al. |
| 8,721,718 B2 * | 5/2014 | Kassab ............ A61B 17/12122 623/2.37 |
| 8,758,347 B2 | 6/2014 | Weiner et al. |
| 8,758,355 B2 | 6/2014 | Fisher et al. |
| 8,771,272 B2 | 7/2014 | LeCronier et al. |
| 8,777,947 B2 | 7/2014 | Zahrly et al. |
| 8,777,995 B2 | 7/2014 | McClintock et al. |
| 8,790,343 B2 | 7/2014 | McClellan et al. |
| 8,790,409 B2 | 7/2014 | Van den Heuvel et al. |
| 8,828,058 B2 | 9/2014 | Elsebaie et al. |
| 8,828,087 B2 | 9/2014 | Stone et al. |
| 8,840,651 B2 | 9/2014 | Reiley |
| 8,870,881 B2 | 10/2014 | Rezach et al. |
| 8,870,959 B2 | 10/2014 | Arnin |
| 8,915,915 B2 | 12/2014 | Harrison et al. |
| 8,915,917 B2 | 12/2014 | Doherty et al. |
| 8,920,422 B2 | 12/2014 | Homeier et al. |
| 8,945,188 B2 | 2/2015 | Rezach et al. |
| 8,961,521 B2 | 2/2015 | Keefer et al. |
| 8,961,567 B2 | 2/2015 | Hunziker |
| 8,968,402 B2 | 3/2015 | Myers et al. |
| 8,992,527 B2 | 3/2015 | Guichet |
| 9,022,917 B2 | 5/2015 | Kasic et al. |
| 9,044,218 B2 | 6/2015 | Young |
| 9,060,810 B2 | 6/2015 | Kercher et al. |
| 9,078,703 B2 | 7/2015 | Arnin |
| 10,076,413 B2 * | 9/2018 | Shaolian ............... A61F 2/2448 |
| 2002/0050112 A1 | 5/2002 | Koch et al. |
| 2002/0072758 A1 | 6/2002 | Reo et al. |
| 2002/0164905 A1 | 11/2002 | Bryant |
| 2003/0040671 A1 | 2/2003 | Somogyi et al. |
| 2003/0144669 A1 | 7/2003 | Robinson |
| 2003/0220643 A1 | 11/2003 | Ferree |
| 2003/0220644 A1 | 11/2003 | Thelen et al. |
| 2004/0011137 A1 | 1/2004 | Hnat et al. |
| 2004/0011365 A1 | 1/2004 | Govari et al. |
| 2004/0019353 A1 | 1/2004 | Freid et al. |
| 2004/0023623 A1 | 2/2004 | Stauch et al. |
| 2004/0055610 A1 | 3/2004 | Forsell |
| 2004/0133219 A1 | 7/2004 | Forsell |
| 2004/0138725 A1 | 7/2004 | Forsell |
| 2004/0193266 A1 | 9/2004 | Meyer |
| 2005/0034705 A1 | 2/2005 | McClendon |
| 2005/0049617 A1 | 3/2005 | Chatlynne et al. |
| 2005/0060030 A1 | 3/2005 | Lashinski et al. |
| 2005/0065529 A1 | 3/2005 | Liu et al. |
| 2005/0090823 A1 | 4/2005 | Bartimus |
| 2005/0159754 A1 | 7/2005 | Odrich |
| 2005/0234448 A1 | 10/2005 | McCarthy |
| 2005/0234462 A1 | 10/2005 | Hershberger |
| 2005/0246034 A1 | 11/2005 | Soubeiran |
| 2005/0261779 A1 | 11/2005 | Meyer |
| 2005/0272976 A1 | 12/2005 | Tanaka et al. |
| 2006/0004459 A1 | 1/2006 | Hazebrouck et al. |
| 2006/0009767 A1 | 1/2006 | Kiester |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0047282 A1 | 3/2006 | Gordon |
| 2006/0058792 A1 | 3/2006 | Hynes |
| 2006/0069447 A1 | 3/2006 | DiSilvestro et al. |
| 2006/0074448 A1 | 4/2006 | Harrison et al. |
| 2006/0079897 A1 | 4/2006 | Harrison et al. |
| 2006/0136062 A1 | 6/2006 | DiNello et al. |
| 2006/0142767 A1 | 6/2006 | Green et al. |
| 2006/0155279 A1 | 7/2006 | Ogilvie |
| 2006/0195087 A1 | 8/2006 | Sacher et al. |
| 2006/0195088 A1 | 8/2006 | Sacher et al. |
| 2006/0200134 A1 | 9/2006 | Freid et al. |
| 2006/0204156 A1 | 9/2006 | Takehara et al. |
| 2006/0235299 A1 | 10/2006 | Martinelli |
| 2006/0235424 A1 | 10/2006 | Vitale et al. |
| 2006/0241746 A1 | 10/2006 | Shaoulian et al. |
| 2006/0241748 A1 | 10/2006 | Lee et al. |
| 2006/0241767 A1 | 10/2006 | Doty |
| 2006/0249914 A1 | 11/2006 | Dulin |
| 2006/0252982 A1 | 11/2006 | Hassler, Jr. et al. |
| 2006/0271107 A1 | 11/2006 | Harrison et al. |
| 2006/0282073 A1 | 12/2006 | Simanovsky |
| 2006/0293683 A1 | 12/2006 | Stauch |
| 2007/0004999 A1 | 1/2007 | Miethke |
| 2007/0010814 A1 | 1/2007 | Stauch |
| 2007/0010887 A1 | 1/2007 | Williams et al. |
| 2007/0021644 A1 | 1/2007 | Woolson et al. |
| 2007/0027356 A1 | 2/2007 | Ortiz |
| 2007/0031131 A1 | 2/2007 | Griffitts |
| 2007/0043376 A1 | 2/2007 | Leatherbury et al. |
| 2007/0050030 A1 | 3/2007 | Kim |
| 2007/0118215 A1 | 5/2007 | Moaddeb |
| 2007/0161984 A1 | 7/2007 | Cresina et al. |
| 2007/0173837 A1 | 7/2007 | Chan et al. |
| 2007/0179493 A1 | 8/2007 | Kim |
| 2007/0185374 A1 | 8/2007 | Kick et al. |
| 2007/0213751 A1 | 9/2007 | Scirica et al. |
| 2007/0233098 A1 | 10/2007 | Mastrorio et al. |
| 2007/0233239 A1 * | 10/2007 | Navia ............... A61F 2/2466 623/2.37 |
| 2007/0239159 A1 | 10/2007 | Altarac et al. |
| 2007/0239161 A1 | 10/2007 | Giger et al. |
| 2007/0255088 A1 | 11/2007 | Jacobson et al. |
| 2007/0270803 A1 | 11/2007 | Giger et al. |
| 2007/0276368 A1 | 11/2007 | Trieu et al. |
| 2007/0276369 A1 | 11/2007 | Allard et al. |
| 2007/0276373 A1 | 11/2007 | Malandain |
| 2007/0276378 A1 | 11/2007 | Harrison et al. |
| 2007/0276493 A1 | 11/2007 | Malandain et al. |
| 2007/0288024 A1 | 12/2007 | Gollogly |
| 2007/0288183 A1 | 12/2007 | Bulkes et al. |
| 2008/0009792 A1 | 1/2008 | Henniges et al. |
| 2008/0015577 A1 | 1/2008 | Loeb |
| 2008/0021454 A1 | 1/2008 | Chao et al. |
| 2008/0021455 A1 | 1/2008 | Chao et al. |
| 2008/0021456 A1 | 1/2008 | Gupta et al. |
| 2008/0027436 A1 | 1/2008 | Cournoyer et al. |
| 2008/0033431 A1 | 2/2008 | Jung et al. |
| 2008/0033436 A1 | 2/2008 | Song et al. |
| 2008/0051784 A1 | 2/2008 | Gollogly |
| 2008/0082118 A1 | 4/2008 | Edidin et al. |
| 2008/0086128 A1 | 4/2008 | Lewis |
| 2008/0091264 A1 | 4/2008 | Machold et al. |
| 2008/0097487 A1 | 4/2008 | Pool et al. |
| 2008/0097496 A1 | 4/2008 | Chang et al. |
| 2008/0108995 A1 | 5/2008 | Conway et al. |
| 2008/0109076 A1 | 5/2008 | Cartledge et al. |
| 2008/0161933 A1 | 7/2008 | Grotz et al. |
| 2008/0167685 A1 | 7/2008 | Allard et al. |
| 2008/0172063 A1 | 7/2008 | Taylor |
| 2008/0177319 A1 | 7/2008 | Schwab |
| 2008/0177326 A1 | 7/2008 | Thompson |
| 2008/0183285 A1 | 7/2008 | Shaoulian et al. |
| 2008/0190237 A1 | 8/2008 | Radinger et al. |
| 2008/0228186 A1 | 9/2008 | Gall et al. |
| 2008/0243150 A1 | 10/2008 | Starksen et al. |

(56) References Cited

U.S. PATENT DOCUMENTS

| | | |
|---|---|---|
| 2008/0255615 A1 | 10/2008 | Vittur et al. |
| 2008/0272928 A1 | 11/2008 | Shuster |
| 2008/0275557 A1 | 11/2008 | Makower et al. |
| 2009/0030462 A1 | 1/2009 | Buttermann |
| 2009/0076597 A1 | 3/2009 | Dahlgren et al. |
| 2009/0082815 A1 | 3/2009 | Zylber et al. |
| 2009/0088803 A1 | 4/2009 | Justis et al. |
| 2009/0093820 A1 | 4/2009 | Trieu et al. |
| 2009/0093890 A1 | 4/2009 | Gelbart |
| 2009/0112263 A1 | 4/2009 | Pool et al. |
| 2009/0163780 A1 | 6/2009 | Tieu |
| 2009/0171356 A1 | 7/2009 | Klett |
| 2009/0192514 A1 | 7/2009 | Feinberg et al. |
| 2009/0198144 A1 | 8/2009 | Phillips et al. |
| 2009/0216113 A1 | 8/2009 | Meier et al. |
| 2009/0275984 A1 | 11/2009 | Kim et al. |
| 2010/0004654 A1 | 1/2010 | Schmitz et al. |
| 2010/0057127 A1 | 3/2010 | McGuire et al. |
| 2010/0094306 A1 | 4/2010 | Chang et al. |
| 2010/0100185 A1 | 4/2010 | Trieu et al. |
| 2010/0106192 A1 | 4/2010 | Barry |
| 2010/0114322 A1 | 5/2010 | Clifford et al. |
| 2010/0130941 A1 | 5/2010 | Conlon et al. |
| 2010/0137872 A1 | 6/2010 | Kam et al. |
| 2010/0145449 A1 | 6/2010 | Makower et al. |
| 2010/0145462 A1 | 6/2010 | Ainsworth et al. |
| 2010/0168751 A1 | 7/2010 | Anderson et al. |
| 2010/0249782 A1 | 9/2010 | Durham |
| 2010/0256626 A1 | 10/2010 | Muller et al. |
| 2010/0262239 A1 | 10/2010 | Boyden et al. |
| 2010/0318129 A1 | 12/2010 | Seme et al. |
| 2010/0331883 A1 | 12/2010 | Schmitz et al. |
| 2011/0004076 A1 | 1/2011 | Janna et al. |
| 2011/0009956 A1 | 1/2011 | Cartledge et al. |
| 2011/0022169 A1 | 1/2011 | Ryan et al. |
| 2011/0057756 A1 | 3/2011 | Marinescu et al. |
| 2011/0060407 A1* | 3/2011 | Ketai ............... A61B 17/0644 623/2.37 |
| 2011/0066188 A1 | 3/2011 | Seme et al. |
| 2011/0098748 A1 | 4/2011 | Jangra |
| 2011/0152725 A1 | 6/2011 | Demir et al. |
| 2011/0190879 A1* | 8/2011 | Bobo ............... A61F 2/2487 623/2.37 |
| 2011/0196435 A1 | 8/2011 | Forsell |
| 2011/0202138 A1 | 8/2011 | Shenoy et al. |
| 2011/0230961 A1* | 9/2011 | Langer ............... A61F 2/2448 623/2.27 |
| 2011/0238126 A1 | 9/2011 | Soubeiran |
| 2011/0238171 A1* | 9/2011 | Carpentier ............ A61F 2/2448 623/2.36 |
| 2011/0257655 A1 | 10/2011 | Copf, Jr. |
| 2011/0284014 A1 | 11/2011 | Cadeddu et al. |
| 2011/0313516 A1* | 12/2011 | Dang ............... A61F 2/2445 623/2.11 |
| 2012/0019341 A1 | 1/2012 | Gabay et al. |
| 2012/0019342 A1 | 1/2012 | Gabay et al. |
| 2012/0053633 A1 | 3/2012 | Stauch |
| 2012/0053687 A1* | 3/2012 | Migliazza ............ A61F 2/2445 623/2.37 |
| 2012/0088953 A1 | 4/2012 | King |
| 2012/0109207 A1 | 5/2012 | Trieu |
| 2012/0116535 A1 | 5/2012 | Ratron et al. |
| 2012/0136436 A1 | 5/2012 | Cabiri et al. |
| 2012/0158061 A1 | 6/2012 | Koch et al. |
| 2012/0172883 A1 | 7/2012 | Sayago |
| 2012/0179215 A1 | 7/2012 | Soubeiran |
| 2012/0197392 A1 | 8/2012 | DuMontelle et al. |
| 2012/0221101 A1* | 8/2012 | Moaddeb ............ A61F 2/2445 623/2.37 |
| 2012/0221106 A1 | 8/2012 | Makower et al. |
| 2012/0245678 A1* | 9/2012 | Solem ............... A61M 60/871 623/2.36 |
| 2012/0271353 A1 | 10/2012 | Barry |
| 2012/0296234 A1 | 11/2012 | Wilhelm et al. |
| 2012/0329882 A1 | 12/2012 | Messersmith et al. |
| 2013/0013059 A1 | 1/2013 | Tozzi et al. |
| 2013/0013066 A1 | 1/2013 | Landry et al. |
| 2013/0072932 A1 | 3/2013 | Stauch |
| 2013/0123847 A1 | 5/2013 | Anderson et al. |
| 2013/0138017 A1 | 5/2013 | Jundt et al. |
| 2013/0138154 A1 | 5/2013 | Reiley |
| 2013/0150863 A1 | 6/2013 | Baumgartner |
| 2013/0150889 A1 | 6/2013 | Fening et al. |
| 2013/0178903 A1 | 7/2013 | Abdou |
| 2013/0211521 A1 | 8/2013 | Shenoy et al. |
| 2013/0245692 A1 | 9/2013 | Hayes et al. |
| 2013/0253344 A1 | 9/2013 | Griswold et al. |
| 2013/0253587 A1 | 9/2013 | Carls et al. |
| 2013/0261672 A1 | 10/2013 | Horvath |
| 2013/0296863 A1 | 11/2013 | Globerman et al. |
| 2013/0296864 A1 | 11/2013 | Burley et al. |
| 2013/0296940 A1 | 11/2013 | Northcutt et al. |
| 2013/0325006 A1 | 12/2013 | Michelinie et al. |
| 2013/0325071 A1 | 12/2013 | Niemiec et al. |
| 2013/0338467 A1* | 12/2013 | Grasse ............... A61B 18/1492 606/41 |
| 2014/0005788 A1 | 1/2014 | Haaja et al. |
| 2014/0025172 A1 | 1/2014 | Lucas et al. |
| 2014/0052134 A1 | 2/2014 | Orisek |
| 2014/0058392 A1 | 2/2014 | Mueckter et al. |
| 2014/0058450 A1 | 2/2014 | Arlet |
| 2014/0066987 A1 | 3/2014 | Hestad et al. |
| 2014/0088715 A1 | 3/2014 | Ciupik |
| 2014/0128920 A1 | 5/2014 | Kantelhardt |
| 2014/0163664 A1 | 6/2014 | Goldsmith |
| 2014/0236234 A1 | 8/2014 | Kroll et al. |
| 2014/0236311 A1 | 8/2014 | Vicatos et al. |
| 2014/0257412 A1 | 9/2014 | Patty et al. |
| 2014/0277420 A1* | 9/2014 | Migliazza ............ A61F 2/2448 29/428 |
| 2014/0277446 A1 | 9/2014 | Clifford et al. |
| 2014/0296918 A1 | 10/2014 | Fening et al. |
| 2014/0303538 A1 | 10/2014 | Baym et al. |
| 2014/0303539 A1 | 10/2014 | Baym et al. |
| 2014/0358150 A1 | 12/2014 | Kaufman et al. |
| 2015/0105782 A1 | 4/2015 | D'Lima et al. |
| 2015/0105824 A1 | 4/2015 | Moskowitz et al. |
| 2015/0112432 A1 | 4/2015 | Reich et al. |
| 2015/0223820 A1 | 8/2015 | Olson et al. |
| 2016/0135953 A1 | 5/2016 | Alon et al. |
| 2017/0216031 A1* | 8/2017 | Machold ......... A61B 17/00234 |
| 2017/0367825 A1 | 12/2017 | Cabiri et al. |
| 2019/0000620 A1* | 1/2019 | Shaolian ............ A61F 2/2442 |
| 2022/0163764 A1* | 5/2022 | Chiang ................ H04N 23/80 |
| 2022/0233316 A1* | 7/2022 | Sheps ................ A61F 2/2496 |
| 2023/0017801 A1* | 1/2023 | Petersen ............ A61F 2/2445 |
| 2024/0138987 A1* | 5/2024 | Machold ............. A61F 2/2466 |

FOREIGN PATENT DOCUMENTS

| | | |
|---|---|---|
| DE | 1541262 A1 | 6/1969 |
| DE | 8515687 U1 | 12/1985 |
| DE | 19626230 A1 | 1/1998 |
| DE | 19745654 A1 | 4/1999 |
| DE | 102005045070 A1 | 4/2007 |
| EP | 0663184 A1 | 7/1995 |
| EP | 1905388 A1 | 4/2008 |
| FR | 2901991 A1 | 12/2007 |
| FR | 2900563 B1 | 8/2008 |
| FR | 2892617 B1 | 9/2008 |
| FR | 2916622 B1 | 9/2009 |
| FR | 2961386 B1 | 12/2011 |
| JP | H0956736 | 3/1997 |
| JP | 2002500063 A | 1/2002 |
| WO | WO1998044858 A1 | 10/1998 |
| WO | WO1999051160 A1 | 10/1999 |
| WO | WO2001024697 A1 | 4/2001 |
| WO | WO2001045485 A3 | 6/2001 |
| WO | WO2001045487 A2 | 6/2001 |
| WO | WO2001067973 A2 | 9/2001 |
| WO | WO2001078614 A1 | 10/2001 |
| WO | WO2007013059 A3 | 2/2007 |
| WO | WO2007015239 A3 | 2/2007 |

(56) References Cited

FOREIGN PATENT DOCUMENTS

| WO | WO-2007118179 A2 * | 10/2007 | ............ A61B 17/00 |
|---|---|---|---|
| WO | WO2011116158 A3 | 9/2011 | |
| WO | WO2013119528 A1 | 8/2013 | |
| WO | WO2014040013 A1 | 3/2014 | |

OTHER PUBLICATIONS

Ahlbom et al., "Guidelines for limiting exposure to time-varying electric, magnetic, and electromagnetic fields (up to 300 GHz). International Commission on Non-Ionizing Radiation Protection.", Health Physics, 1998, pp. 494-522, 74, No. 4.

Amer et al., "Evaluation of treatment of late-onset tibia vara using gradual angulation translation high tibial osteotomy", ACTA Orthopaedica Belgica, 2010, pp. 360-366, 76, No. 3.

Angrisani et al., "Lap-Band® Rapid Port™ System: Preliminary results in 21 patients", Obesity Surgery, 2005, p. 936, 15, No. 7.

Baumgart et al., "A fully implantable, programmable distraction nail (Fitbone)—new perspectives for corrective and reconstructive limb surgery.", Practice of Intramedullary Locked Nails, 2006, pp. 189-198.

Baumgart et al., "The bioexpandable prosthesis: A new perspective after resection of malignant bone tumors in children.", J Pediatr Hematol Oncol, 2005, pp. 452-455, 27, No. 8.

Bodó et al., "Development of a tension-adjustable implant for anterior cruciate ligament reconstruction.", Eklem Hastaliklari ve Cerrahisi—Joint Diseases and Related Surgery, 2008, pp. 27-32, 19, No. 1.

Boudjemline et al., "Off-label use of an adjustable gastric banding system for pulmonary artery banding.", The Journal of Thoracic and Cardiovascular Surgery, 2006, pp. 1130-1135, 131, No. 5.

Brown et al., "Single port surgery and the Dundee Endocone.", SAGES Annual Scientific Sessions: Emerging Technology Poster Abstracts, 2007, ETP007, pp. 323-324.

Buchowski et al., "Temporary internal distraction as an aid to correction of severe scoliosis", J Bone Joint Surg Am, 2006, pp. 2035-2041, 88-A, No. 9.

Burghardt et al., "Mechanical failure of the Intramedullary Skeletal Kinetic Distractor in limb lengthening.", J Bone Joint Surg Br, 2011, pp. 639-643, 93-B, No. 5.

Burke, "Design of a minimally invasive non fusion device for the surgical management of scoliosis in the skeletally immature", Studies in Health Technology and Informatics, 2006, pp. 378-384, 123.

Carter et al., "A cumulative damage model for bone fracture.", Journal of Orthopaedic Research, 1985, pp. 84-90, 3, No. 1.

Chapman et al., "Laparoscopic adjustable gastric banding in the treatment of obesity: A systematic literature review.", Surgery, 2004, pp. 326-351, 135, No. 3.

Cole et al., "Operative technique intramedullary skeletal kinetic distractor: Tibial surgical technique.", Orthofix, 2005.

Cole et al., "The intramedullary skeletal kinetic distractor (ISKD): first clinical results of a new intramedullary nail for lengthening of the femur and tibia.", Injury, 2001, pp. S-D-129-S-D-139, 32.

Dailey et al., "A novel intramedullary nail for micromotion stimulation of tibial fractures.", Clinical Biomechanics, 2012, pp. 182-188, 27, No. 2.

Daniels et al., "A new method for continuous intraoperative measurement of Harrington rod loading patterns.", Annals of Biomedical Engineering, 1984, pp. 233-246, 12, No. 3.

De Giorgi et al., "Cotrel-Dubousset instrumentation for the treatment of severe scoliosis.", European Spine Journal, 1999, pp. 8-15, No. 1.

Dorsey et al., "The stability of three commercially available implants used in medial opening wedge high tibial osteotomy.", Journal of Knee Surgery, 2006, pp. 95-98, 19, No. 2.

Edeland et al., "Instrumentation for distraction by limited surgery in scoliosis treatment.", Journal of Biomedical Engineering, 1981, pp. 143-146, 3, No. 2.

Elsebaie, "Single growing rods (Review of 21 cases). Changing the foundations: Does it affect the results?", Journal of Child Orthop, 2007, 1:258.

Ember et al., "Distraction forces required during growth rod lengthening.", J of Bone Joint Surg BR, 2006, p. 229, 88-B, No. Suppl. II.

European Patent Office, "Observations by a third party under Article 115 EPC in EP08805612 by Soubeiran.", 2010.

Fabry et al., "A technique for prevention of port complications after laparoscopic adjustable silicone gastric banding.", Obesity Surgery, 2002, pp. 285-288, 12, No. 2.

Fried et al., "In vivo measurements of different gastric band pressures towards the gastric wall at the stoma region.", Obesity Surgery, 2004, p. 914, 14, No. 7.

Gao et al., CHD7 gene polymorphisms are associated with susceptibility to idiopathic scoliosis, American Journal of Human Genetics, 2007, pp. 957-965, 80.

Gebhart et al., "Early clinical experience with a custom made growing endoprosthesis in children with malignant bone tumors of the lower extremity actioned by an external permanent magnet; The Phenix M. system", International Society of Limb Salvage 14th International Symposium on Limb Salvage. Sep. 3, 2007, Hamburg, Germany. (2 pages).

Gillespie et al. "Harrington instrumentation without fusion.", J Bone Joint Surg Br, 1981, p. 461, 63-B, No. 3.

Goodship et al., "Strain rate and timing of stimulation in mechanical modulation of fracture healing.", Clinical Orthopaedics and Related Research, 1998, pp. S105-S115, No. 355S.

Grass et al., "Intermittent distracting rod for correction of high neurologic risk congenital scoliosis.", SPINE, 1997, pp. 1922-1927, 22, No. 16.

Gray, "Gray's anatomy of the human body.", http://education.yahoo.com/reference/gray/subjects/subject/128, published Jul. 1, 2007.

Grimer et al. "Non-invasive extendable endoprostheses for children—Expensive but worth it!", International Society of Limb Salvage 14th International Symposium on Limb Salvage, 2007.

Grünert, "The development of a totally implantable electronic sphincter." (translated from the German "Die Entwicklung eines total implantierbaren elektronischen Sphincters"), Langenbecks Archiv fur Chirurgie, 1969, pp. 1170-1174, 325.

Guichet et al. "Gradual femoral lengthening with the Albizzia intramedullary nail", J Bone Joint Surg Am, 2003, pp. 838-848, 85-A, No. 5.

Gupta et al., "Non-invasive distal femoral expandable endoprosthesis for limb-salvage surgery in paediatric tumours.", J Bone Joint Surg Br, 2006, pp. 649-654, 88-B, No. 5.

Hankemeier et al., "Limb lengthening with the Intramedullary Skeletal Kinetic Distractor (ISKD).", Oper Orthop Traumatol, 2005, pp. 79-101, 17, No. 1.

Harrington, "Treatment of scoliosis. Correction and internal fixation by spine instrumentation.", J Bone Joint Surg Am, 1962, pp. 591-610, 44-A, No. 4.

Hennig et al., "The safety and efficacy of a new adjustable plate used for proximal tibial opening wedge osteotomy in the treatment of unicompartmental knee osteoarthrosis.", Journal of Knee Surgery, 2007, pp. 6-14, 20, No. 1.

Hofmeister et al., "Callus distraction with the Albizzia nail.", Practice of Intramedullary Locked Nails, 2006, pp. 211-215.

Horbach et al., "First experiences with the routine use of the Rapid Port™ system with the Lap-Band®.", Obesity Surgery, 2006, p. 418, 16, No. 4.

Hyodo et al., "Bone transport using intramedullary fixation and a single flexible traction cable.", Clinical Orthopaedics and Related Research, 1996, pp. 256-268, 325.

International Commission on Non-Ionizing Radiation Protection, "Guidelines on limits of exposure to static magnetic fields." Health Physics, 2009, pp. 504-514, 96, No. 4.

INVIS®/Lamello Catalog, 2006, Article No. 68906A001 GB.

Kasliwal et al., "Management of high-grade spondylolisthesis.", Neurosurgery Clinics of North America, 2013, pp. 275-291, 24, No. 2.

Kenawey et al., "Leg lengthening using intramedullay skeletal kinetic distractor: Results of 57 consecutive applications.", Injury, 2011, pp. 150-155, 42, No. 2.

(56) References Cited

OTHER PUBLICATIONS

Kent et al., "Assessment and correction of femoral malrotation following intramedullary nailing of the femur.", Acta Orthop Belg, 2010, pp. 580-584, 76, No. 5.
Klemme et al., "Spinal instrumentation without fusion for progressive scoliosis in young children", Journal of Pediatric Orthopaedics. 1997, pp. 734-742, 17, No. 6.
Korenkov et al., "Port function after laparoscopic adjustable gastric banding for morbid obesity.", Surgical Endoscopy, 2003, pp. 1068-1071, 17, No. 7.
Krieg et al., "Leg lengthening with a motorized nail in adolescents.", Clinical Orthopaedics and Related Research, 2008, pp. 189-197, 466, No. 1.
Kucukkaya et al., "The new intramedullary cable bone transport technique.", Journal of Orthopaedic Trauma, 2009, pp. 531-536, 23, No. 7.
Lechner et al., "In vivo band manometry: A new method in band adjustment", Obesity Surgery, 2005, p. 935, 15, No. 7.
Lechner et al., "Intra-band manometry for band adjustments: The basics", Obesity Surgery, 2006, pp. 417-418, 16, No. 4.
Li et al., "Bone transport over an intramedullary nail: A case report with histologic examination of the regenerated segment.", Injury, 1999, pp. 525-534, 30, No. 8.
Lonner, "Emerging minimally invasive technologies for the management of scoliosis.", Orthopedic Clinics of North America, 2007, pp. 431-440, 38, No. 3.
Matthews et al., "Magnetically adjustable intraocular lens.", Journal of Cataract and Refractive Surgery, 2003, pp. 2211-2216, 29, No. 11.
Micromotion, "Micro Drive Engineering. General catalogue.", 2009, pp. 14-24.
Mineiro et al., "Subcutaneous rodding for progressive spinal curvatures: Early results.", Journal of Pediatric Orthopaedics, 2002, pp. 290-295, 22, No. 3.
Moe et al., "Harrington instrumentation without fusion plus external orthotic support for the treatment of difficult curvature problems in young children.", Clinical Orthopaedics and Related Research, 1984, pp. 35-45, 185.
Montague et al., "Magnetic gear dynamics for servo control.", Melecon 2010—2010 15th IEEE Mediterranean Electrotechnical Conference, Valletta, 2010, pp. 1192-1197.
Montague et al., "Servo control of magnetic gears.", IEEE/ASME Transactions on Mechatronics, 2012, pp. 269-278, 17, No. 2.
Nachemson et al., "Intravital wireless telemetry of axial forces in Harrington distraction rods in patients with idiopathic scoliosis.", The Journal of Bone and Joint Surgery, 1971, pp. 445-465, 53, No. 3.
Nachlas et al., "The cure of experimental scoliosis by directed growth control.", The Journal of Bone and Joint Surgery, 1951, pp. 24-34, 33-A, No. 1.
Newton et al., "Fusionless scoliosis correction by anterolateral tethering . . . can it work ?. ", 39th Annual Scoliosis Research Society Meeting, 2004.
Oh et al., "Bone transport over an intramedullary nail for reconstruction of long bone defects in tibia.", Archives of Orthopaedic and Trauma Surgery, 2008, pp. 801-808, 128, No. 8.
Ozcivici et al., "Mechanical signals as anabolic agents in bone.", Nature Reviews Rheumatology, 2010, pp. 50-59, 6, No. 1.
Piorkowski et al., Preventing Port Site Inversion in Laparoscopic Adjustable Gastric Banding, Surgery for Obesity and Related Diseases, 2007, 3(2), pp. 159-162, Elsevier; New York, U.S.A.
Prontes, "Longest bone in body.", eHow.com, 2012.
Rathjen et al., "Clinical and radiographic results after implant removal in idiopathic scoliosis.", SPINE, 2007, pp. 2184-2188, 32, No. 20.
Ren et al., "Laparoscopic adjustable gastric banding: Surgical technique", Journal of Laparoendoscopic & Advanced Surgical Techniques, 2003, pp. 257-263, 13, No. 4.
Reyes-Sanchez et al., "External fixation for dynamic correction of severe scoliosis", The Spine Journal, 2005, pp. 418-426, 5, No. 4.

Rinsky et al., "Segmental instrumentation without fusion in children with progressive scoliosis.", Journal of Pediatric Orthopedics, 1985, pp. 687-690, 5, No. 6.
Rode et al., "A simple way to adjust bands under radiologic control", Obesity Surgery, 2006, p. 418, 16, No. 4.
Schmerling et al., "Using the shape recovery of nitinol in the Harrington rod treatment of scoliosis.", Journal of Biomedical Materials Research, 1976, pp. 879-892, 10, No. 6.
Scott et al., "Transgastric, transcolonic and transvaginal cholecystectomy using magnetically anchored instruments.", SAGES Annual Scientific Sessions, Poster Abstracts, Apr. 18-22, 2007, P511, p. 306.
Sharke, "The machinery of life", Mechanical Engineering Magazine, Feb. 2004, Printed from Internet site Oct. 24, 2007 http://www.memagazine.org/contents/current/features/moflife/moflife.html.
Shiha et al., "Ilizarov gradual correction of genu varum deformity in adults.", Acta Orthop Belg, 2009, pp. 784-791, 75, No. 6.
Simpson et al., "Femoral lengthening with the intramedullary skeletal kinetic distractor.", Journal of Bone and Joint Surgery, 2009, pp. 955-961, 91-B, No. 7.
Smith, "The use of growth-sparing instrumentation in pediatric spinal deformity.", Orthopedic Clinics of North America, 2007, pp. 547-552, 38, No. 4.
Soubeiran et al. "The Phenix M System, a fully implanted non-invasive lengthening device externally controllable through the skin with a palm size permanent magnet. Applications in limb salvage." International Society of Limb Salvage 14th International Symposium on Limb Salvage, Sep. 13, 2007, Hamburg, Germany. (2 pages).
Soubeiran et al., "The Phenix M System. A fully implanted lengthening device externally controllable through the skin with a palm size permanent magnet; Applications to pediatric orthopaedics", 6th European Research Conference in Pediatric Orthopaedics, Oct. 6, 2006, Toulouse, France (7 pages).
Stokes et al., "Reducing radiation exposure in early-onset scoliosis surgery patients: Novel use of ultrasonography to measure lengthening in magnetically-controlled growing rods. Prospective validation study and assessment of clinical algorithm", 20th International Meeting on Advanced Spine Techniques, Jul. 11, 2013. Vancouver, Canada. Scoliosis Research Society.
Sun et al., "Masticatory mechanics of a mandibular distraction osteogenesis site: Interfragmentary micromovement.", Bone, 2007, pp. 188-196, 41, No. 2.
Synthes Spine, "VEPTR II. Vertical Expandable Prosthetic Titanium Rib II: Technique Guide.", 2008, 40 pgs.
Synthes Spine, "VEPTR Vertical Expandable Prosthetic Titanium Rib, Patient Guide.", 2005, 26 pgs.
Takaso et al., "New remote-controlled growing-rod spinal instrumentation possibly applicable for scoliosis in young children.", Journal of Orthopaedic Science, 1998, pp. 336-340, 3, No. 6.
Teli et al., "Measurement of forces generated during distraction of growing rods.", Journal of Children's Orthopaedics, 2007, pp. 257-258, 1, No. 4.
Tello, "Harrington instrumentation without arthrodesis and consecutive distraction program for young children with severe spinal deformities: Experience and technical details.", The Orthopedic Clinics of North America, 1994, pp. 333-351, 25, No. 2.
Thaller et al., "Limb lengthening with fully implantable magnetically actuated mechanical nails (PHENIX®)—Preliminary results.", Injury, 2014 (E-published Oct. 28, 2013), pp. S60-S65, 45.
Thompson et al., "Early onset scoliosis: Future directions", 2007, J Bone Joint Surg Am, pp. 163-166, 89-A, Suppl 1.
Thompson et al., "Growing rod techniques in early-onset scoliosis", Journal of Pediatric Orthopedics, 2007, pp. 354-361, 27, No. 3.
Thonse et al., "Limb lengthening with a fully implantable, telescopic, intramedullary nail.", Operative Techniques in Orthopedics, 2005, pp. 355-362, 15, No. 4.
Trias et al., "Dynamic loads experienced in correction of idiopathic scoliosis using two types of Harrington rods.", SPINE, 1979, pp. 228-235, 4, No. 3.
Verkerke et al., "An extendable modular endoprosthetic system for bone tumor management in the leg", Journal of Biomedical Engineering, 1990, pp. 91-96, 12, No. 2.

(56) References Cited

OTHER PUBLICATIONS

Verkerke et al., "Design of a lengthening element for a modular femur endoprosthetic system", Proceedings of the Institution of Mechanical Engineers Part H: Journal of Engineering in Medicine, 1989, pp. 97-102, 203, No. 2.

Verkerke et al., "Development and test of an extendable endoprosthesis for bone reconstruction in the leg.", The International Journal of Artificial Organs, 1994, pp. 155-162, 17, No. 3.

Weiner et al., "Initial clinical experience with telemetrically adjustable gastric banding", Surgical Technology International, 2005, pp. 63-69, 15.

Wenger, "Spine jack operation in the correction of scoliotic deformity: A direct intrathoracic attack to straighten the laterally bent spine: Preliminary report", Arch Surg, 1961, pp. 123-132 (901-910), 83, No. 6.

White, III et al., "The clinical biomechanics of scoliosis.", Clinical Orthopaedics and Related Research, 1976, pp. 100-112, 118.

Yonnet, "A new type of permanent magnet coupling.", IEEE Transactions on Magnetics, 1981, pp. 2991-2993, 17, No. 6.

Yonnet, "Passive magnetic bearings with permanent magnets.", IEEE Transactions on Magnetics, 1978, pp. 803-805, 14, No. 5.

Zheng et al., "Force and torque characteristics for magnetically driven blood pump.", Journal of Magnetism and Magnetic Materials, 2002, pp. 292-302, 241, No. 2.

\* cited by examiner

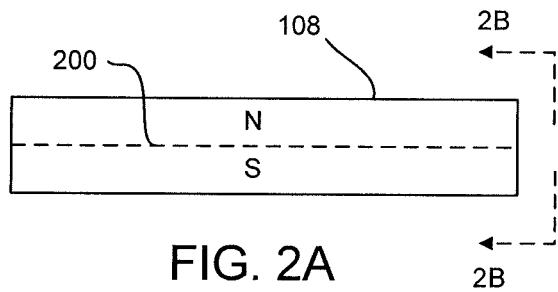 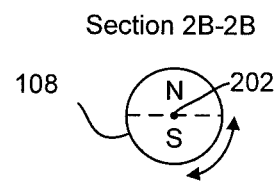
FIG. 2A  FIG. 2B
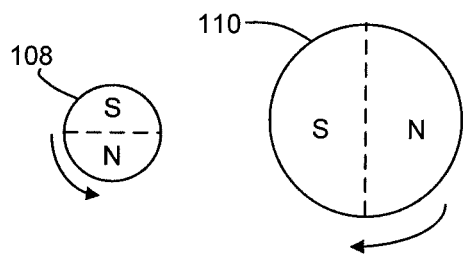 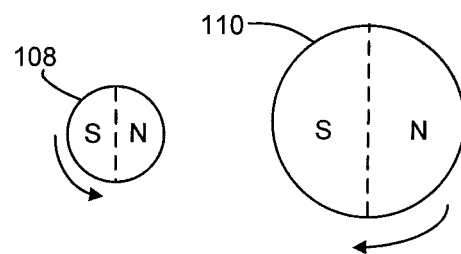
FIG. 3A  FIG. 3B
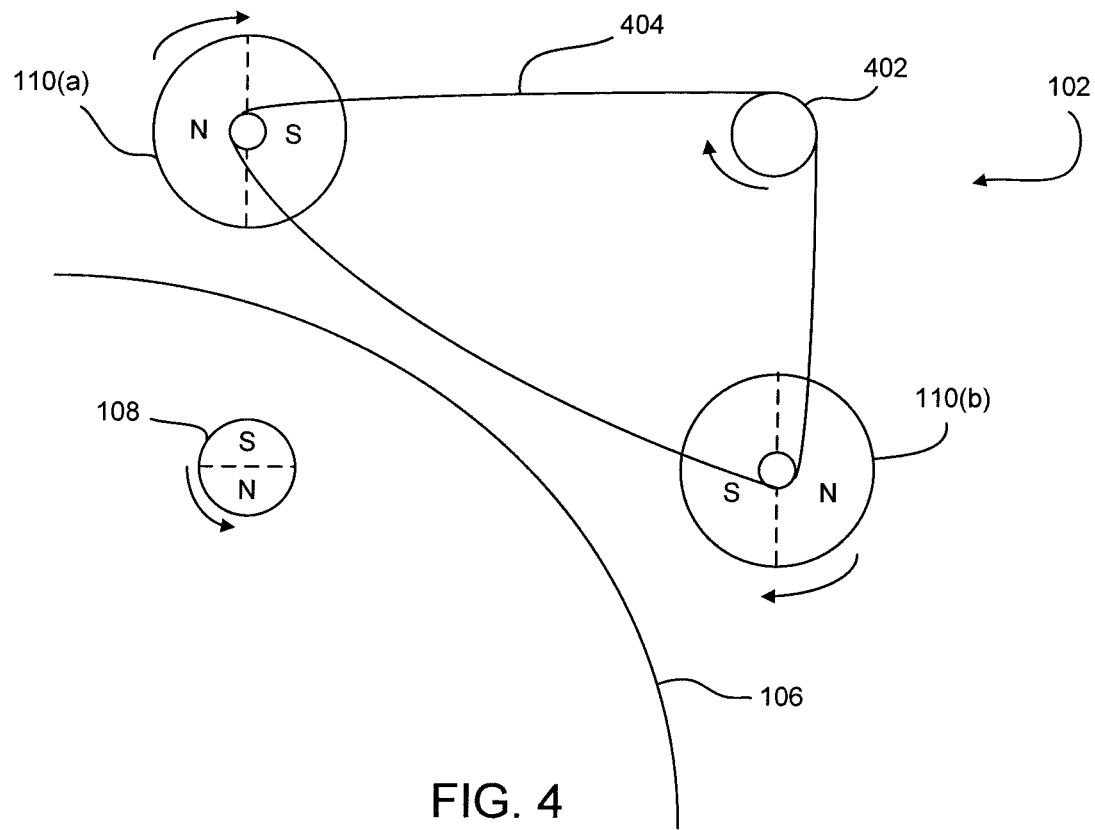
FIG. 4

ADJUSTABLE IMPLANT SYSTEM

RELATED APPLICATIONS

The present patent application is a continuation of co-pending U.S. patent application Ser. No. 16/103,710, filed Aug. 14, 2018, which is a continuation of U.S. patent application Ser. No. 14/885,749, filed Oct. 16, 2015 (now U.S. Pat. No. 10,076,413), which is a continuation of U.S. patent application Ser. No. 13/625,725, filed Sep. 24, 2012 (now U.S. Pat. No. 9,198,755), which a continuation of U.S. patent application Ser. No. 12/411,107, filed Mar. 25, 2009 (now abandoned), which claims the benefit of U.S. Provisional Patent Application No. 61/039,349, filed Mar. 25, 2008. Each of the foregoing is incorporated by reference in its entirety as though fully set forth herein.

TECHNICAL FIELD

This application is related to annuloplasty rings. More specifically, this application is related to reversibly adjustable annuloplasty rings.

BACKGROUND

Heart disease and its associated health issues are a large concern today. Mitral valve defects such as regurgitation are often caused by a dilation of the tissue surrounding the valve. This causes the mitral opening to enlarge, which prevents the valve leaflets from sealing properly. This heart condition is commonly treated by sewing a ridged ring around the valve. Cinching the tissue around the ring restores the valve opening to its approximate original size and operating efficiency.

The proper degree of cinching, however, is difficult to determine during open heart surgery. This is because the patient is under general anesthesia, in a prone position, with the chest wide open, and a large incision in the heart. These factors and others affect the ability to test the modified annulus for its therapeutic effect upon mitral valve leaflet coaptation. Even if the cinching is done well, the tissue may continue to change over the patient's lifetime such that the heart condition returns.

SUMMARY

In one embodiment, a system for treating a heart valve includes an adjustable annuloplasty ring configured to be attached to or near a cardiac valve annulus. The adjustable annuloplasty ring includes a tubular body member and one or more adjustable members. The tubular body member and the one or more adjustable members form a ring shape. The adjustable annuloplasty ring also includes an internal magnet within the tubular body member. The internal magnet is configured to rotate in response to a rotating external magnetic field. The internal magnet is coupled to the one or more adjustable members to change a dimension of the ring shape as the internal magnet rotates.

In certain embodiment the internal magnet includes a cylindrical magnet having magnetic poles divided along a plane running the length of the cylinder. Similar external magnets may be used in an external adjustment device that generates the external magnetic field. The internal and external magnets may be permanent magnets. In addition, or in other embodiments, one or more electromagnets may be used. Numerous example embodiments are provided for the adjustable annuloplasty ring and the external adjustment device.

In certain embodiments, a magnetic brake is implanted near a patient's heart. In the absence of the external magnetic field, the magnetic brake prevents the internal magnet from rotating. In the presence the external magnetic field, the magnetic brake allows the internal magnet to rotate.

Additional aspects and advantages will be apparent from the following detailed description of preferred embodiments, which proceeds with reference to the accompanying drawings.

BRIEF DESCRIPTION OF THE DRAWINGS

FIGS. 2A and 2B schematically illustrate a magnet that is usable in the annuloplasty ring shown in FIG. 1A according to one embodiment.

FIGS. 3A and 3B schematically illustrate an end view of the magnet of the external magnetic adjustment device placed in parallel with the magnet of the annuloplasty ring according to certain embodiments.

FIG. 4 is a schematic diagram of an external magnet adjustment device including two magnets arranged outside of a patient's body according to one embodiment.

DETAILED DESCRIPTION OF ILLUSTRATED EMBODIMENTS

An adjustable annuloplasty ring allows for the proper degree of cinching both during open heart surgery and over the patient's lifetime. In one embodiment, an annuloplasty ring may be adjusted less-invasively or non-invasively with the patient alert and postoperatively healed. In addition, the annuloplasty ring incorporates the ability to both open and close with fine position control.

The embodiments disclosed herein are generally directed to adjustable annuloplasty rings for mitral valve repair. However, this disclosure is not limited to the mitral valve and an artisan will recognize from the disclosure herein that the adjustable rings may be adapted for other heart valves (e.g., tricuspid valve, aortic value, and/or pulmonary valve) and other vascular structures.

Overview

Figure 1A:
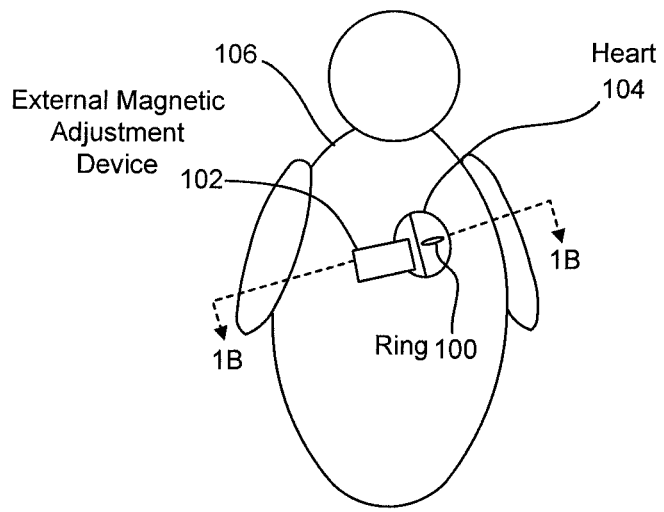
FIG. 1A is a block diagram of a system for adjusting the size of a heart valve according to one embodiment that includes an annuloplasty ring and an external magnetic driver or adjustment device.
Figure 1B:
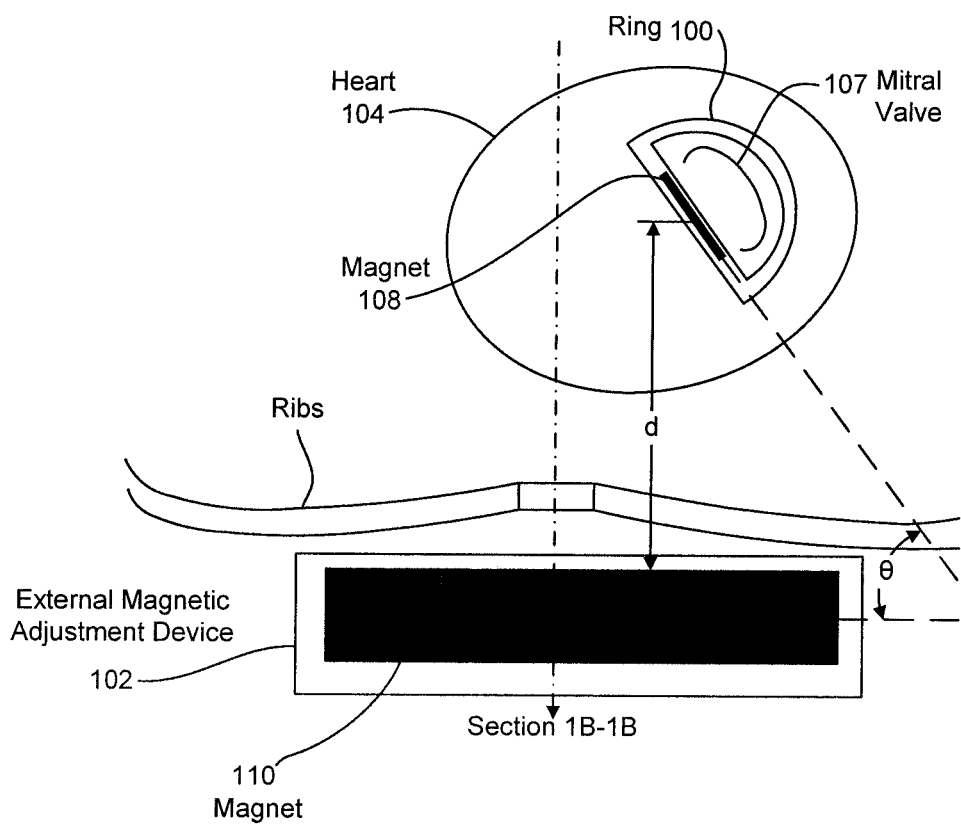
FIG. 1B is an enlarged, cross-sectional view of the annuloplasty ring and the external magnetic adjustment device shown in FIG. 1A according to one embodiment.

FIG. 1A is a block diagram of a system for adjusting the size of a heart valve according to one embodiment that includes an annuloplasty ring 100 and an external magnetic driver or adjustment device 102. For illustrative purposes, FIG. 1B is an enlarged, cross-sectional view of the annuloplasty ring 100 and the external magnetic adjustment device 102 shown in FIG. 1A. The adjustable annuloplasty ring 100 may be implanted in a heart 104 of a patient 106 in the same manner as current rigid annuloplasty rings. Although the heart 104 discussed herein is described in terms of a human heart, an artisan will understand from the disclosure herein that the patient 106 may include any type of mammal or other animal. The annuloplasty ring 100 in this example is "D" shaped and may be attached, for example, to the mitral valve 107. However, an artisan will recognize from the disclosure herein that other shapes (e.g., circular or "C" shaped rings) may also be used for other openings (e.g., for the tricuspid valve).

The annuloplasty ring 100 includes a permanent magnet 108 that may be rotated remotely by one or more magnets 110 in the external magnetic adjustment device 102. Rotating the one or more magnets 110 in the external magnetic adjustment device 102 in one direction causes the annuloplasty ring 100 to close while turning the one or more magnets 110 in the opposite direction causes the annuloplasty ring 100 to open. The external magnetic adjustment device 102 shown in FIGS. 1A and 1B may include an external handpiece that controls the annuloplasty ring 100 from outside of the patient's body at a distance d from the annuloplasty ring 100. However, other adjustment devices (including percutaneous adjustment devices) will also be described in detail below.

In one embodiment, the annuloplasty ring 100 and adjustment device includes one or more of the magnetic adjustment elements disclosed in U.S. Patent Application Publication No. 2008/0097487, titled "Method and Apparatus for Adjusting a Gastrointestinal Restriction Device," filed Jun. 8, 2007, which is assigned to the Assignee of the present application, and which is hereby incorporated by reference herein for all purposes. U.S. Patent Application Publication No. 2008/0097487 discloses a gastrointestinal implant system that includes a magnetically adjustable restriction device having a contact surface configured for at least partially engaging a surface of a gastrointestinal tract of a mammal. The gastrointestinal implant system includes an implantable interface including a driving element, the driving element being moveable and operatively coupled to the adjustable restriction device by an actuator configured to change the dimension or configuration of the contact surface in response to movement of the driving element. Movement of the driving element is effected by application of a moving magnetic field originating external to the patient.

FIGS. 2A and 2B schematically illustrate a magnet 108 that is usable in the annuloplasty ring 100 shown in FIG. 1A according to one embodiment. A similarly configured magnet may also be used for the magnet 110 in the external magnetic adjustment device 102. The magnet 108 in this example embodiment is cylindrical and has magnetic poles (e.g., north "N" and south "S") divided along a plane 200 that runs the length of the cylinder. A rotating magnetic field causes the magnet 108 to rotate around an axis 202 of the cylinder that passes through the respective centers of the cylinder's bases (the "cylindrical axis").

For example, FIGS. 3A and 3B schematically illustrate an end view of the magnet 110 of the external magnetic adjustment device 102 placed in parallel with the magnet 108 of the annuloplasty ring 100 according to certain embodiments. For illustrative purposes, FIG. 3A illustrates the magnets 108, 110 aligned for maximum (peak) torque transmission and FIG. 3B illustrates the south pole of the magnet 110 of the external magnetic adjustment device 102 aligned with the north pole of the magnet 108 of the annuloplasty ring 100. Regardless of a current or initial alignment of the magnets 108, 110, the magnetic fields of the respective magnets 108, 110 interact with each other such that mechanically rotating the magnet 110 (e.g., using a stepper motor) in the external magnetic adjustment device 102 causes the magnet 108 in the annuloplasty ring 100 to rotate. For example, rotating the magnet 110 in a clockwise direction around its cylindrical axis causes the magnet 108 to rotate in a counterclockwise direction around its cylindrical axis. Similarly, rotating the magnet 110 in a counterclockwise direction around its cylindrical axis causes the ma net 108 to rotate in a clockwise direction around its cylindrical axis.

The magnet 110 in the external magnetic adjustment device 102 provides accurate one-to-one control of the magnet 108 in the annuloplasty ring 100, assuming sufficient magnetic interaction between the magnets 108, 110. In other words, one complete rotation of the magnet 110 in the external magnetic adjustment device 102 will cause one complete rotation of the magnet 108 in the annuloplasty ring 100. If the relationship between the number of rotations of the magnet 108 and the size of the ring is linear, the size of the annuloplasty ring 108 may be determined directly from the number of revolutions since the ring was at its last known size. If, however, the relationship between the number of revolutions and ring size is not linear, a look-up table based on tested values for a particular ring or type of ring may be used to relate the number of revolutions to the size of the annuloplasty ring 100. Imaging techniques may also be used to determine the ring size after it is implanted in the patient. In addition, or in other embodiments, the annuloplasty ring 100 may include circuitry for counting the number of revolutions or determining its own size, and for communicating this data to a user. For example, the annuloplasty ring 100 may include a radio frequency identification (RF ID) tag technology to power and receive data from the annuloplasty ring 100.

While placing the magnets 108, 110 in parallel increases rotational torque on the magnet 108 in the annuloplasty ring 100, the disclosure herein is not so limited. For example, FIG. 1B illustrates that the cylindrical axis of the magnet 110 in the external magnetic adjustment device 102 may be located at an angle θ with respect to the cylindrical axis of the magnet 108 in the annuloplasty ring 100. The rotational torque on the magnet 108 provided by rotating the magnet 110 increases as the angle θ approaches zero degrees, and decreases as the angle θ approaches 90 degrees (assuming both magnets 108, 110 are in the same geometric plane or in parallel planes).

The rotational torque on the magnet 108 in the annuloplasty ring 100 also increases by using magnets 108, 110 with stronger magnetic fields and/or by increasing the number of magnets used in the external magnetic adjustment device 102. For example, FIG. 4 is a schematic diagram of an external magnetic adjustment device including two magnets 110(a), 110(b) arranged outside of a patient's body 106 according to one embodiment. An artisan will recognize from the disclosure herein that the external magnetic adjustment device 102 is not limited to one or two magnets, but may include any number of magnets. For example, an example embodiment that includes four magnets is described below with respect to FIG. 28. The magnets 110(a), 110(b) are oriented and rotated relative to each other such that their magnetic fields add together at the ring magnet 108 to increase rotational torque. A computer controlled motor 402 synchronously rotates the external magnets 110(a), 110(b) through a mechanical linkage 404 to magnetically rotate the internal magnet 108 and adjust the size of the annuloplasty ring 100. One revolution of the motor 402 causes one revolution of the external magnets 110(a), 110(b), which in turn causes one revolution of the ring magnet 108. As discussed above, by counting motor revolutions, the size of the annuloplasty ring 100 may be calculated. In one embodiment, the motor 402 includes a gearbox with a known gear ratio such that multiple motor revolutions may be counted for one magnet revolution.

In another embodiment, a strong electro-magnetic field like that used in Magnetic Resonance Imaging (MRI) is used to adjust the annuloplasty ring 100. The magnetic field may be rotated either mechanically or electronically to cause the magnet 108 in the annuloplasty ring 100 to rotate. The patient's body may also be rotated about the axis 202 of the magnet 108 in the presence of a strong magnetic field, like that of an MRI. In such an embodiment, the strong magnetic field will hold the magnet 108 stationary while the ring 100 and patient 106 are rotated around the fixed magnet 108 to cause adjustment. The ring size may be determined by counting the number of revolutions of the magnetic field, or the patient's body, similar to counting revolutions of the permanent magnets 110 discussed above.

In another embodiment, the annuloplasty ring 100 may be adjusted during open heart surgery. For example, after implanting the annuloplasty ring 100 in the heart 104, the heart 104 and pericardium may be closed, and the regurgitation monitored (e.g., using ultrasound color Doppler). Then, a user (e.g., surgeon) may use a handheld adjustment device 102 to resize the annuloplasty ring based on the detected regurgitation. Additional regurgitation monitoring and ring adjustment may be performed before completing the surgery.

Figure 5A:
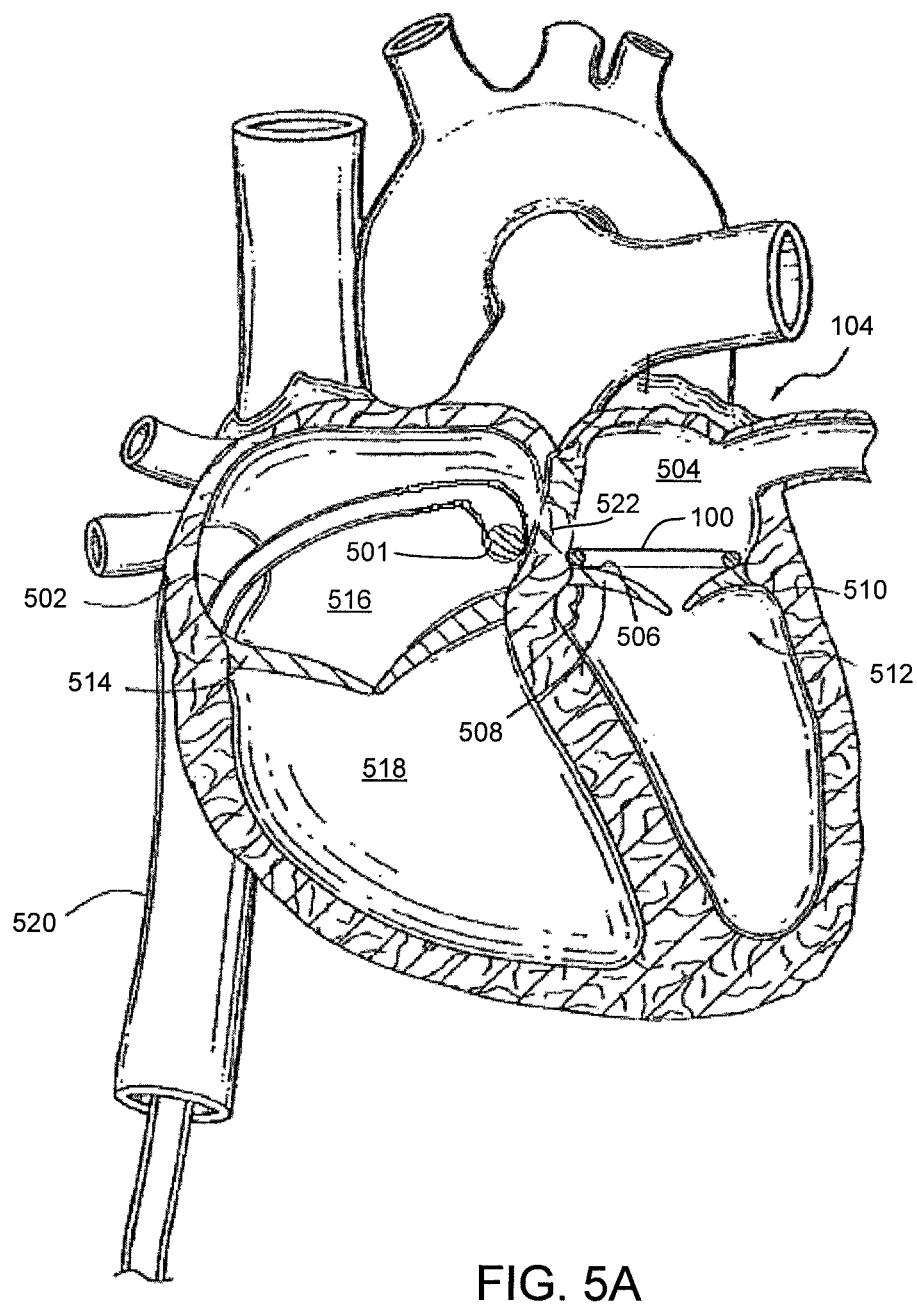
FIGS. 5A and 5B schematically illustrate a catheter system used to insert an adjustment device into a patient's heart according to certain embodiments.
Figure 5B:
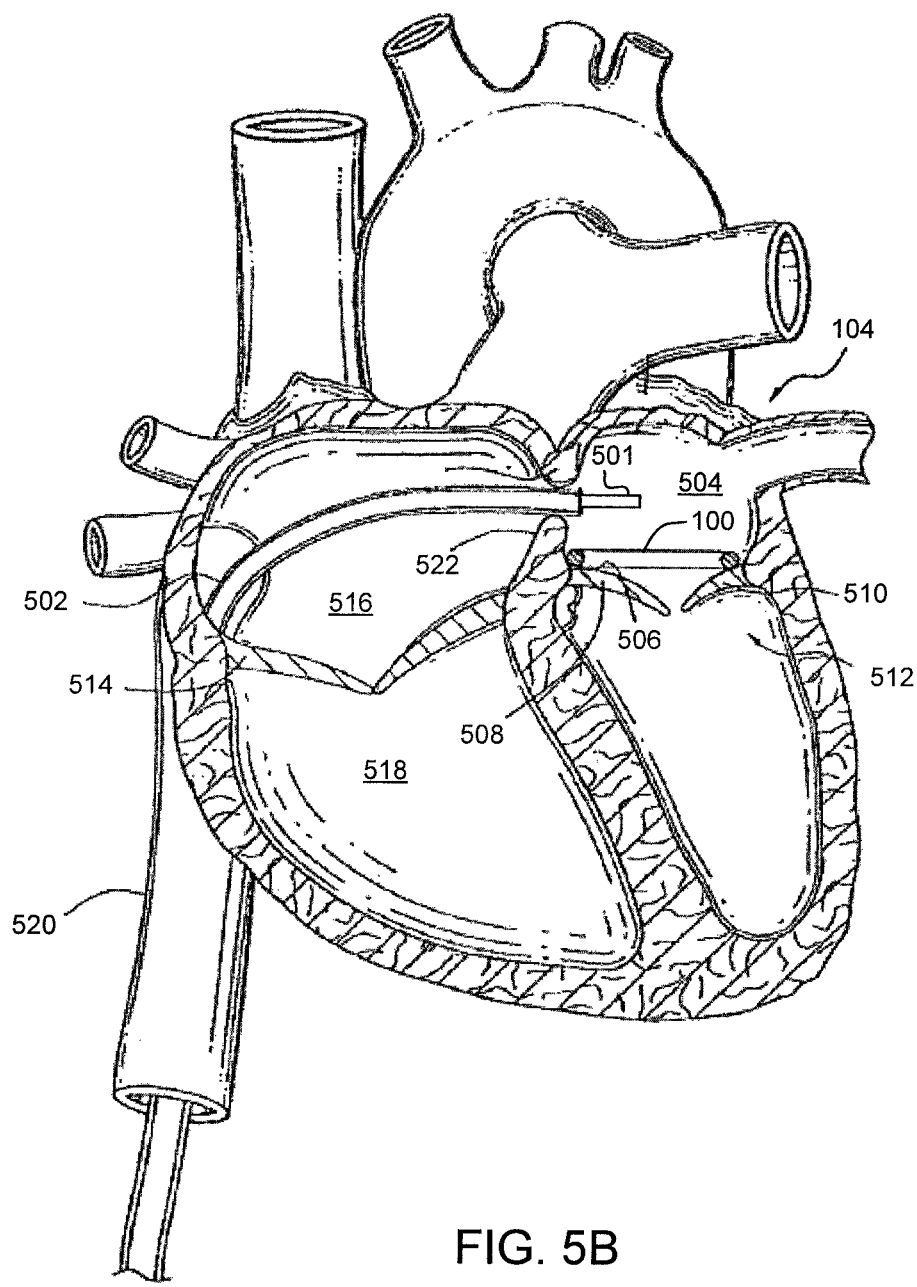

In another embodiment, a percutaneously delivered adjustment device is used to resize the annuloplasty ring 100. For example, FIGS. 5A and 5B schematically illustrate a catheter system 502 used to insert an adjustment device 501 into a patient's heart 104 according to certain embodiments. As shown, the annuloplasty ring 100 may be implanted in the left atrium 504 of the heart 104 on the upper side 506 of the leaflets 508 of the mitral valve 510. However, it is contemplated that the annuloplasty ring 100 may be positioned on the lower side of the leaflets 508. For example, the annuloplasty ring 100 may be positioned in the left ventricle 512. In some non-limiting embodiments, the annuloplasty ring 100 is snaked through the chordae tendineae and then placed against the lower surfaces of the leaflets 508. Alternatively, the chordae tendineae may be cut to provide a delivery path for implantation of the annuloplasty ring 100. In certain embodiments, the annuloplasty ring 100 may be implanted at other locations in the vasculature system, or at any other position within a patient's body 106. For example, the annuloplasty ring 100 may be implanted at a location proximate to the tricuspid valve 514. The annuloplasty ring 100 may be positioned on the upper side (e.g., in the right atrium 516) or lower side (e.g., in the right ventricle 518) of the tricuspid valve 514 to improve the efficacy of the tricuspid valve 514.

As shown in FIG. 5A, the catheter system 502 enters the heart 104 through the inferior vena cava 520 into the right atrium 516 so as to position the adjustment device 501 proximate the interatrial septum 522. The catheter system 502 may alternatively enter from the superior vena cava. As discussed above, the adjustment device 501 includes one or more magnets configured to interact with a magnetic field of a magnet in the annuloplasty ring 100. The catheter system 502 is configured to adjust the size of the annuloplasty ring 100 through the interatrial septum 522 by rotating the one or more magnets in the adjustment device 501 using a flexible drive shaft connected to an external hand crank operated by a user (e.g., physician) or a processor-controlled motor.

As shown in FIG. 5B, the catheter system 502 in another embodiment may enter the heart 104 through the inferior vena cava 520 into the right atrium 516, and through a hole (e.g., through the fossa ovalis) in the interatrial septum 522 into the left atrium 504. The catheter system 502 may alternatively enter from the superior vera cava. Although not shown in FIG. 5B, the catheter system 502 may locate the adjustment device 501 proximate the magnet in the annuloplasty ring 100. As discussed above, the adjustment device 501 includes one or more magnets configured to interact with a magnetic field of the magnet in the annuloplasty ring 100. The catheter system 502 is configured to adjust the size of the annuloplasty ring 100 by rotating the one or more magnets in the adjustment device 501 using a flexible drive shaft connected to an external hand crank operated by a user (e.g., physician) or a processor controlled motor.

Figure 6:
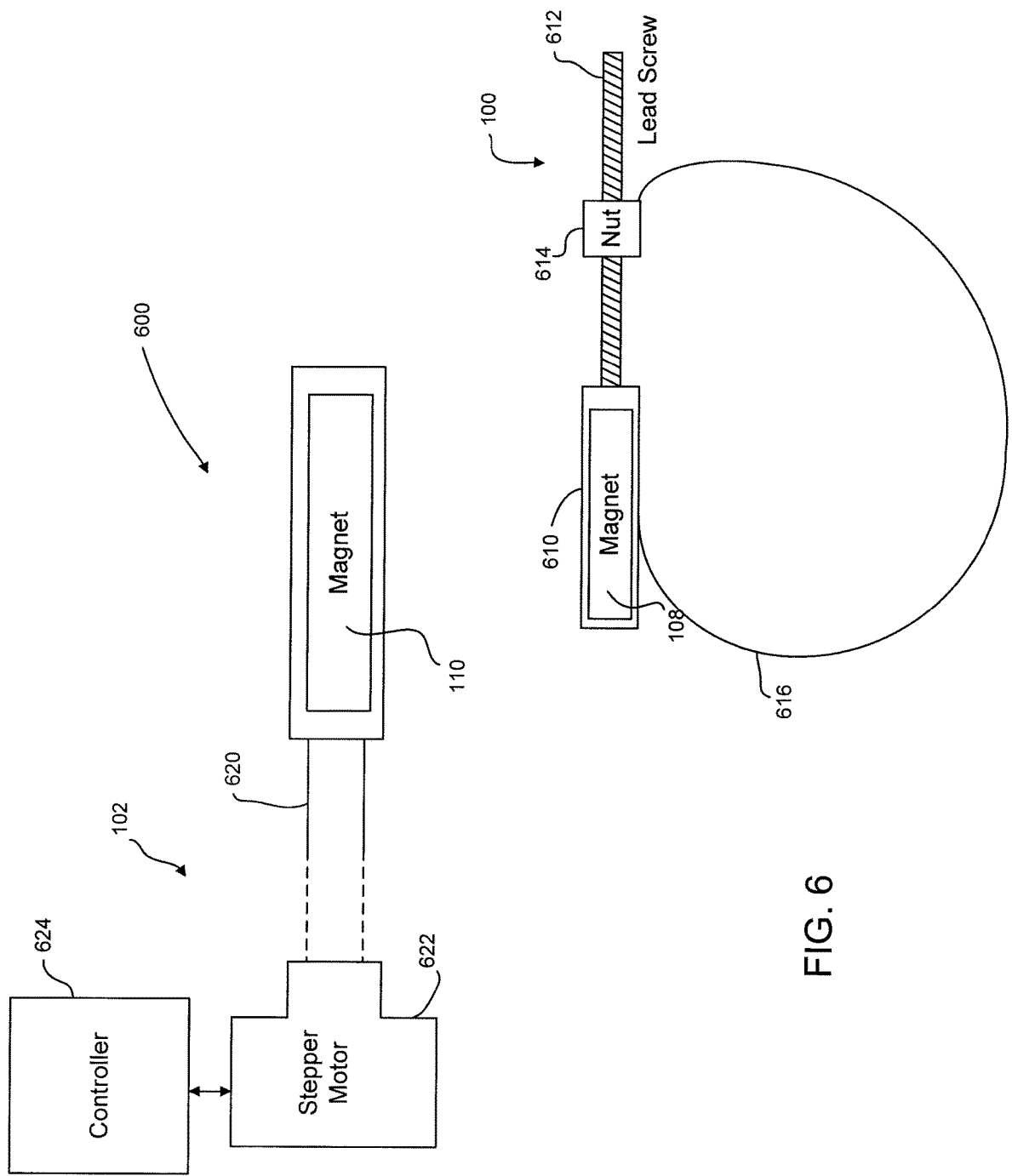
FIG. 6 is a simplified block diagram of a system for adjusting the size of a heart valve according to one embodiment.

FIG. 6 is a simplified block diagram of a system 600 for adjusting the size of a heart valve according to one embodiment. The simplified embodiment shown in FIG. 6 is provided to illustrate the basic operation of the annuloplasty ring 100. However, more detailed embodiments are provided below.

The system 600 includes an adjustable annuloplasty ring 100 and an external magnetic adjustment device 102. The annuloplasty ring 100 includes a magnet 108 in a magnet housing 610. The magnet 108 is cylindrical and is configured to rotate around its cylindrical axis when exposed to a rotating magnetic field. The magnet 108 is coupled to a proximal end of a lead screw 612. A spindle nut 614 is threaded onto the lead screw 612. A wire 616 is coupled to the magnet housing 610 and the spindle nut 614 to form a loop. The wire 616 may include, for example, stainless steel or superelastic nitinol.

The external magnetic adjustment device 102 includes a magnet 110 in a magnet housing 618 coupled to a drive shaft 620. The drive shaft 620 may be connected to a stepper motor 622 coupled to a motor controller/drive 624. The controller/drive 624 may include, for example, a microprocessor or personal computer. The controller/drive 624 is configured to control the position, rotation direction, rotation speed, speed ramp up/down, and other parameters of the stepper motor 622. The stepper motor 622 rotates the shaft 620, which in turn rotates the magnet 110. As discussed above, in certain embodiments the shaft 620 and the magnet 110 may be covered with a protective material (e.g., plating) and inserted into the heart 104 through a catheter.

In operation, the rotating magnet 110 in the external magnetic adjustment device 102 causes the magnet 108 in the annuloplasty ring 100 to rotate. The notating magnet 108 causes the lead screw 612 to rotate, which in turn causes the spindle nut 614 to move along the threads of the lead screw 612 to either increase or decrease the size of the loop formed by the wire 616.

Figure 7:
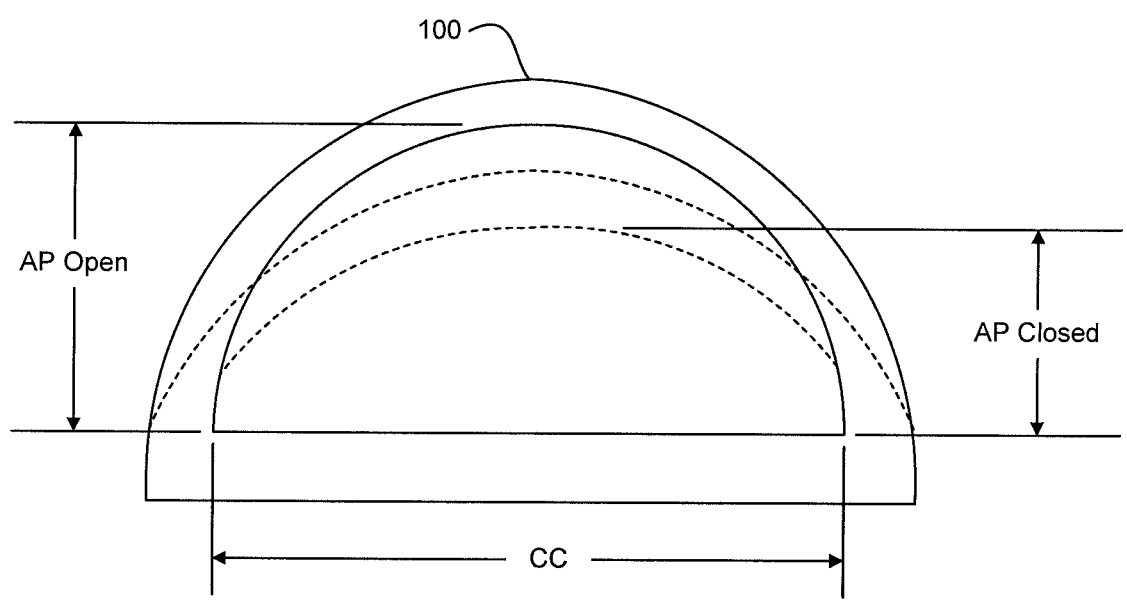
FIG. 7 is a schematic diagram of an adjustable annuloplasty ring according to one embodiment.

In certain embodiments, it is desirable to symmetrically adjust the size of the annuloplasty ring 100 in an anterior/posterior (AP) direction. For example, FIG. 7 is a schematic diagram of an adjustable annuloplasty ring according to one embodiment. The annuloplasty ring 100 is "D" shaped having an AP dimension along the curved portion of the "D" and a commissure to commissure or "CC" dimension along the straight portion of the "D." Adjusting the annuloplasty ring 100 from an open to a closed position, or vice versa, changes the AP dimension without substantially changing the CC dimension. Further, the AP dimension changes symmetrically in that both the left and right sides of the annuloplasty ring 100 change by substantially the same amount. Certain of the following embodiments include these features.

Example Annuloplasty Ring Embodiments

In certain embodiments discussed herein, including those discussed above as well as those discussed below, the materials of the annuloplasty ring 100 are selected for compatibility with long-term contact with human tissue. For example, these materials may include nitinol, stainless steel, titanium alloys, cobalt alloys, bio-compatible plastics, and other bio-compatible materials. In certain embodiments, the annuloplasty ring 100 may be covered with a polyester or Dacron® fabric or other suturable material. In addition or in other embodiments, the annuloplasty ring 100 may also include eyelets used for suturing. The magnet 108 discussed in certain embodiments herein may include a rare-earth magnet and may be plated (e.g., with nickel or gold) or encapsulated in a suitable bio-compatible material, such as the materials discussed above, to reduce or prevent harm to the patient and damage to the magnet. Bearings are included in certain embodiments. These bearings may be of any suitable type including, for example, ball bearings or jewel bearings.

Figure 8A:
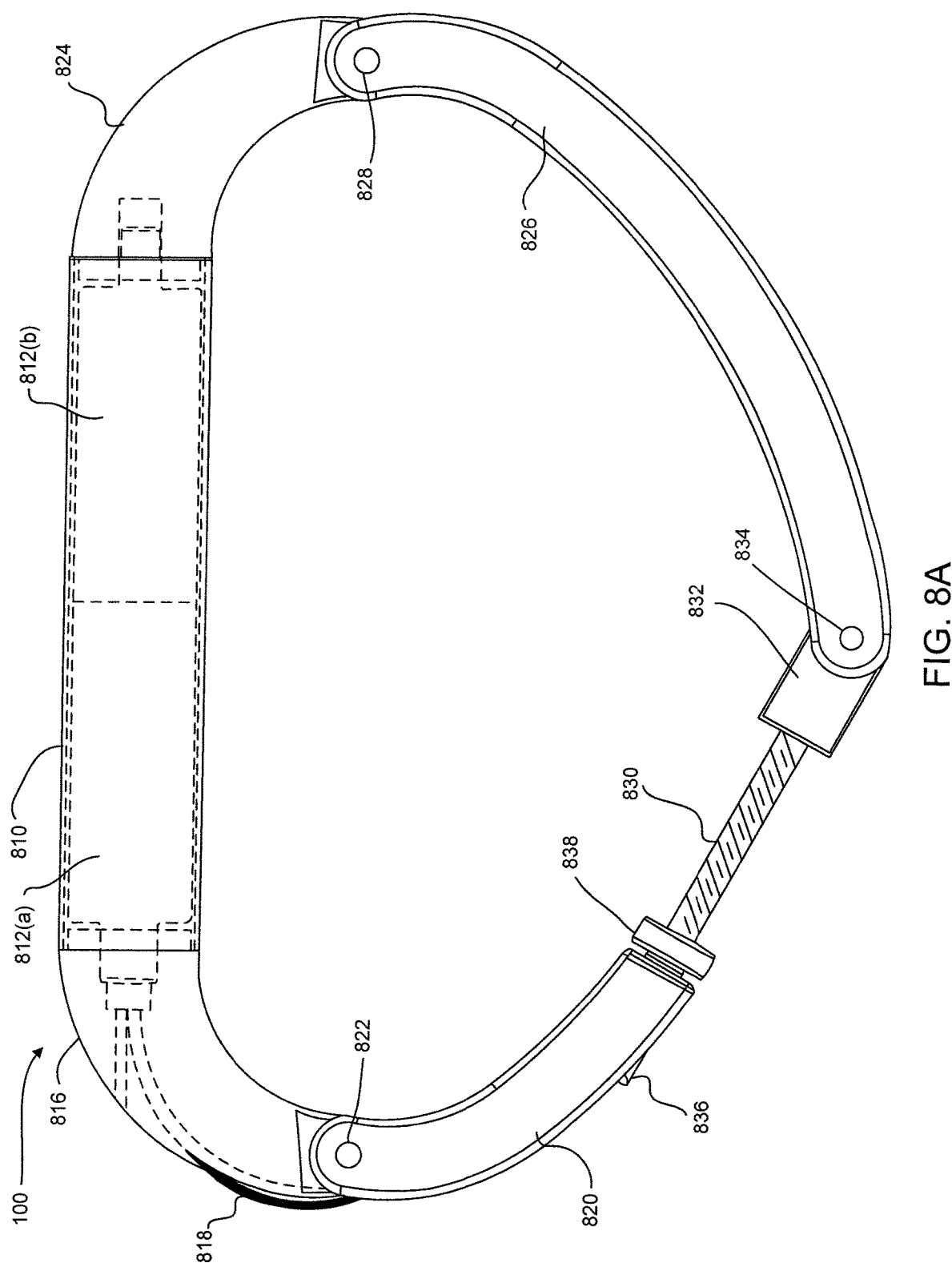
FIGS. 8A 8B, 8C 8D, and 8E schematically illustrate an annuloplasty ring according to one embodiment.
Figure 8B:
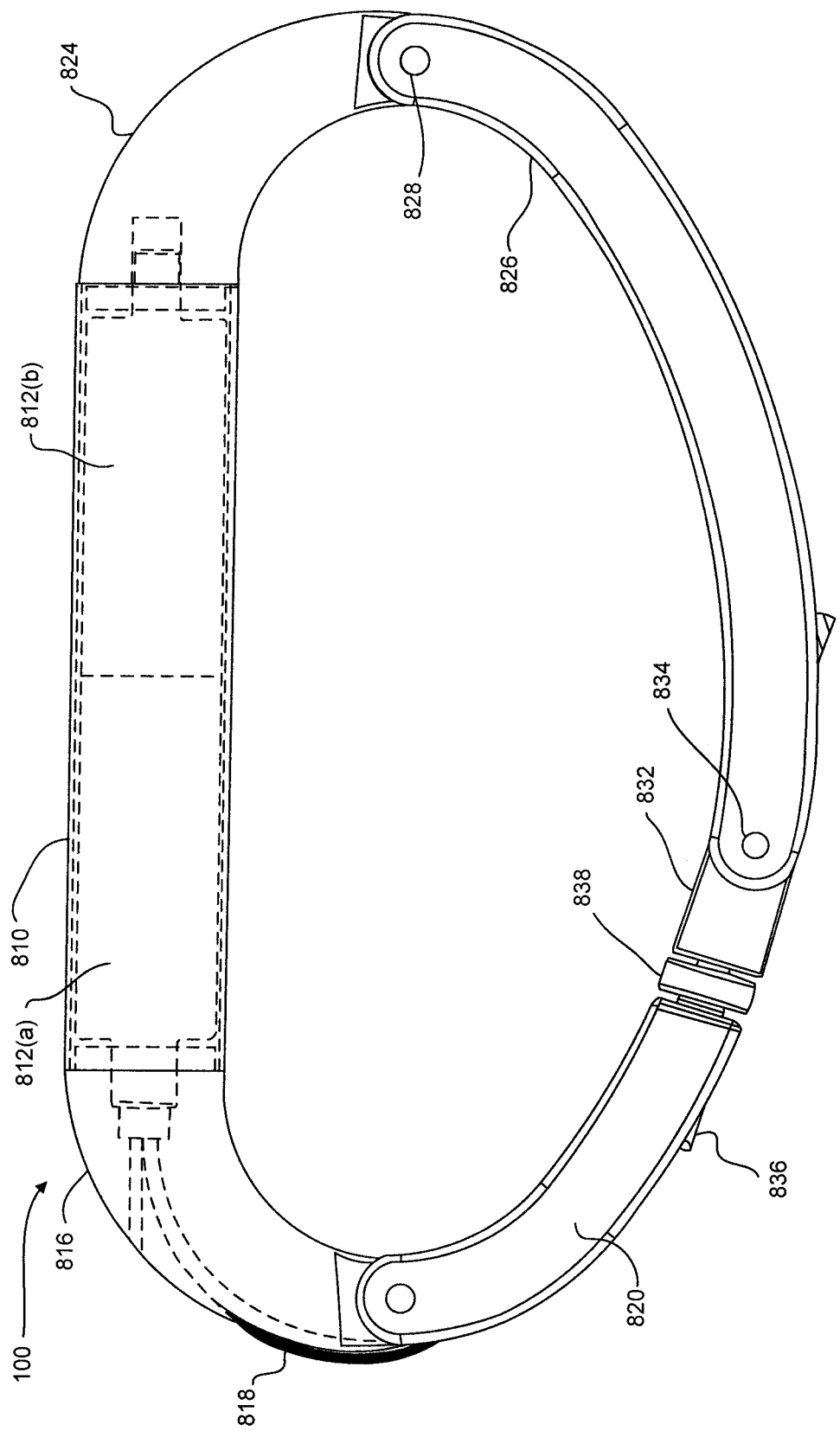
Figure 8C:
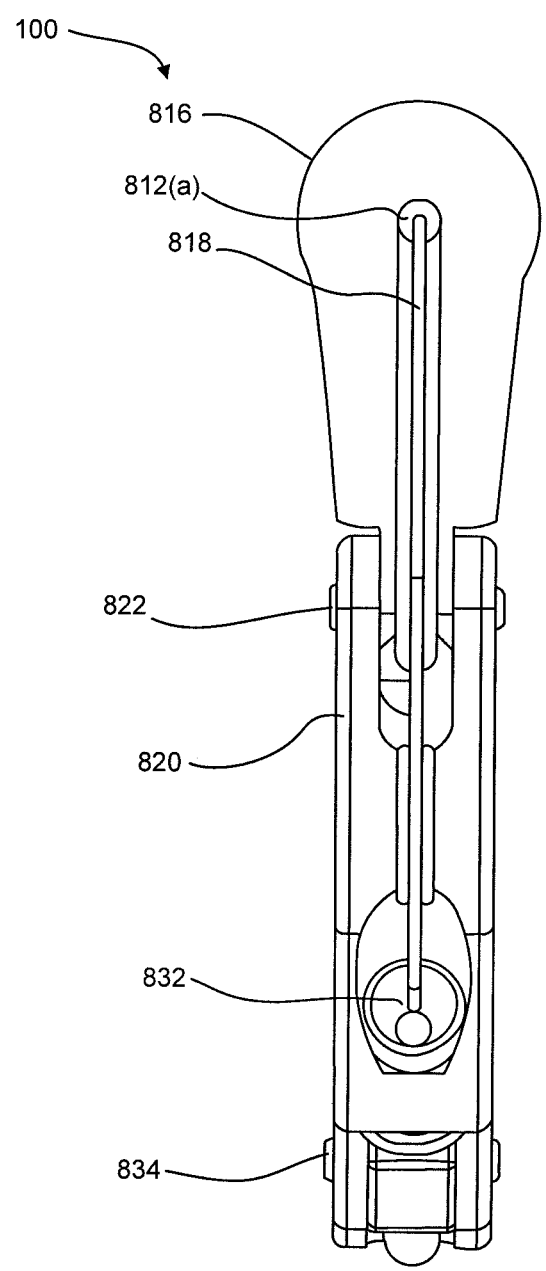
Figure 8D:
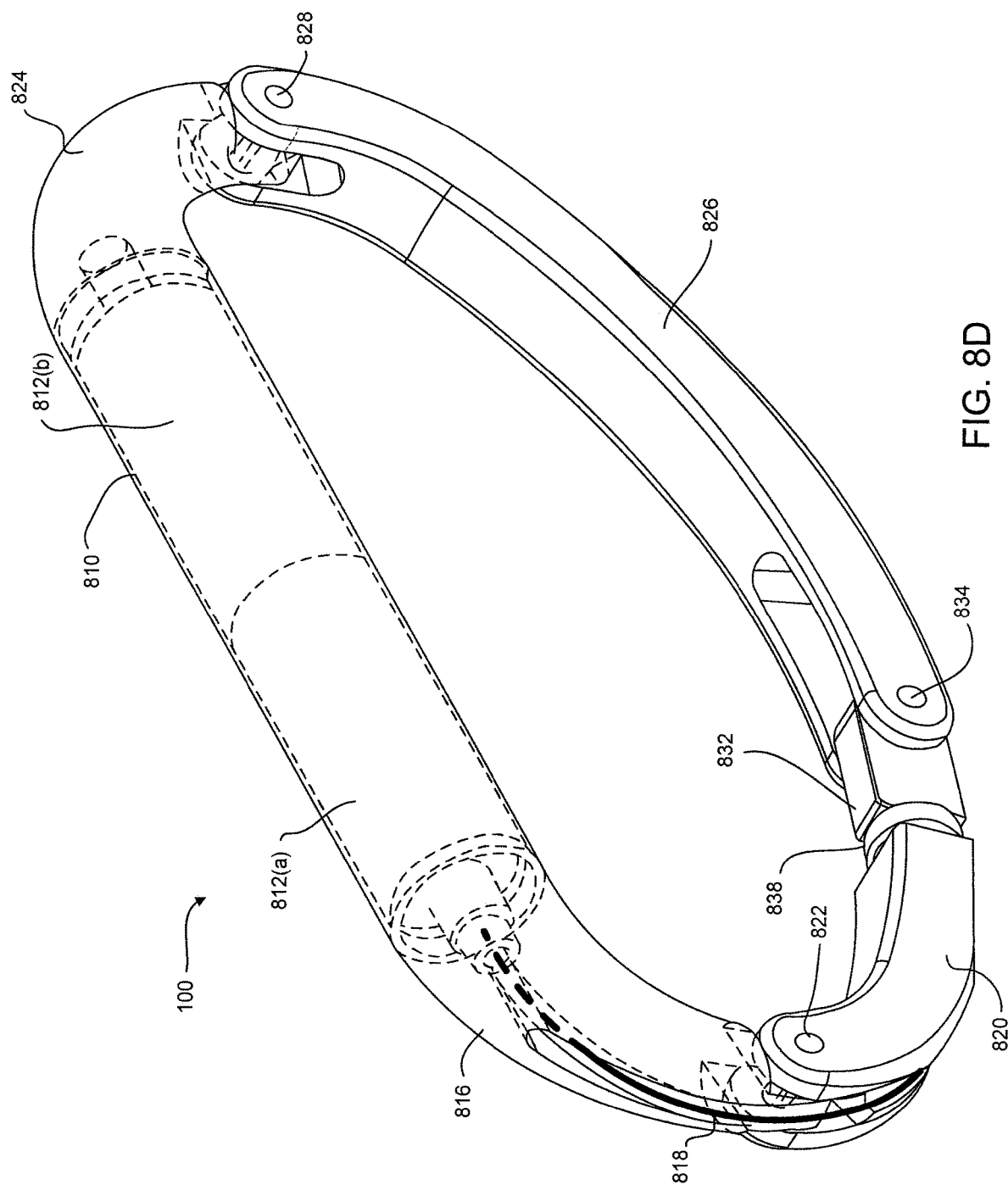
Figure 8E:
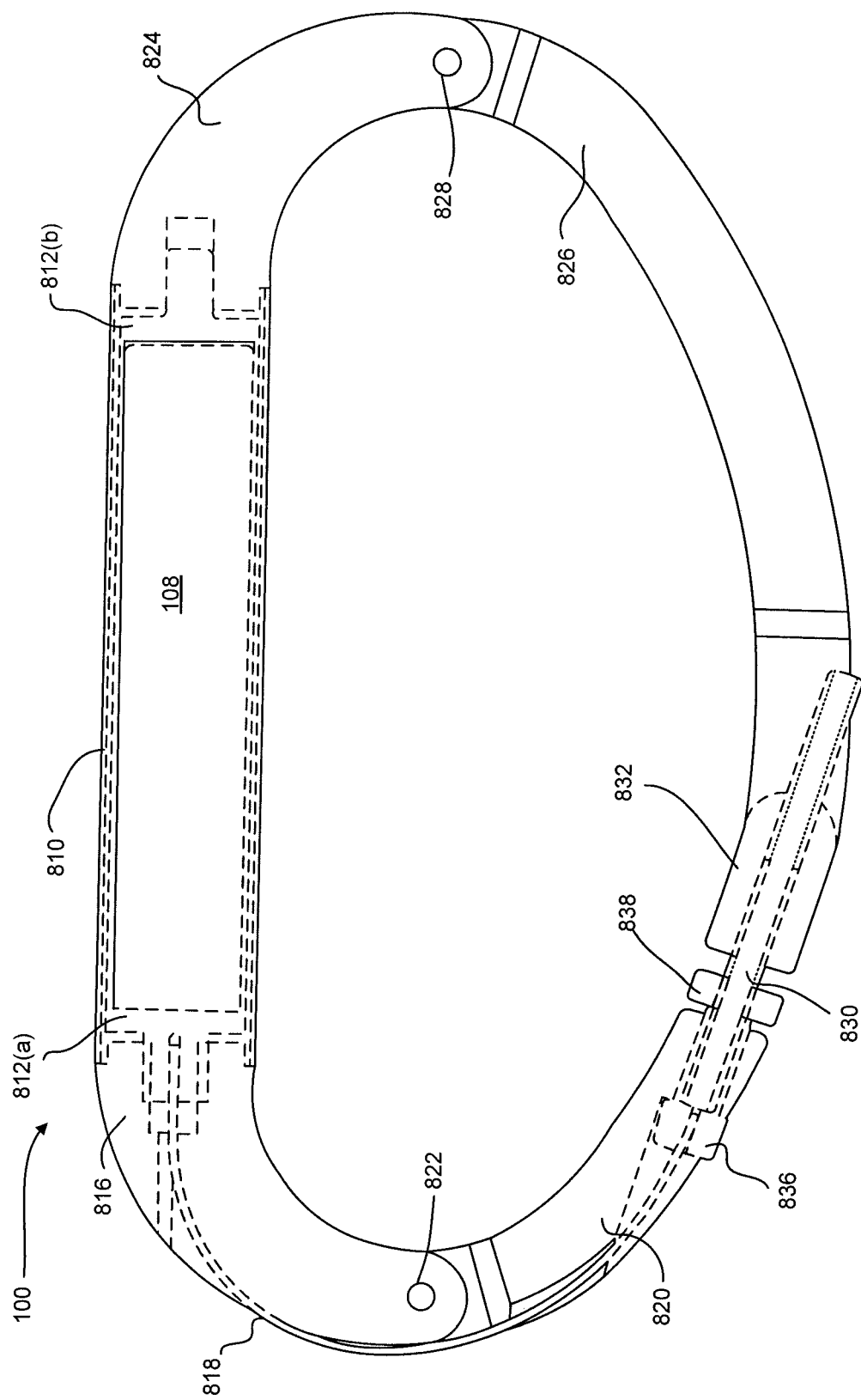

FIGS. 8A, 8B, 8C, 8D, and 8E schematically illustrate an annuloplasty ring 100 according to one embodiment. FIG. 8A is a partially transparent top view of the annuloplasty ring 100 in an AP extended or plus position. FIG. 8B is a partially transparent top view of the annuloplasty ring 100 in an AP retracted or minus position. FIG. 8C schematically illustrates a side view of the annuloplasty ring 100. FIG. 8D is a partially transparent perspective view of the annuloplasty ring 100. FIG. 8E is another partially transparent top view of the annuloplasty ring 100.

The annuloplasty ring 100 includes a body tube 810 for enclosing a magnet housing 812 (including a first end 812(a) and a second end 812(b)) that encases a magnet 108 (FIG. 8E). A first end of the body tube 810 is connected to a first fixed arm 816 and a first end of the magnet housing 812(a) crimps to a first end of a drive cable 818. The first fixed arm 816 is connected to a first swivel arm 820 at a first pin joint 822 (e.g., pivot point). A second end of the body tube 810 is connected to a second fixed arm 824 that is connected to a second swivel arm 826 at a second pin joint 828. The annuloplasty ring 100 also includes a lead screw 830 having a first end threaded into a drive nut 832 that is connected to the second swivel arm 826 at a third pin joint 834. A second end of the lead screw is connected to a drive spindle 836 that is connected to a second end of the drive cable 818. A spindle nut 838 is threaded onto the lead screw 830. The spindle nut 838 retains the drive spindle 836 into the first swivel arm 820.

The magnet housing 812 is engaged with the first fixed arm 816 and the second fixed arm 824 such that rotating the magnet 108 (e.g., using the external magnetic adjustment device 102) causes the magnet housing 812 to rotate. The rotating magnet housing 812 turns the drive cable 818, which turns the drive spindle 836. The drive spindle 836 rotates the lead screw 830 such that it screws into or out of the drive nut 832. As the lead screw 830 screws into or out of the drive nut 832, the swivel arms 820, 826 pivot at their respective pin joints 822, 828, 834 to reduce or enlarge the size of the ring opening in the AP dimension.

Figure 9:
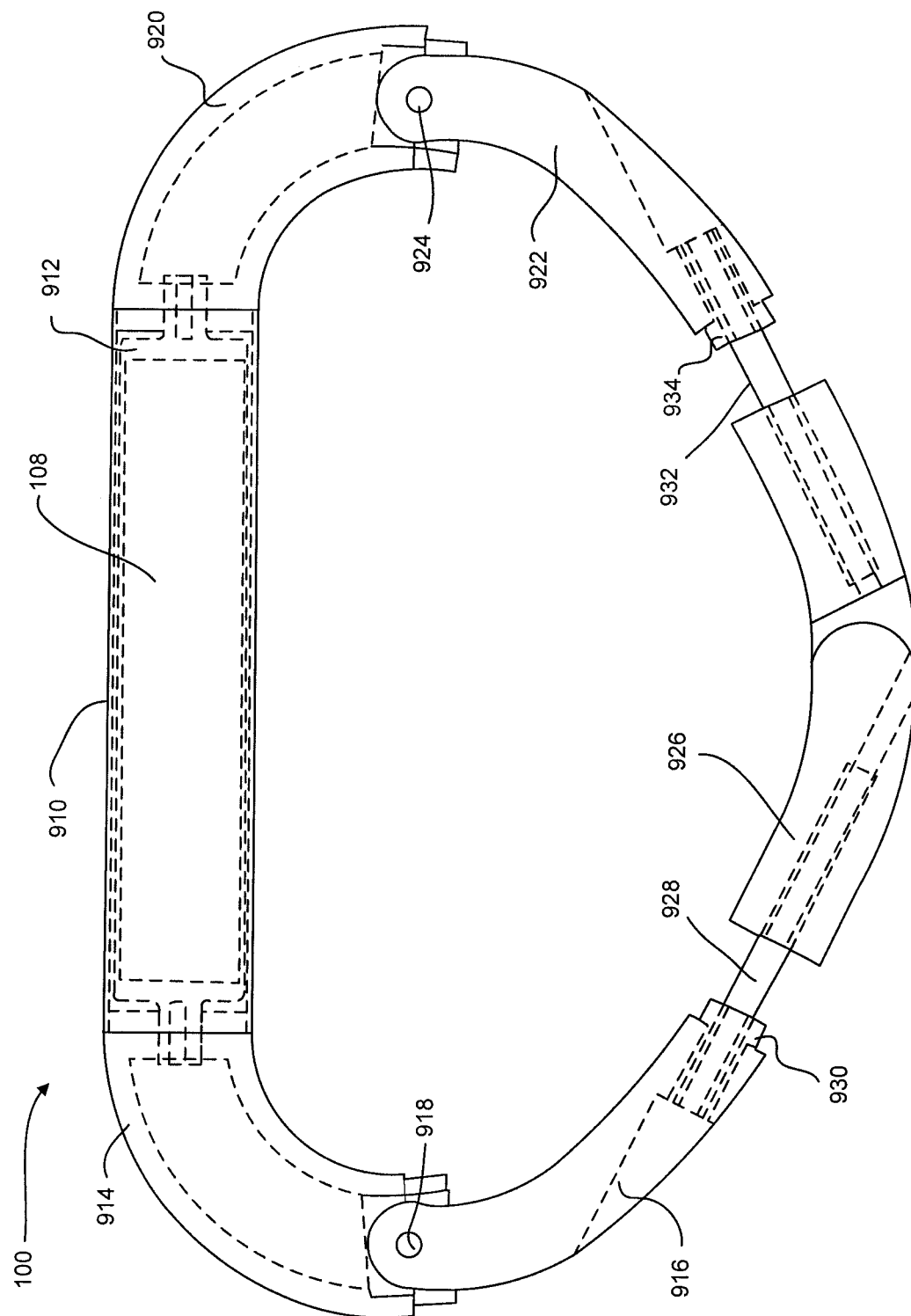
FIG. 9 is a schematic diagram illustrating a partially transparent top view of an annuloplasty ring according to another embodiment.

FIG. 9 is a schematic diagram illustrating a partially transparent top view of an annuloplasty ring 100 according to another embodiment. The annuloplasty ring 100 shown in FIG. 9 includes a body tube 910 for enclosing a magnet housing 912 that encases a magnet 108. A first end of the body tube 910 is connected to a first fixed arm 914 and a first end of the magnet housing 912 crimps to a first end of a first drive cable (not shown). The first fixed arm 914 is connected to a first swivel arm 916 at a first pin joint 918. A second end of the body tube 910 is connected to a second fixed arm 920 and a second end of the magnet housing 912 crimps to a first end of a second drive cable (not shown). The second fixed arm 920 is connected to a second swivel arm 922 at a second pin joint 924.

The annuloplasty ring 100 also includes an extension 926 that symmetrically moves in and out in the AP dimension as the magnet 108 turns. A first end of a first lead screw 928 is connected to the first swivel arm 916 through a first drive spindle 930 that is connected to the second end of the first drive cable. A second end of the first lead screw 928 is threaded into a first end of the extension 926. A first end of a second lead screw 932 is connected to the second swivel arm 922 through a second drive spindle 934 that is connected to the second end of the second drive cable. A second end of the second lead screw 932 is threaded into a second end of the extension 926. The extension 926 acts as a drive nut for a first lead screw 928 and the second lead screw 932. The first lead screw 928 and the second lead screw 932 both screw into or out of the extension 926 at the same time, causing the swivel arms 916, 922 to pivot about their respective pin joints 918, 924. In such an embodiment, one of the lead screws 928, 932 has "right handed" threads and the other has "left-handed" threads such that both lead screws 928, 932 tighten or loosen together.

Figure 10:
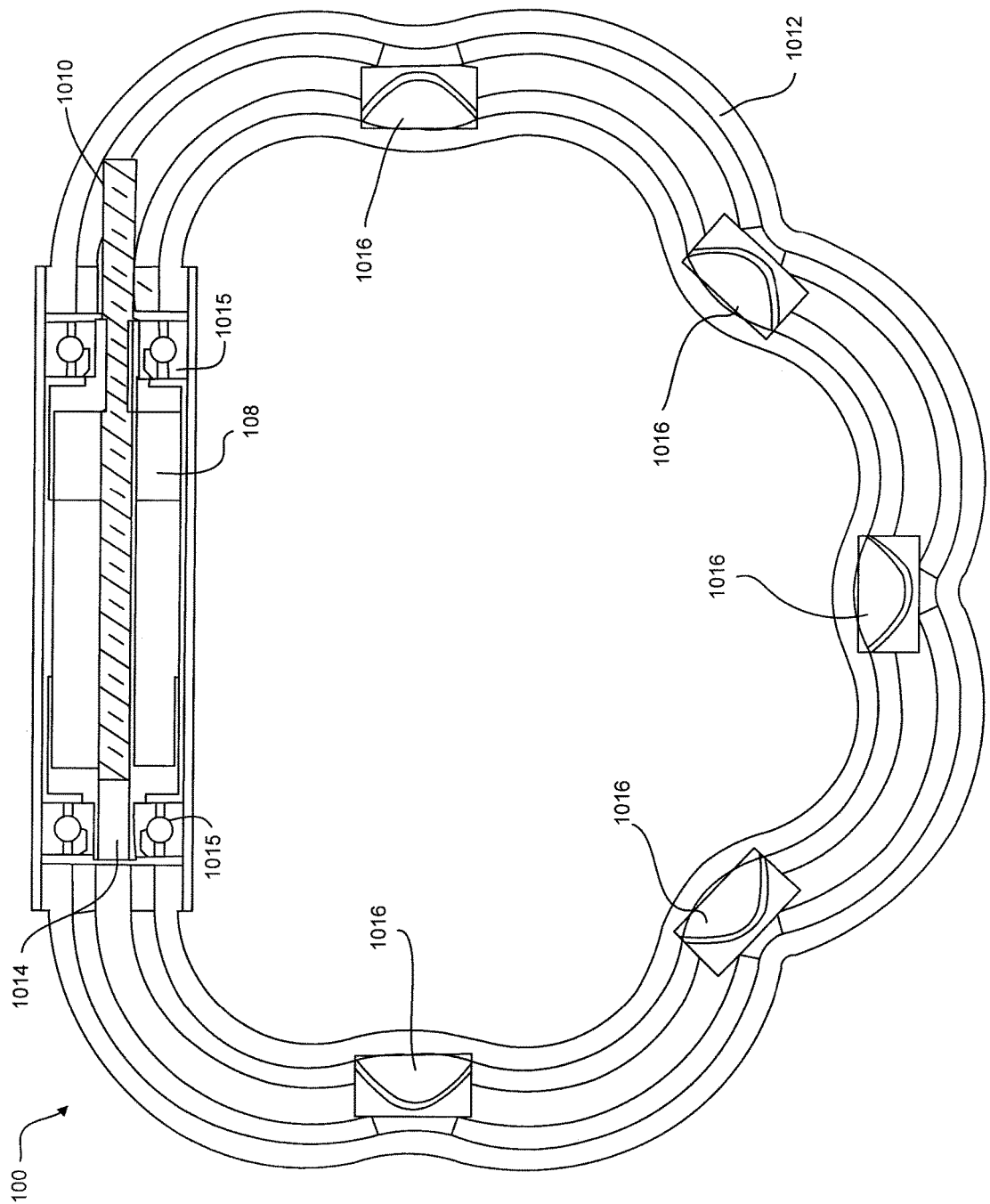
FIG. 10 is a schematic diagram illustrating a cross-sectional top view illustrating an annuloplasty ring according to another embodiment.

FIG. 10 is a schematic diagram illustrating a cross-sectional top view illustrating an annuloplasty ring 100 according to another embodiment. The annuloplasty ring 100 shown in FIG. 10 includes a magnet 108, a flexible lead screw 1010, an elastic covering 1012, and a wire (not shown) extending from a first end of the flexible lead screw 1010 to a fixed point. The elastic covering 1012 may include, for example, a biocompatible polymer such as, for instance, polyurethane silicone or a silicone-urethane copolymer. The magnet 108 includes a hollow passage 1014 and a threaded nut section 1015 or bearings through which the flexible lead screw 1010 passes (e.g., either to the right or to the left) as the magnet 108 turns. Turning the magnet 108 in one direction exerts force on the flexible lead screw 1010, which is transmitted to the wire, which in turn causes the elastic covering 1012 to contract inwardly at predetermined locations 1016. The contraction symmetrically reduces the ring opening. Rotating the magnet 108 in the opposite direction reverses the contraction.

Figure 11A:
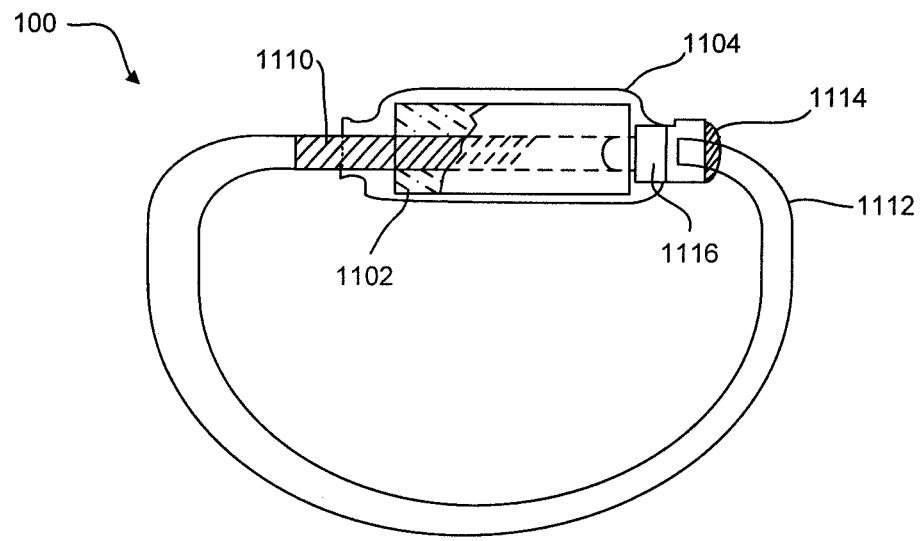
FIGS. 11A, 11B, and 11C are schematic diagrams of an adjustable annuloplasty ring according to another embodiment.
Figure 11B:
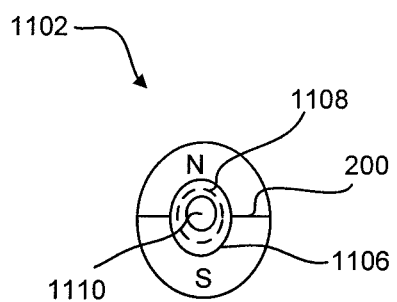
Figure 11C:
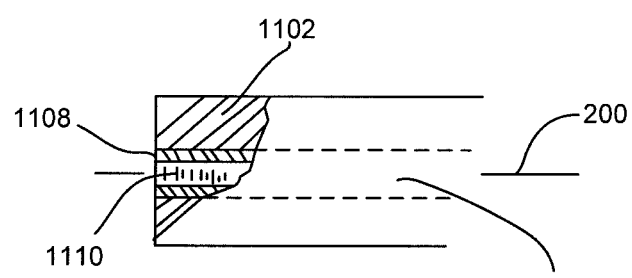

FIG. 11A is a schematic diagram of an adjustable annuloplasty ring 100 according to another embodiment. The annuloplasty ring 100 includes a permanent magnet 1102 configured to rotate within a magnet housing 1104. The magnet 1102 is cylindrical and is configured to rotate around its cylindrical axis when exposed to a rotating magnetic field. FIG. 11B is a schematic diagram of a front view of the magnet 1102 shown in FIG. 11A according to one embodiment. FIG. 11C is a schematic diagram of a side view of the magnet 1102 shown in FIG. 11A according to one embodiment. Like the magnet 108 shown in FIGS. 2A, 2B, 4, and 6, the magnet 1102 has magnetic poles (e.g., north "N" and south "S") divided along the plane 200 that runs the length of the cylinder. The magnet 1102 may include a rare earth magnet and may be plated (e.g., with nickel or gold) and/or suitably encapsulated to prevent harm to the patient and damage to the magnet 1102. Unlike the magnet 108 shown in FIGS. 2A, 2B, 4, and 6, however, the magnet 1102 includes a hollow region 1106 running along the length of the cylinder between the N and S pores. The hollow region 1106 may be threaded or may contain a threaded insert 1108 through which a lead screw 1110 is pulled into and out of the magnet 1102.

A wire 1112 is coupled between the magnet housing 1104 (e.g., by a weld 1114) and an end of the lead, screw 1110. In another embodiment, a separate lead screw 1110 is not used. Rather, threads are formed or cut into the end of the wire 1112 such that the wire 1112 interfaces directly with the threads in the magnet 1102 (e.g., the threaded insert 1108). The wire 1112 may include, for example, superelastic.

In one embodiment, the annuloplasty ring 100 includes bearings 1116 to anchor the spinning magnet 1102. When the magnet 1102 is exposed to a rotating magnetic field in one direction, the magnet 1102 pulls the lead screw 1110 and/or threaded wire 1112 into the magnet 1102, which in turn reduces the size of the loop formed by the wire 1112. When the magnet 1102 is exposed to the magnetic field rotating in the opposite direction, the magnet 1102 pushes the lead screw 1110 and/or the threaded wire 1112 out of the magnet 1102, which in turn increases the size of the loop formed by the wire 1112.

Figure 12A:
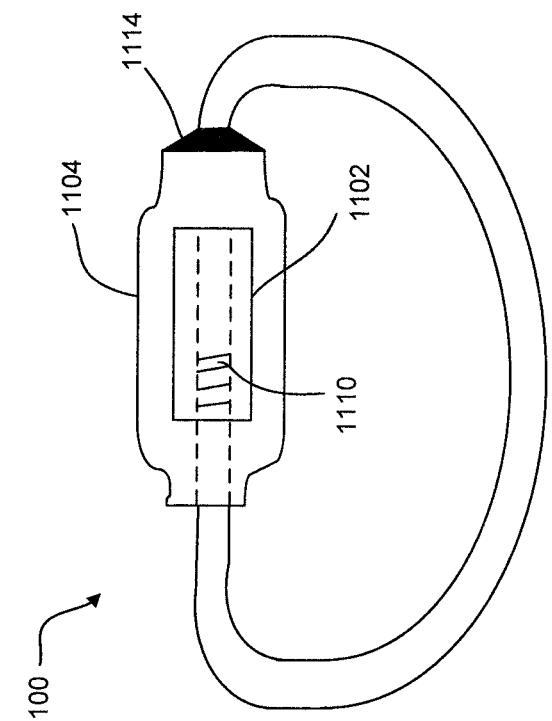
FIGS. 12A and 12B partially illustrate the annuloplasty ring shown in FIG. 11A in a retracted position (FIG. 12A) and in an expanded position (FIG. 12B) according to certain embodiments.
Figure 12B:
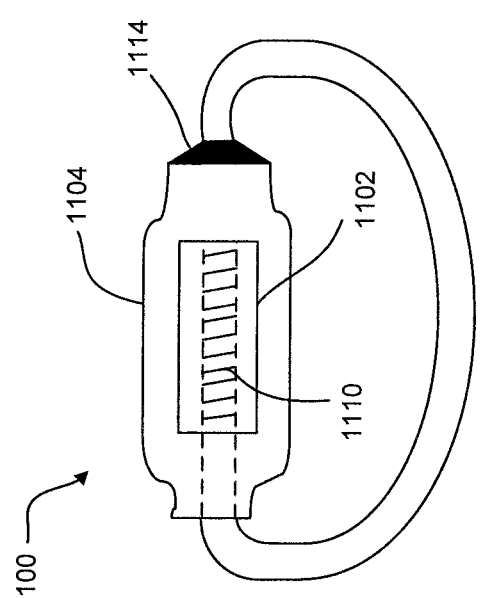

FIGS. 12A and 12B partially illustrate the annuloplasty ring 100 shown in FIG. 11A in a retracted position (FIG. 12A) and in an expanded position (FIG. 12B) according to certain embodiments. In FIG. 12A, the rotation of the magnet 1102 (e.g., clockwise) pulls the lead screw 1110 and/or threaded wire 1112 further into the magnet 1102 and the magnet housing 1104. In FIG. 12B, the rotation of the magnet 1102 (e.g., counter-clockwise) pushes the lead screw 1110 and/or threaded wire 1112 further out of the magnet 1102 and the magnet housing 1104. In one embodiment, a portion of the lead screw 1110 and/or the threads in the wire 1112 may extend beyond the magnet housing 1104 when the annuloplasty ring 100 is in the extended position. In another embodiment, the lead screw 1110 and/or the threads in the wire 1112 remain within the magnet housing 1104 in both the extended and retracted positions. Moving the lead screw 1110 and or the threaded portion of the threads in the wire 1112 into and out of the magnet 1110 allows improved control for symmetrically adjusting the annuloplasty ring 100 in the AP direction, as discussed above in relation to FIG. 7.

Figure 13A:
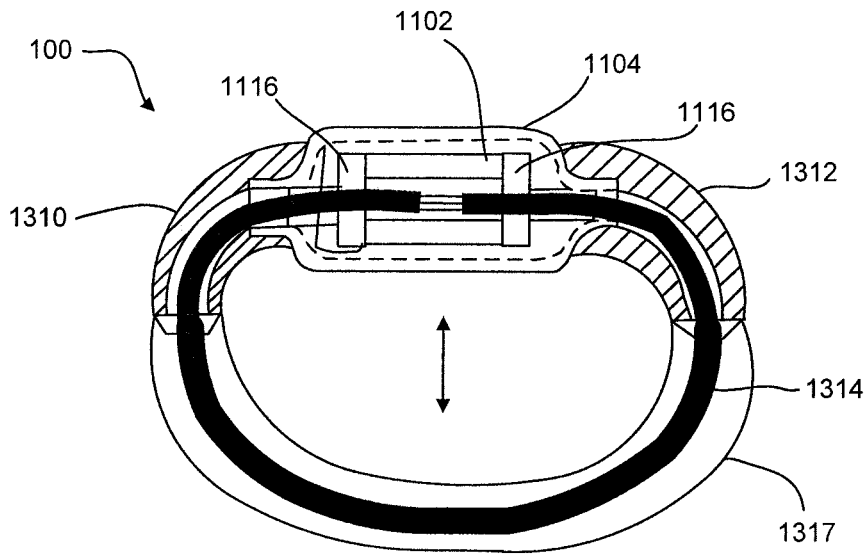
FIGS. 13A, 13B, and 13C are schematic diagrams of an adjustable annuloplasty ring according to another embodiment.
Figure 13B:
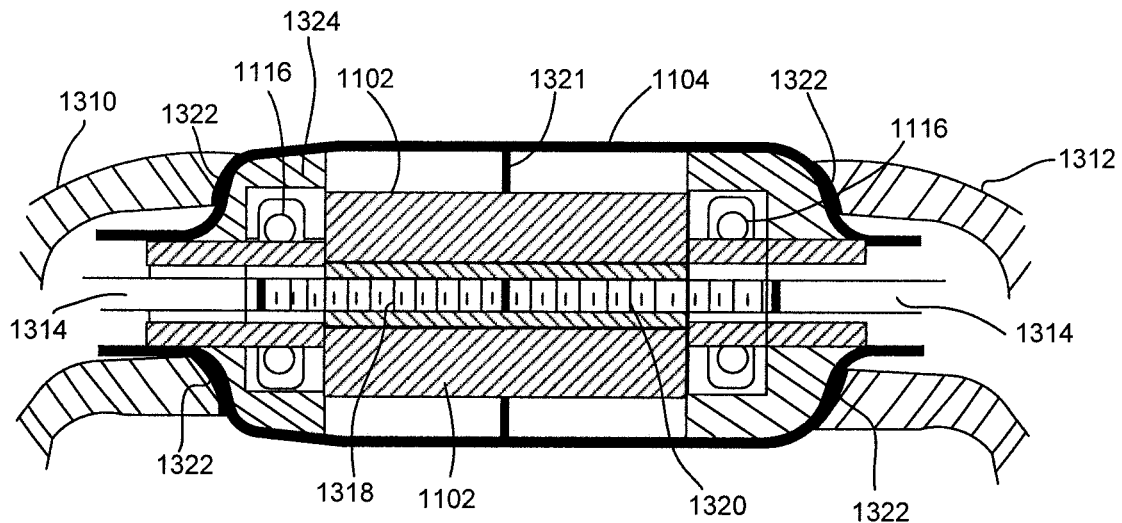
Figure 13C:
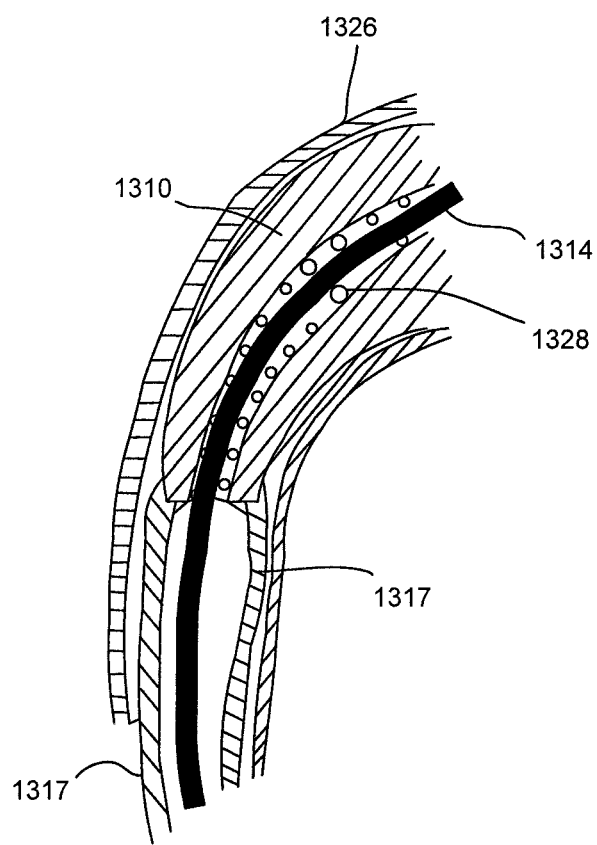

FIGS. 13A, 13B, and 13C are schematic diagrams of an adjustable annuloplasty ring 100 according to another embodiment. In this embodiment, the annuloplasty ring 100 includes arm extensions or "horns" 1310, 1312 attached to each end of the magnet housing 1104. The horns 1310, 1312 may include a suitable rigid or semi-rigid material such as metal or plastic. The horns 1310, 1312 redirect or angle a wire 1314 forming the loop of the annuloplasty ring 100. For example, the horns 1310, 1312 may redirect the wire 1314 approximately 90° from the cylindrical axis of the magnet 1102 within the housing 1104. Thus, the horns 1310, 1312 further maintain the "D" shape of the annuloplasty ring 100 such that it is substantially only adjusted in the AP direction (e.g., expansion/contraction of the loop is perpendicular to the rotation of the magnet 1102). In one embodiment, the annuloplasty ring 100 includes silicone tubing 1317 sealed to each horn 1310, 1312. The wire 1314 extends through the silicone tubing 1317. The silicone tubing 1317 stretches and contracts to accommodate circumferential changes to the loop in the annuloplasty ring 100.

FIG. 13B is a cross-sectional view of the housing 1104 shown in FIG. 13A according to one embodiment. In this embodiment, the magnet 1102 includes a first threaded insert 1318 and a second threaded insert 1320. The two inserts 1318, 1320 have opposite threaded orientations. For example, the first threaded insert 1318 may have a right-hand thread orientation and the second threaded insert 1320 may have a left-hand thread orientation. Both ends of the magnet 1102 may be coupled to bearings 1116 to support the spinning magnet 1102. Each end of the wire 1314 is threaded to interface with its respective threaded insert 1318, 1320 such that rotating the magnet 1102 in one direction pulls the ends of the wire 1314 toward each other and the center of the magnet, and rotating the magnet in the opposite direction pushes the ends of the wire 1314 away from each other and the center of the magnet 1102.

As also shown in FIG. 13B, the housing 1104 and horns 1310, 1312 are sealed from the outside environment. The housing 1104 may include two portions that are welded together along a weld line 1321. Further, the horns 1310, 1312 are bonded to the housing 1104 to create a hermetic seal 1322. Lubricant 1324 may also be sealed within portions of the housing 1104 to provide for proper operation of the bearings 1116.

FIG. 13C is a cross-sectional view of the interface between the horn 1310 and the silicone tubing 1317 according to one embodiment. As shown, in certain embodiments, the annuloplasty ring 100 may include a Dacron® covering 1326 (or other polyester covering) or a covering of other suitable material. The inner pathway of the horn 1310 may include a lubricant such as polytetrafluoroethylene (as known as PTFE Teflon®), silicone oil, grease, etc. to reduce friction between the wire 1314 and the horn 1310 during adjustment of the annuloplasty ring 100. The silicone tubing 1317 attaches to the horn 1310 and may provide an area into which sutures may be placed to secure the annuloplasty ring 100 to heart tissue. As discussed above, the silicone tubing 1317 also provides elasticity to accommodate expansion and contraction of the annuloplasty ring 100.

Figure 14A:
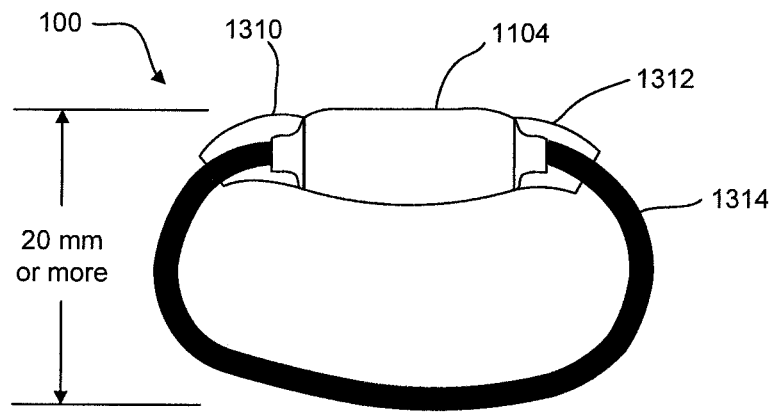
FIGS. 14A and 14B schematically illustrate one embodiment in which the superelasticity of a wire may be compressed so as to allow an annuloplasty ring to be inserted through a trocar.
Figure 14B:
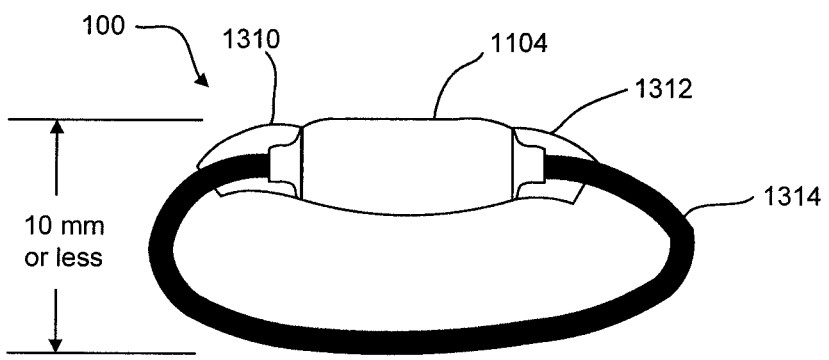

In certain embodiments, the annuloplasty ring 100 is configured for implantation into a heart through a narrow trocar or similar device. For example, FIGS. 14A and 14B schematically illustrate one embodiment in which the superelasticity of the wire 1314 (e.g., including a material such as nitinol), may be compressed so as to allow the annuloplasty ring 100 to be inserted through a trocar. In FIG. 14A, the size of the annuloplasty ring 100 in the AP dimension is approximately 20 mm or more according to some embodiments. This size may correspond to the dimensions of the annuloplasty ring 100 both before and after being inserted through the trocar. In FIG. 14B, the annuloplasty ring 100 is compressed so as to pass through the trocar. In this configuration, the size of the annuloplasty ring 100 in the AP dimension is approximately 10 mm or less according to some embodiments. The superelasticity of the wire 1314 allows for extreme flexibility, yet still provides the necessary strength after implantation for annuloplasty.

Figure 15A:
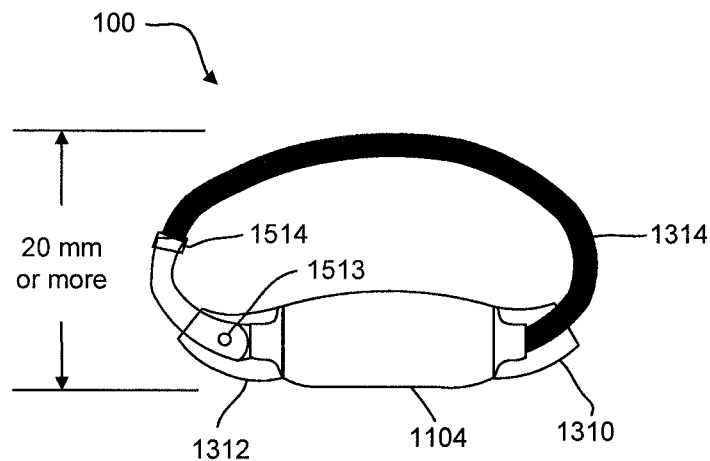
FIGS. 15A and 15B schematically illustrate an annuloplasty ring having a hinged arm according to one embodiment.
Figure 15B:
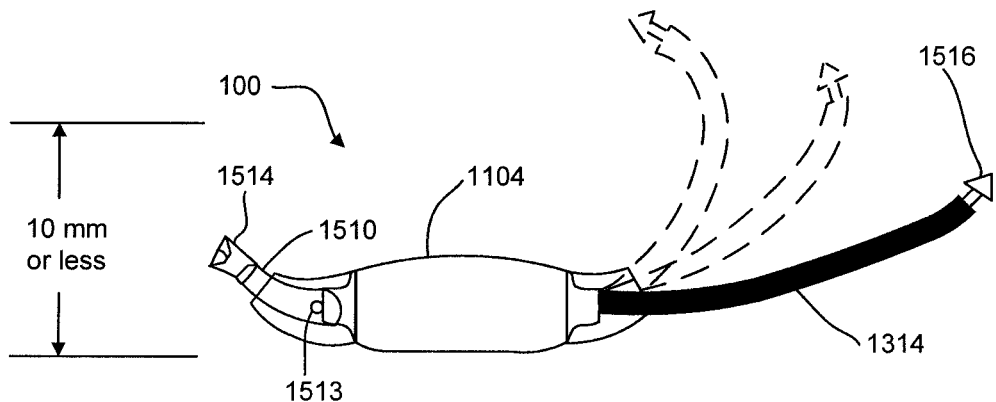

Other embodiments also allow for the annuloplasty ring 100 to be inserted through a trocar. For example, FIGS. 15A and 15B schematically illustrate an annuloplasty ring 100 having a hinged arm 1510 according to one embodiment. The hinged arm 1510 is connected to the housing 1104 through a pin joint 1513. The other end of the hinged arm 1510 includes a latch 1514 for engaging the superelastic wire 1314 after implantation through the trocar. For example, the latch 1514 may include a socket configured to receive a "snap-in" lock pin 1516 attached to the free end of the wire 314 curing implantation. Thus, the annuloplasty ring 100 may be inserted into a very small orifice without worry of damaging the wire 1314.

Figure 16A:
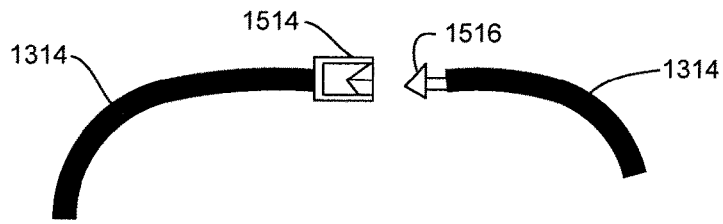
FIGS. 16A, 16B, 16C, 16D, and 16E schematically illustrate alternative latch embodiments that may be used with the annuloplasty ring shown in FIGS. 15A and 15B according to certain embodiments.
Figure 16B:
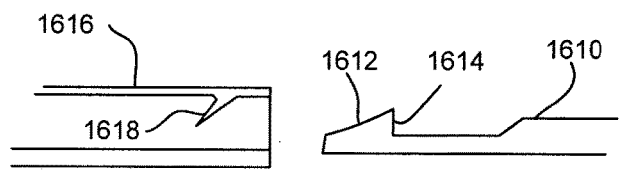
Figure 16C:
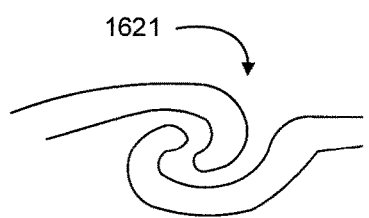
Figure 16D:
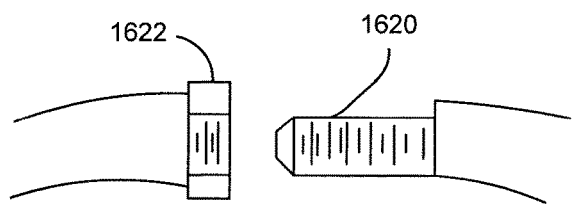
Figure 16E:
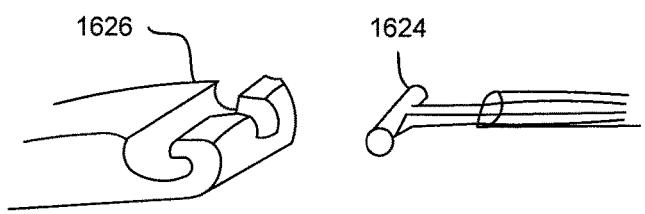

Alternative latch embodiments that may be used with the annuloplasty ring 100 shown in FIGS. 15A and 15B are schematically illustrated in FIGS. 16A, 16B, 16C, 16D, and 16E. FIG. 16A, for example, illustrates an embodiment wherein the socket latch 1514 and the lock pin 1516 are located anywhere along the wire 1314. In other words, the socket latch 1514 is not directly connected to the hinged arm 1510, as shown in FIGS. 15A and 15B. In FIG. 16B, the latching mechanism includes a "ramp and pawl" device in which a pin 1610 having a ramped surface 1612 and a vertical surface 1614 is inserted into a receptacle 1616 having a slanting protrusion 1618. The slanting protrusion 1618 is angled and sufficiently flexible so as to allow the slanted surface 1612 to proceed into the receptacle 1616. However, once inserted, the slanting protrusion 1618 interfaces with the vertical surface 1614 of the pin 1610 so as to prevent the pin 1610 from exiting the receptacle 1616, at least under normal operating conditions. In FIG. 16C, a "knuckle" style latch 1621 provides coupling simile to that used in trains. In FIG. 16D, the latch includes a threaded end 1620 configured to be screwed into a threaded nut 1622. In FIG. 16E, the latch includes a "T-bar" 1624 configured to be received by an appropriately shaped receptacle 1626. An artisan will recognize, of course, that the embodiments shown in FIGS. 16A, 16B, 16C, 16D, and 16E are provided by way of example only, and that many other different types of latches may also be used.

Figure 17A:
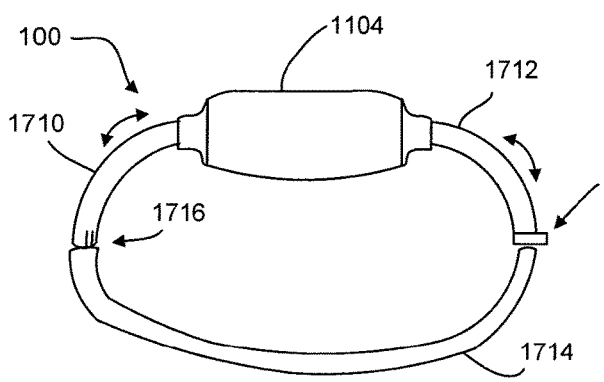
FIGS. 17A, 17B, 17C, 17D, 17E, and 17F are schematic diagrams of an adjustable annuloplasty ring according to another embodiment.
Figure 17B:
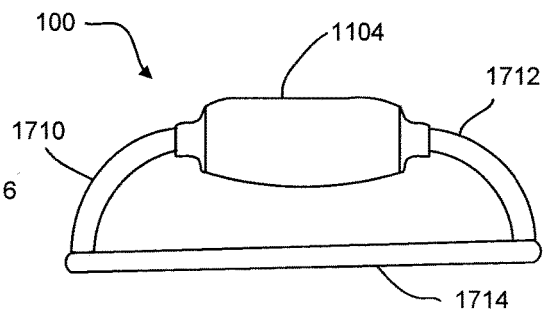
Figure 17C:
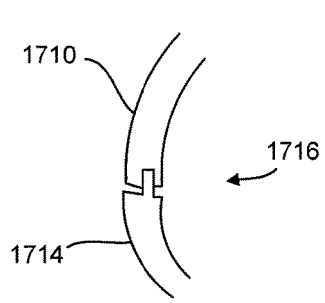
Figure 17D:
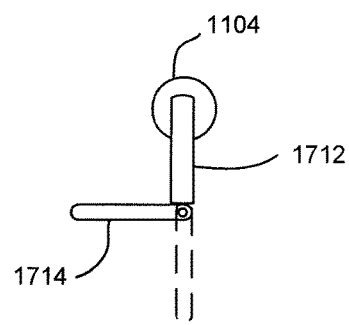
Figures 17E, 17F:
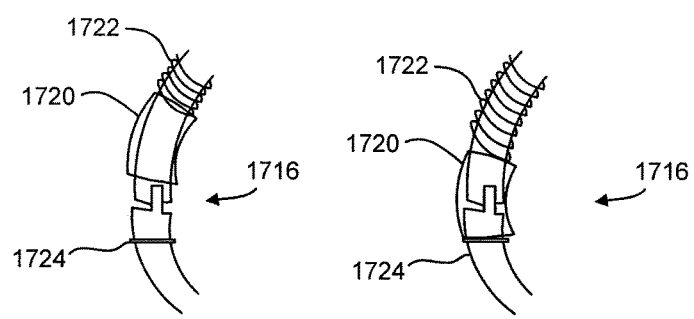

FIGS. 17A, 17B, 17C, 17D, 17E, and 17F are schematic diagrams of adjustable annuloplasty ring 100 according to another embodiment. In this embodiment, the annuloplasty ring 100 includes a first arm 1710 attached to the housing 1104, a second arm 1712 attached to the housing 1104, and a third arm 1714 extending between the first arm 1710 and the second arm 1712. As shown by the curved arrows in FIG. 17A, at least one of the first arm 1710 and the second arm 1712 may be pushed into or out of the housing 1104 in response to the rotation of the internal magnet 108 discussed above. The third arm 1714 is connected to at least one of the first arm 1710 and the second arm 1712 with a folding hinge 1716 that allows the loop portion of the annuloplasty ring 100 to be folded for insertion through a trocar. FIG. 17A illustrates a front view of the "open" or unfolded annuloplasty ring 100. FIG. 17B illustrates a front view of the "folded" annuloplasty ring 100 for insertion through the trocar. FIGS. 17C and 17D provide respective close-up views of the hinge 1716. After inserting the annuloplasty ring 100 through the trocar, the hinges are opened and may be locked in the open position for implantation around a heart valve (e.g., the mitral valve). For example, FIGS. 17E and 17F illustrate a locking mechanism that includes a locking sleeve 1720, a bias element 1722 (e.g., spring), and a mechanical stop 1724. In FIG. 17E, the locking sleeve 1720 is located above the hinge 1716. As the hinge 1716 is opened, the bias element 1722 pushes the locking sleeve 1720 over the hinge 1716 until it makes contact with the stop 1724, as shown in FIG. 17F. Thus, once the hinge 1716 is open, the bias element 1722 and the stop 1724 hold the locking sleeve 1720 in place such that the hinge 1716 cannot be opened, at least not without user intervention.

Figure 18:
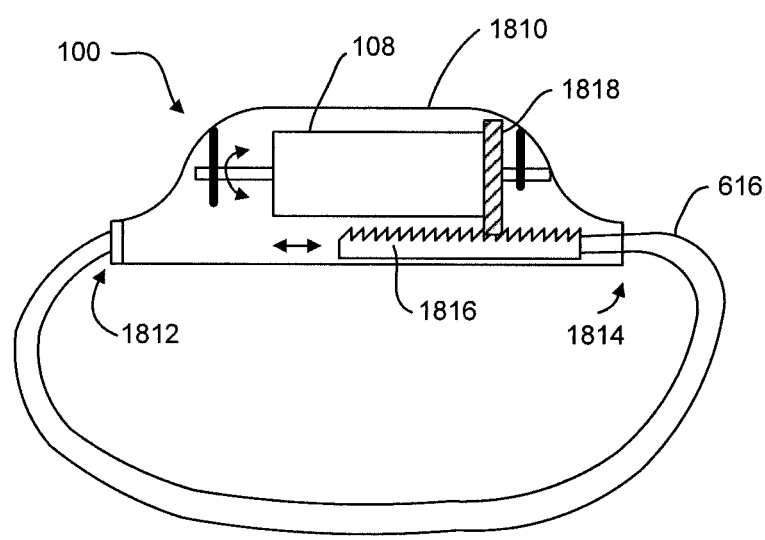
FIG. 18 is a schematic diagram of an adjustable annuloplasty ring according to another embodiment.
Figure 19:
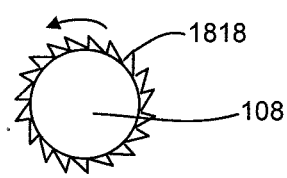
FIG. 19 is a simplified schematic illustrating an end view of a gear attached to a magnetic motor shown in FIG. 18 according to one embodiment.

FIG. 18 is a schematic diagram of an adjustable annuloplasty ring 100 according to another embodiment. In this embodiment, the annuloplasty ring 100 includes a housing 1810, a magnetic motor 108, and a wire 616, such as the magnetic motor 108 and wire 616 discussed above in relation to FIGS. 1B, 2A, 2B, 3, 4, and 6. The wire 616 includes a fixed end 1812 attached to the housing 1810 and a moving end 1814 attached to a rack 1816 located within the housing 1810. In one embodiment, the rack 1816 is cut or formed within the wire 616 itself. The magnetic motor 108 rotates in the presence of a rotating magnetic field so as to turn a gear 1818. The gear 1818 is in mechanical communication with the rack 1816 such that turning the gear 1818 slides the rack 1816 back and forth to change the size of the loop of the annuloplasty ring 100. For illustrative purposes, FIG. 19 is a simplified schematic illustrating an end view of the gear 1818 attached to the magnetic motor 108 according to one embodiment.

Figure 20A:
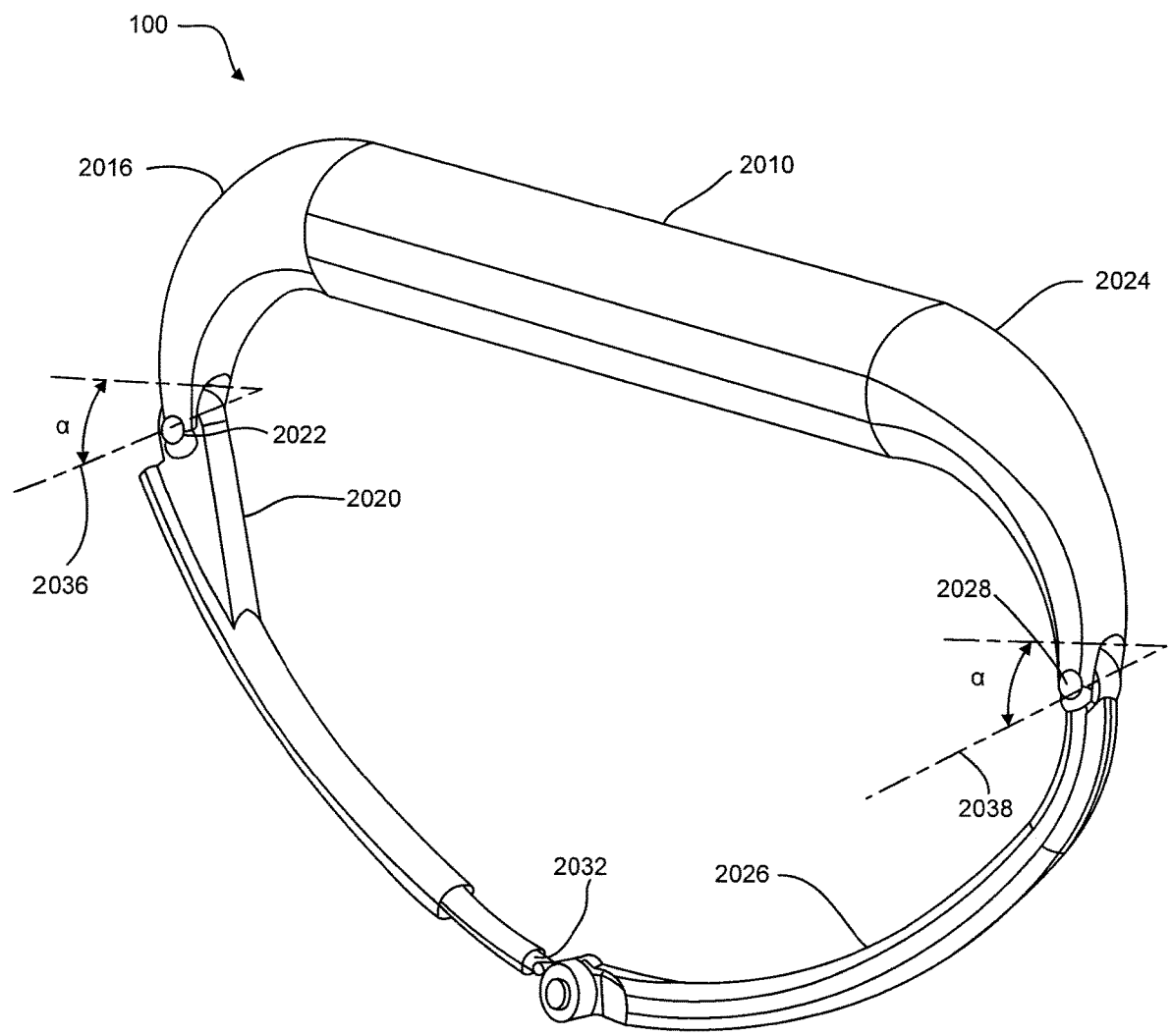
FIGS. 20A and 20B schematically illustrate an annuloplasty ring according to another embodiment.
Figure 20B:
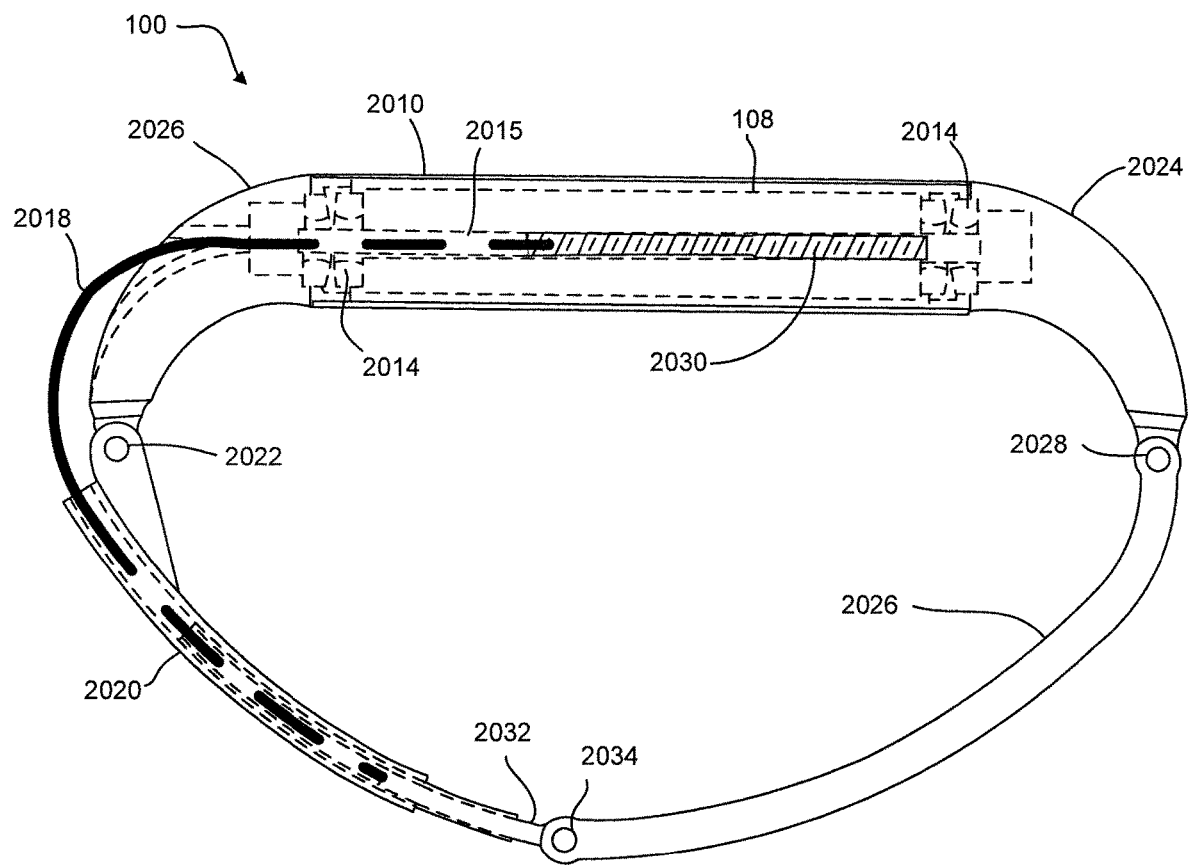

FIGS. 20A and 20B schematically illustrate an annuloplasty ring 100 according to another embodiment. FIG. 20A is a perspective view of the annuloplasty ring 100. FIG. 20B is a partially transparent top view of the annuloplasty ring 100. The annuloplasty ring 100 includes a body tube 2010 for enclosing a magnet 108. The magnet 108 is cylindrical and both ends thereof are coupled to bearings 2014 to allow the magnet 108 to rotate when exposed to a rotating magnetic field. The magnet 108 has magnetic poles divided along a plane that runs along the length of the cylinder. The magnet 108 includes a hollow region 2015 running along the length of the cylinder between the magnetic poles. The hollow region 2015 may be threaded or may include a threaded insert through which a lead screw 2030 is pulled (e.g., right and left as shown in FIG. 20B) through the magnet 108.

A first end of the body tube 2010 is connected to a first fixed arm 2016 and a first end of the lead screw 2030 crimps or otherwise attaches to a first end of a drive cable 2018. The first fixed arm 2016 is connected to a first swivel arm 2020 at a first pin joint 2022. A second end of the body tube 2010 is connected to a second fixed arm 2024 that is connected to a second swivel arm 2026 at a second pin joint 2028. A second end of the drive cable 2018 crimps or otherwise attaches to a push rod 2032. A second end of the push rod 2032 is connected to the second swivel arm 2026 at a third pin joint 2034.

When the magnet 108 is exposed to a rotating magnetic field (e.g., using the external magnetic adjustment device 102), the magnet 108 rotates. The connection of the drive cable 2018 between the lead screw 2030 and the push rod 2032 prevents the lead screw 2030 from rotating along with the magnet 108. Rather, the rotating magnet causes the lead screw 2030 to push and pull the drive cable 2018 into and out of the magnet 108, which causes the swivel arms 2020, 2026 to pivot at their respective pin joints 2022, 2028, 2034 to reduce or enlarge the size of the ring opening in the AP dimension. For example, the first pin joint 2022 may rotate around a first axis 2036 and the second pin joint 2028 may rotate around a second axis 2038 (which is parallel to the first axis 2036) such that the swivel arms 2020, 2026 move in a first plane.

In addition, or in other embodiments, the annuloplasty ring 100 is configured to change shape in a second plane. For example, one or more of the pin joints 2022, 2028, 2034 shown in FIG. 20B may be replaced by ball joints (or pin joints that rotate in a diff rent direction). In such an embodiment, the ball joints may be configured to rotate out of the first plane when the rotating magnet 108 pushes or pulls the drive cable 2018. For example, first joint 2022 and/or the second joint 2028 may rotate at an angle α with respect to the second axis 2038. In one such embodiment, the annuloplasty ring 100 is configured to form a saddle shape when the rotating magnet 108 pushes or pulls the drive cable 2018.

Figure 21:
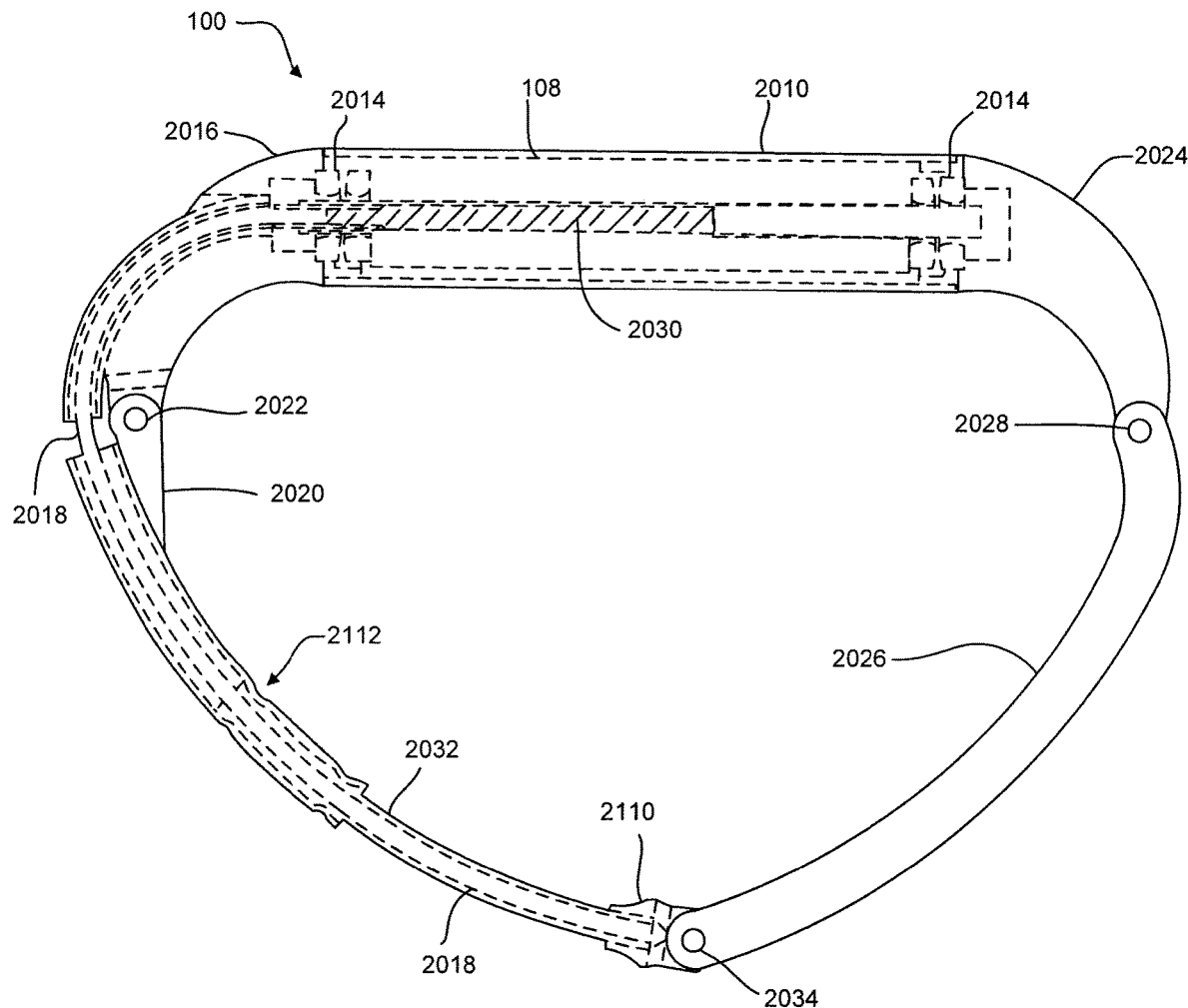
FIG. 21 schematically illustrates an annuloplasty ring according to another embodiment.

FIG. 21 schematically illustrates an annuloplasty ring 100 according to another embodiment. The embodiment illustrated in FIG. 21 is similar to the embodiment shown in FIGS. 20A and 20B, except that the push rod 2032 is hollow to allow the drive cable 2018 to be inserted and secured therein. The annuloplasty ring 100 in FIG. 21 also includes a coupler 2110 to attach the push rod 2032 and/or the drive cable 2018 to the second swivel arm 2026 at the third pin joint 2034. As the rotating magnet 108 pushes and pulls the drive cable 2018, the drive cable 2018 pushes and pulls the push rod 2032 through the first swivel arm 2020, which causes the swivel arms 2020, 2026 to pivot at their respective pin joints 2022, 2028, 2034 to reduce or enlarge the size of the ring opening in the AP dimension. As a safety feature, the first swivel arm 2020 includes one or more divots or crimps 2112 configured to engage the sliding end of the push rod 2032 to prevent it from exiting the second swivel arm 2020.

Figure 22:
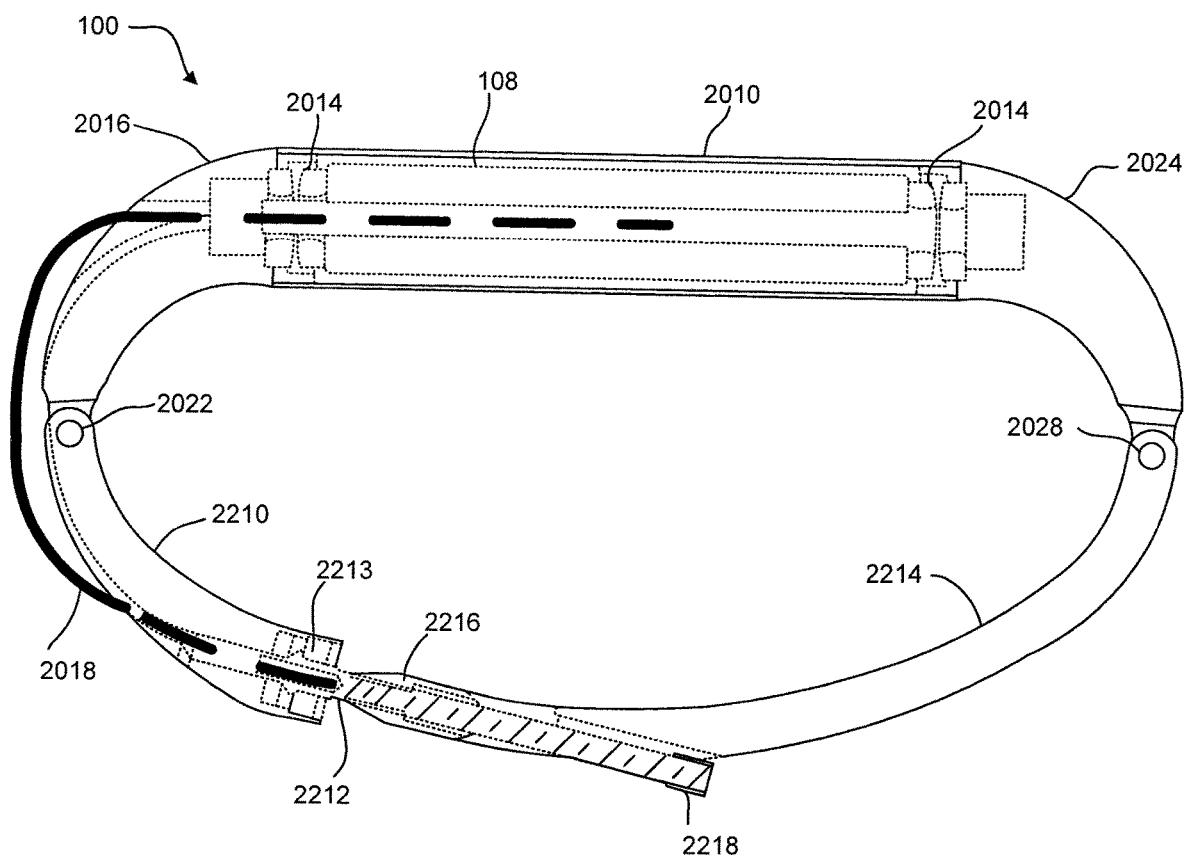
FIG. 22 schematically illustrates an annuloplasty ring according to another embodiment.

FIG. 22 schematically illustrates an annuloplasty ring 100 according to another embodiment. The annuloplasty ring 100 includes the body tube 2010, magnet 108, bearings 2014, first fixed arm 2016, second fixed arm 2024, drive cable 2018, first pin joint 2022, and second pin joint 2028 discussed above in relation to FIGS. 20A and 20B. In this embodiment, however, the magnet 108 need not be threaded, though it may or may not be hollow to facilitate attachment of the drive cable 2018. A first end of the drive cable 2018 is attached to either the magnet 108 such that rotating the magnet 108 causes the drive cable 2018 to rotate.

The annuloplasty ring 100 shown in FIG. 22 includes a first swivel arm 2210 attached to the first fixed arm 2016 at the first pin joint 2022. The first swivel arm 2210 is coupled to a lead screw 2212 using a bearing 2213. A second end of the drive cable 2018 is attached to a first end of the lead screw 2213 such that rotating the drive cable 2018 causes the lead screw 2212 to rotate about the bearing 2213. The bearing 2213 allows the lead screw to rotate freely without detaching from the first swivel arm 2210. A second swivel arm 2214 is attached to the second fixed arm 2024 at the second pin joint 2028. The second swivel arm 2214 includes a threaded drive nut 2216 that engages the threads of the threads of the lead screw 2212. As the lead screw 2212 screws into or out of the drive nut 2216, the swivel arms 2210, 2214 pivot at their respective pin joints 2022, 2028 to reduce or enlarge the size of the ring opening in AP dimension. The lead screw 2212 may include an end stop 2218 to prevent the lead screw 2212 from being removed (e.g., unscrewed) from the drive nut 2216.

Figure 23A:
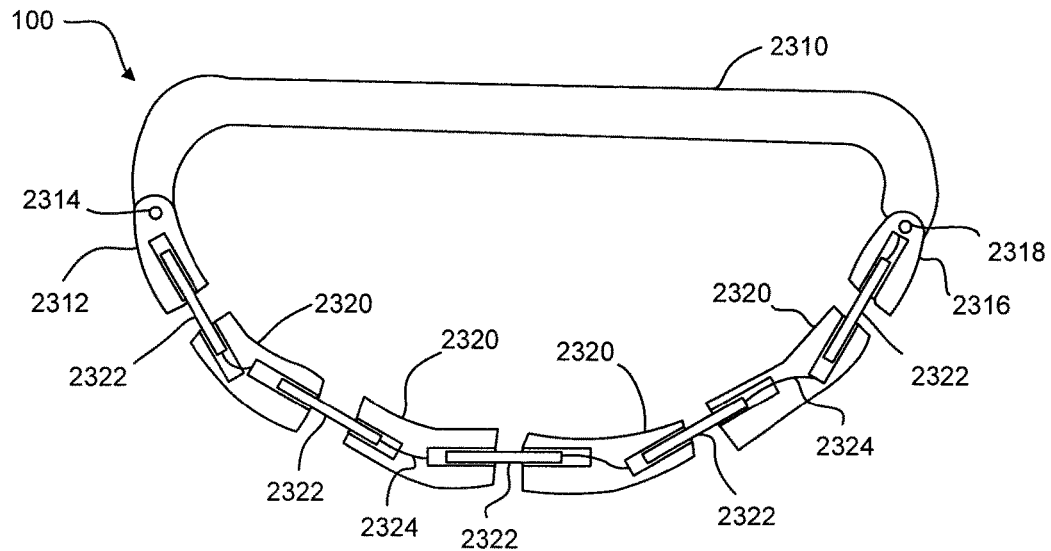
FIGS. 23A, 23B, and 23C schematically illustrate a multi-segment annuloplasty ring according to one embodiment.
Figure 23B:
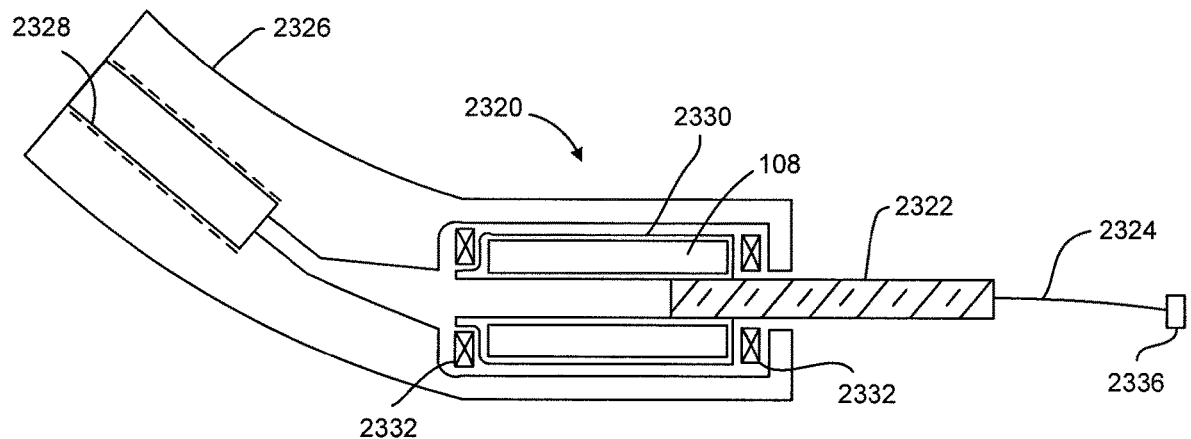
Figure 23C:
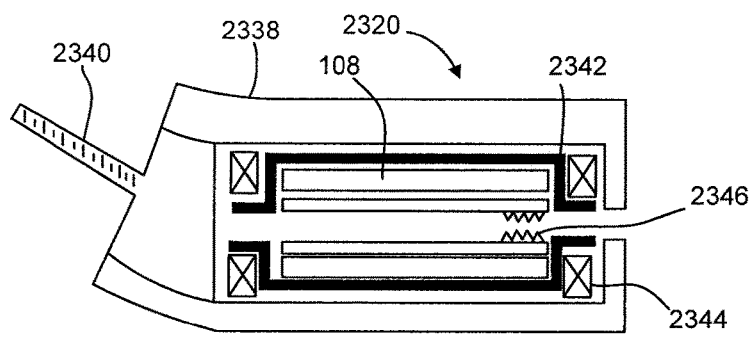

An artisan will recognize that many changes may be made to the annuloplasty ring embodiments disclosed herein. For example, FIGS. 23A, 23B, and 23C illustrate a multi-segment annuloplasty ring 100 according to one embodiment. The annuloplasty ring 100 includes a body tube 2310 attached to a first magnetic drive segment 2312 at a first pin joint 2314 and a second magnetic drive segment 2316 at a second pin joint 2318. The annuloplasty ring 100 may include one or more additional magnetic drive segments 2320 (four shown in the example of FIG. 23A) coupled between the first magnetic drive segment 2312 and the second magnetic drive segment 2316. The magnetic drive segments 2312, 2316, 2320 are coupled to one another with respective lead screws 2322 (five shown in the example of FIG. 23A). Safety wires 2324 (five shown in the example of FIG. 23A) are attached between each lead screw 2322 and a respective magnetic drive segment 2318, 2320. Each magnetic drive segment 2312, 316, 2320 includes a magnet 108 (FIGS. 23B and 23C) that may be rotated using a changing magnetic field to drive the respective lead screws 2322. Thus, the distance between adjacent magnetic drive segments 2312, 2316, 2320 may be selectively adjusted. In one embodiment, the position of each magnetic drive segment 2312, 2316, 2320 may be individually adjusted.

FIG. 23B schematically illustrates an example magnetic drive segment 2320 according to one embodiment. The magnetic drive segment 2320 include a link housing 2326 having a first end with a threaded drive nut 2328 for receiving a first lead screw 2322 (not shown in FIG. 23B). A second end of the link housing 2326 includes a hollow magnet 108 within a magnet housing 2330. The magnet 108 and magnet housing 2332 are attached to bearings 2332 that allow them to rotate in the presence of a rotating magnetic field. A second lead screw 2322 is connected to and rotates with the magnet 108, and is attached to a first end of a safety wire 2324. A second end of the safety wire 2324 is attached to a safety stop 2336 configured to attach to one of the other magnetic drive segments 2312, 2316, 2320 shown in FIG. 23A.

FIG. 23C schematically illustrates an example magnetic drive segment 2320 according to another embodiment. The magnetic drive segment 2320 shown in FIG. 23C includes a link housing 2338 having a first end fixed to a threaded stud 2340. The threaded stud 2340 is configured to be received by one of the other magnetic drive segments 2312, 2316, 2320 shown in FIG. 23A. Thus, in this embodiment, some or all of the separate drive screws 2322 are not used. A second end of the link housing 2338 includes a hollow magnet 108 within a magnet housing 2342. The magnet 108 and magnet housing 2342 are attached to bearings 2344 that allow them to rotate in the presence of a rotating magnetic field. An inner magnet housing 2346 is threaded to receive a lead screw 2322 or a threaded stud fixed to one of the other magnetic drive segments 2312, 2316, 2320 shown in FIG. 23A.

Figure 24:
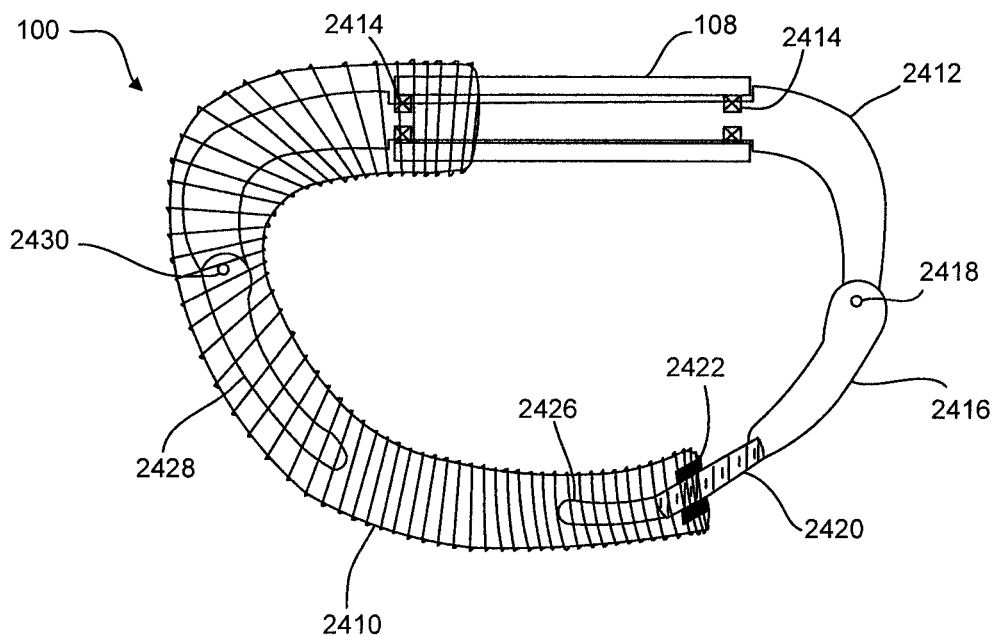
FIG. 24 is a schematic diagram of an annuloplasty ring that includes a bidirectional torsion drive cable according to one embodiment.

FIG. 24 is a schematic diagram of an annuloplasty ring 100 that includes a bidirectional torsion drive cable 2410 according to one embodiment. The annuloplasty ring 100 includes a C-shaped base 2412 that passes through a hollow magnet 108. In the presence of a rotating magnetic field, the hollow magnet 108 rotates on bearings 2414 attached to the base 2412. A first end of the base 2412 is attached to a first swivel arm 2416 at a first pin joint 2418. The first swivel arm 2416 includes a threaded section 2420. A first end of the bidirectional torsion drive cable 2410 is attached to a first end of the magnet 108. A second end of the bidirectional torsion cable 2410 includes a drive nut 2422 that engages the threaded section 2420 of the first swivel arm 2416. In one embodiment, the first swivel arm 2416 includes a curved lead-in section 2426 to assist in controlling the shape of the bidirectional torsion drive cable 2410. In addition, or in other embodiments, the annuloplasty ring 100 may also include a second swivel arm 2428 connected to a second end of the base 2412 at a second pin joint 2430. The second swivel arm 2428 also assists in controlling the shape of the bidirectional torsion drive cable 2410. As the magnet 108 rotates, the drive nut 2422 draws the threaded section 2420 of the first swivel arm 2416 into and out of the bidirectional torsion drive cable 2410 to adjust the size of the annuloplasty ring 100. The bidirectional torsion drive cable 2410 may include, for example, a flexible shaft available from S.S. White Technologies, Inc., of Piscataway, N.J.

Figure 25:
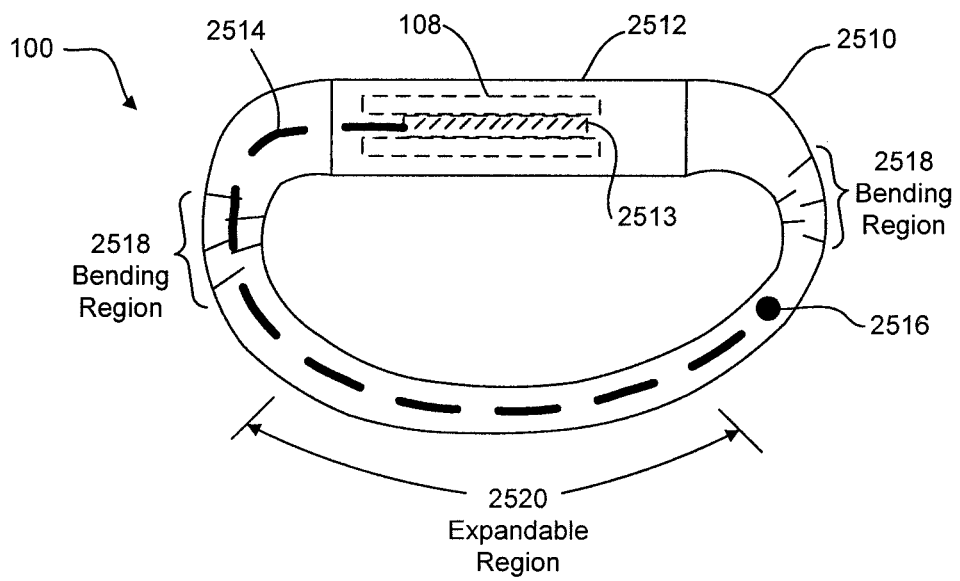
FIG. 25 is a schematic diagram of an annuloplasty ring that includes an elastic tube according to one embodiment.

FIG. 25 is a schematic diagram of an annuloplasty ring 100 that includes an elastic tube 2510 according to one embodiment. The elastic tube 2510 extends between the ends of a rigid base 2512 to form a D-shaped ring. A magnet 108 with internal threads (as discussed above) is configured to rotate within the base 2512 in the presence of a rotating magnetic field. A first end of a drive cable 2514 may be threaded so as to engage the internal threads of the magnet 108. In another embodiment, as shown in FIG. 25, the first end of the drive cable 2514 is attached to a threaded drive screw 2513 configured to engage the internal threads of the magnet 108. A second end of the drive cable 2514 is attached to an anchor point 2516 within the elastic tube 2510. As the magnet 108 rotates, the drive cable 2514 is drawn into and out of the magnet 108. The elastic tube 2510 includes bending regions 2518 and an expandable region 2520. The drive cable 2514 acts as a draw string to control the circumference of the expandable section 2520 of the elastic tube 2510. In one embodiment, the elastic tube 2510 comprises superelastic nitinol.

Figure 26:
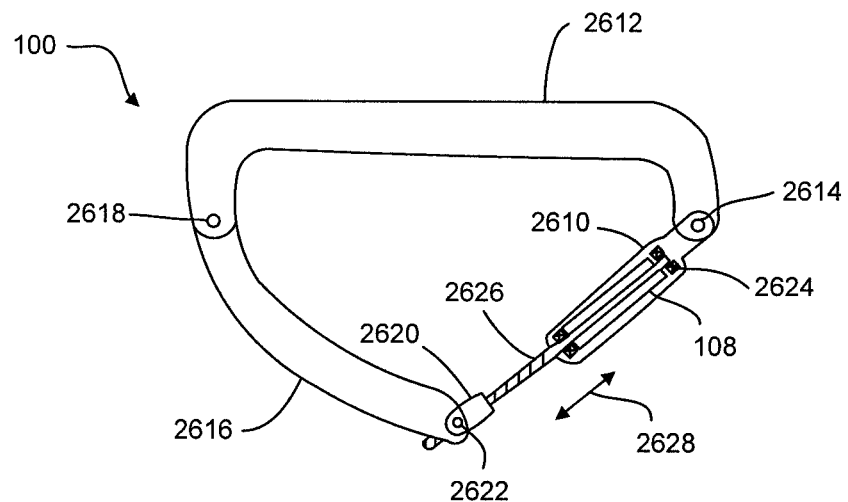
FIG. 26 is a schematic diagram of an annuloplasty ring that includes a rotatable magnet within a pivot arm according to one embodiment.

FIG. 26 is a schematic diagram of an annuloplasty ring 100 that includes a rotatable magnet 108 within a pivot arm 2610 according to one embodiment. The annuloplasty ring 100 includes a C-shaped base 2612 attached to a first end to the pivot arm 2610 at a first pin joint 2614. A second end of the base 2612 is attached to a first end of a second pivot arm 2616 at a second pin joint 2618. A second end of the second pivot arm 2616 is attached to a drive nut 2620 at a third pin joint 2622. As discussed above, the magnet 108 (or an attached magnet housing) may be coupled to bearings 2624 that allow the magnet 108 to rotate within the pivot arm 2610. The magnet 108 (or a magnet housing) is attached to a first end of a lead screw 2626. A second end of the lead screw 2626 interfaces with the drive nut 2620. Thus, as the magnet 108 rotates in the presence of a rotating magnetic field, the lead screw 2626 is drawn into and out of the drive nut 2020 in the direction of the illustrated arrow 2628 to adjust the size of the annuloplasty ring 100.

Figure 27:
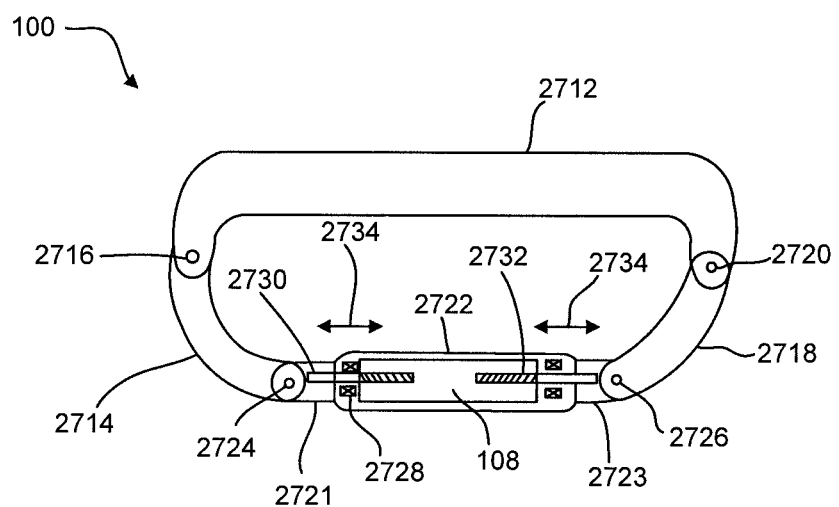
FIG. 27 is a schematic diagram of an annuloplasty ring according to another embodiment.

FIG. 27 is a schematic diagram of an annuloplasty ring 100 according to another embodiment. The annuloplasty ring 100 includes a C-shaped base 2712 having a first end attached to a first end of a first pivot arm 2714 at a first pin joint 2716. A second end of the base 2712 is attached to a first end of a second pivot arm 2718 at a second pin joint 2720. A second end of the first pivot arm 2714 is attached to a first coupler 2721 at a third pin joint 2724. A second end of the second pivot arm 2718 is attached to a second coupler 2723 at a fourth pin joint 2726. A magnet 108 is configured to rotate on bearings 2728 within a drive housing 2722. The first coupler 2721 is attached to a first lead screw 2730 and the second coupler 2723 is attached to a second lead screw 2732. Each lead screw 2730, 2732 is configured to interface with respective internal threads of the magnet 108. The first lead screw 2730 and the second lead screw 2732 are threaded in opposite directions. For example, the first lead screw 2730 may have left-hand threads and the second lead screw 2732 may have right-hand threads. Thus, as the magnet 108 rotates in the presence of a rotating magnetic field, both lead screws 2730, 2732 are either drawn into the magnet 108, or both lead screws 2730, 2732 are drawn out of the magnet 108 in the direction of the illustrated arrows 2734 to adjust the size of the annuloplasty ring 100.

Example External Magnetic Adjustment Device

Figure 28:
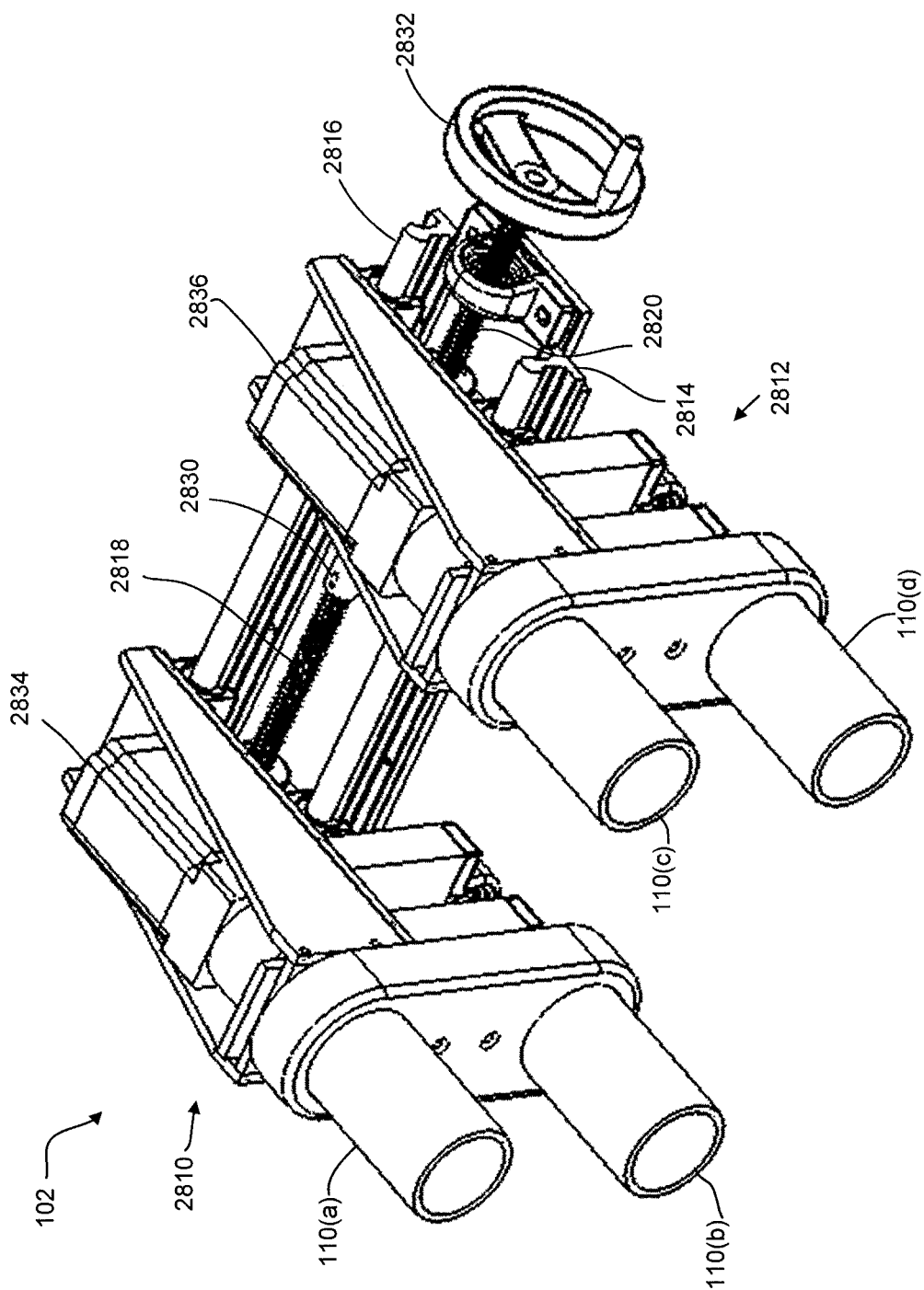
FIG. 28 is a perspective view of an external magnetic adjustment device according to one embodiment.

FIG. 28 is a perspective view of an external magnetic adjustment device 102 according to one embodiment. The external magnetic adjustment device 102 includes a first cylindrical magnet 110(a), a second cylindrical magnet 110(b), a third cylindrical magnet 110(c), and a fourth cylindrical magnet 110(d) (referred to collectively as magnets 110). In one embodiment, the magnets 110 are permanent magnets. In another embodiment, the magnets 110 are electromagnets configured in be selectively activated. The first magnet 110(a) and the second magnet 110(b) are attached to a first arm 2810. The third magnet 110(c) and the fourth magnet 110(d) are attached to a second arm. The first arm 2810 and the second arm 2812 are configured to slide relative to each other in opposite directions along a first rail 2814 and a second rail 2816. Thus, a patient's chest may be placed between the magnets 110 of the first arm 2810 and the second arm 2812 during adjustment of a magnetic annuloplasty ring (such as the annuloplasty rings 100 discussed above) implanted within the patient's heart.

As shown in FIG. 28, the first arm 2810 may be connected to a first screw 2818 threaded in a first direction (e.g., right-hand threads) and the second arm 2812 may be connected to a second screw 2820 threaded in a second direction (e.g., left-hand threads). The first screw 2818 is connected to the second screw 2820 by a coupler 2830 such that both screws 2818, 2820 turn at the same time. A user may turn the screws 2818, 2820 using, for example, a hand crank 2832 to adjust the relative positions of the arms 2810, 2812. In another embodiment, a motor (not shown) under the control of a controller (such as the controller 624 shown in FIG. 6) may be used to turn the screws 2818, 2820.

The first arm 2810 includes a first stepper motor 2834 configured to rotate the first magnet 110(a) and the second magnet 110(b). For example, an axle (not shown) may be connected to the first magnet 110(a) and a coupling such as a drive chain (not shown may couple the first magnet 110(a) to the second magnet 110(b) such that the magnets 110(a), 110(b) rotate together in the same direction. Similarly, the second arm 2812 includes a second stepper motor 2834 configured to rotate the third magnet 110(c) and the fourth magnet 110(d). In other embodiments, additional stepper motors (not shown) may be used to independently rotate each magnet. In yet another embodiment ail of the magnets 110 are coupled to a single stepper motor (not shown). The stepper motors 2834, 2836 may be controlled by a host computer or controller (such as the controller 624 shown in FIG. 6) to coordinate the rotation of the magnets 110 at a desired frequency to generate a changing magnetic field suitable for adjusting the annuloplasty ring 100.

The strength of the magnetic field generated by the magnets 110 in the area between the first arm 2810 and the second arm 2812, and in surrounding areas, is based on the polar alignment (e.g., north and south poles) of each magnet 110. For example, FIGS. 29A, 29B, 29C, and 29D schematically illustrate end views of the magnets 110 of the external magnetic adjustment device 102 shown in FIG. 28 according to certain embodiments. In the illustrated examples, a first magnetic pole (e.g., north) is represented by a white semicircle and a second magnetic pole (e.g. south) is represented by a black semicircle. The illustrated examples also graphically illustrate the resulting magnetic field lines resulting from each polar alignment configuration.

Figure 29B:
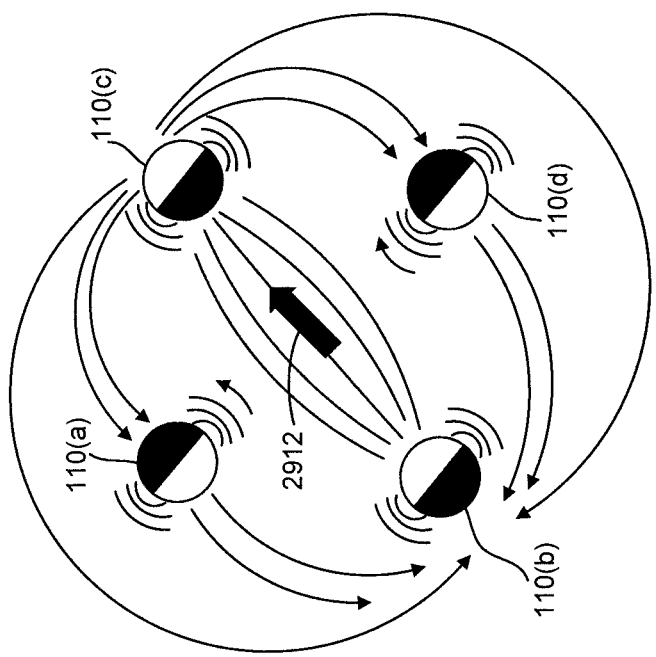
FIGS. 29A, 29B, 29C, and 29D schematically illustrate end views of the magnets of the external magnetic adjustment device shown in FIG. 28 according to certain embodiments.
Figure 29A:
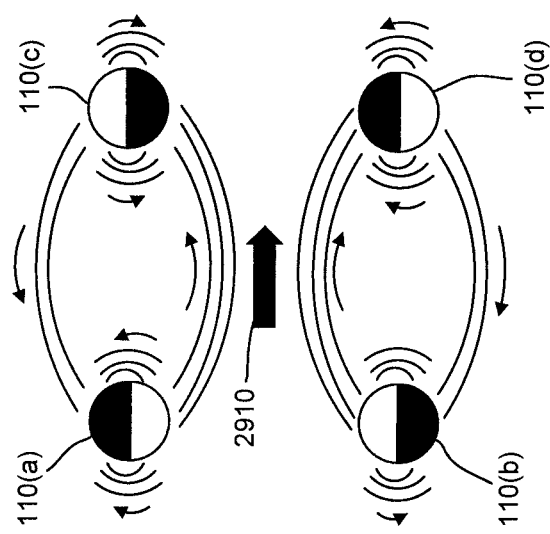

In FIG. 29A, the magnets 110 are in an anti-aligned (Halbach) arrangement with the line separating the magnetic poles in each magnet 110 set at a 0° offset from a horizontal direction. In this arrangement, the magnetic fields from each magnet 110 combine so as to augment the total magnetic field (as illustrated by the arrow 2910) in the central area of the magnet array, while reducing (or not augmenting) the magnetic field in areas outside of the magnet array. Thus, an annuloplasty ring located in the central area of the magnet array may be adjusted in a medical setting (e.g., hospital or physician's office) without the magnetic field altering nearby medical or non-medical devices. When the magnets 110 are rotated in unison, the magnetic field in the central area of the magnet array rotates in the opposite direction. For example, FIG. 29B illustrates the magnets 110 rotated 45° in a clockwise direction as compared to the arrangement of FIG. 29A. Accordingly, the total magnetic field in the central area of the magnet array (as illustrated by the arrow 2912) is also rotated 45°, but in the counterclockwise direction.

Figure 29D:
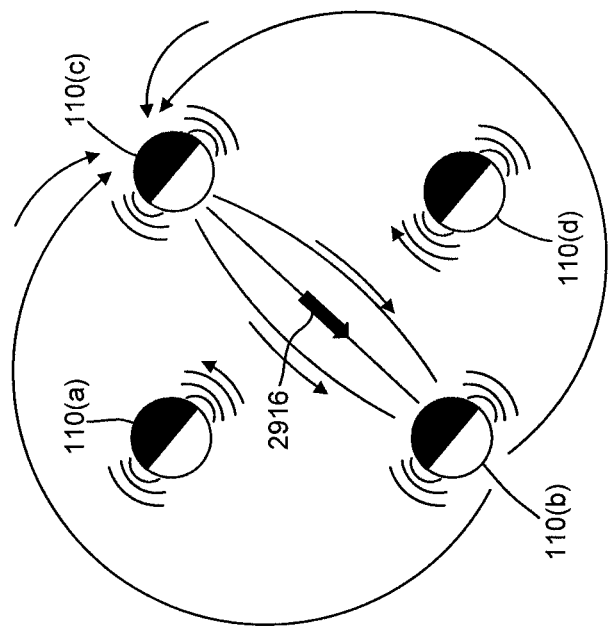
Figure 29C:
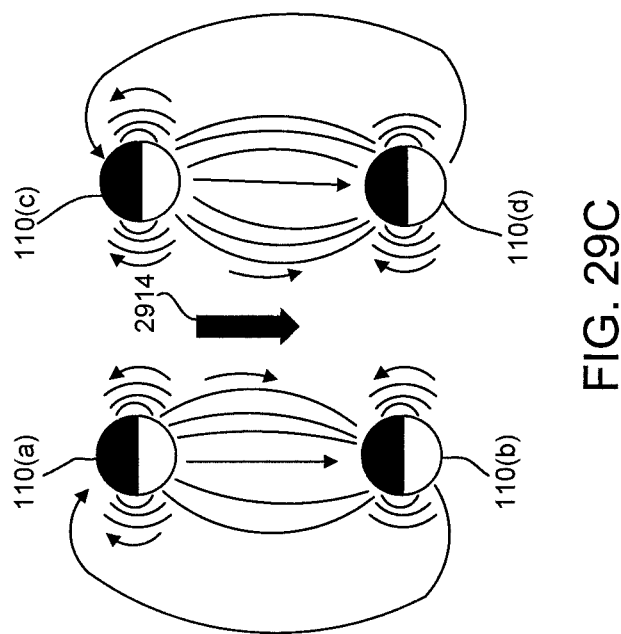

In FIG. 29C, the magnets 110 are in an aligned arrangement such that the magnetic poles are all facing the same direction. Further, the line separating the magnetic poles in each magnet 110 set at a 0° offset from a horizontal direction. In this arrangement, the magnetic fields from each magnet 110 also combine so as to augment the total magnetic field (as illustrated by the arrow 2914) in the central area of the magnet array. However, in some embodiments (see FIG. 30A), the total magnetic field generated in the central region by the aligned arrangement shown in FIG. 29C may not be as great as that of the Halbach arrangement shown in FIG. 29A. Further, the total magnetic field in central region of the magnet array may decrease as the magnets 110 are rotated. For example, FIG. 29D illustrates the magnets 110 rotated 45° in a clockwise direction as compared to the arrangement of FIG. 29C. Accordingly, the total magnetic field in the central area of the magnet array (as illustrated by the arrow 2916) is also rotated 45° in the clockwise direction. However, the magnitude of the total magnetic field in the central region of the magnet array is reduced due to counteracting magnetic fields generated by the first magnet 110(a) and the fourth magnet 110(d).

Figure 30A:
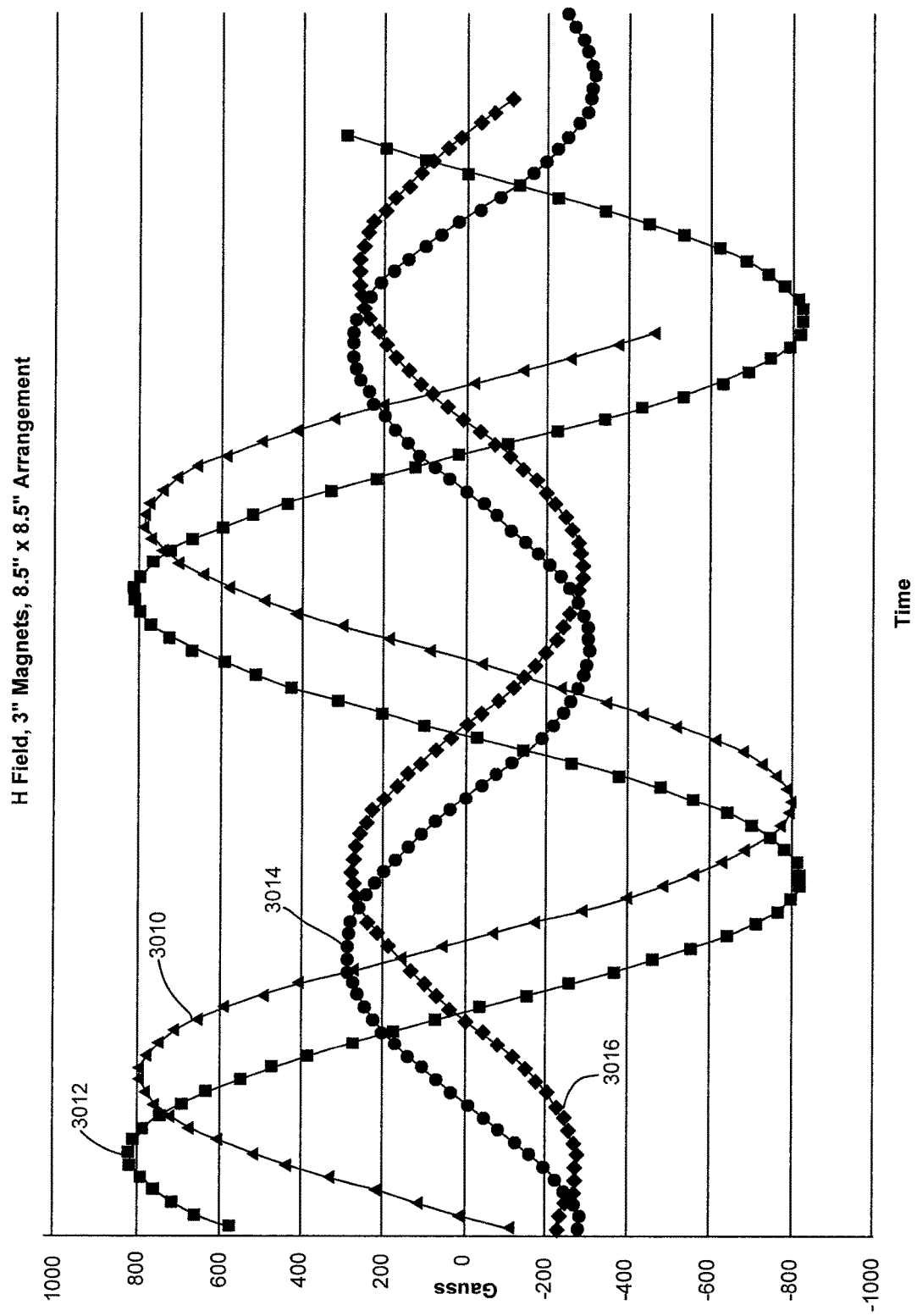
FIGS. 30A and 30B graphically represent example magnetic field measurements as the magnets of the external magnetic adjustment device are rotated according to certain embodiments.
Figure 30B:
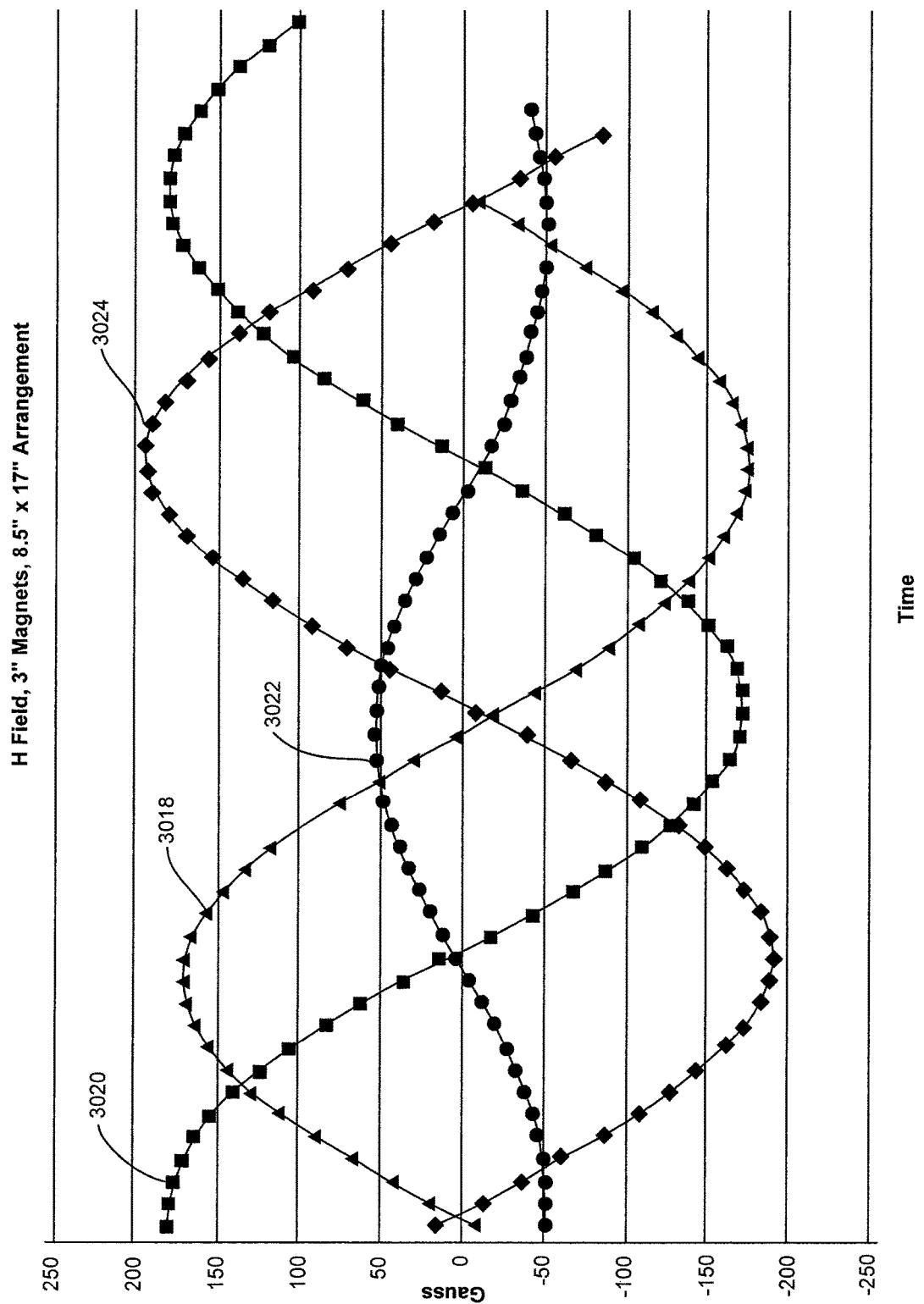

FIGS. 30A and 30B graphically represent example magnetic field measurements as the magnets 110 of the external magnetic adjustment device 102 are rotated according to certain embodiments. FIG. 30A represents data corresponding to aligning 3 inch magnets 110 in a square arrangement that is approximately 8.5 inches×8.5 inches. A first graph 3010 (with data points represented by triangles) corresponds to a Halbach arrangement (see FIGS. 29A and 29B) with a gauss meter aligned at 0° with respect to the horizontal direction. A second graph 3012 (with data points represented by squares) corresponds to the Halbach arrangement (see FIGS. 29A and 29B) with the gauss meter aligned at 45° with respect to the horizontal direction. A third graph 3014 (with data points represented by circles) corresponds to an aligned arrangement (see FIGS. 29C and 29D) with the gauss meter aligned at 0° with respect to the horizontal direction. A fourth graph 3016 (with data points represented by diamonds) corresponds to the aligned arrangement (see FIGS. 29C and 29D) with the gauss meter aligned at 45° with respect to the horizontal direction. As shown in FIG. 30A, the Halbach arrangement provides stronger magnetic fields in the central region of the magnet array, as compared to that of the aligned arrangement.

FIG. 30B represents data corresponding to aligning 3 inch magnets 110 in a rectangular arrangement tats approximately 8.5 inches×17 inches. A first graph 3018 (with data points represented by triangles) corresponds to a Halbach arrangement (see FIGS. 29A and 29B) with a gauss meter aligned at 0° with respect to the horizontal direction. A second graph 3020 (with data points represented by squares) corresponds to the Halbach arrangement (see FIGS. 29A and 29B) with the gauss meter aligned at 90° with respect to the horizontal direction. A third graph 3022 (with data points represented by circles) corresponds to an aligned arrangement (see FIGS. 29C and 29D) with the gauss meter aligned at 0° with respect to the horizontal direction. A fourth graph 3024 (with data points represented by diamonds) corresponds to the aligned arrangement (see FIGS. 29C and 29D) with the gauss meter aligned at 90° with respect to the horizontal direction. As shown in FIG. 30B, the differences between the third graph 3022 and the fourth graph 3024 illustrate that the aligned arrangement does not produce a consistent magnetic field in the central region of the magnet array as the magnets 110 are rotated.

Figure 31:
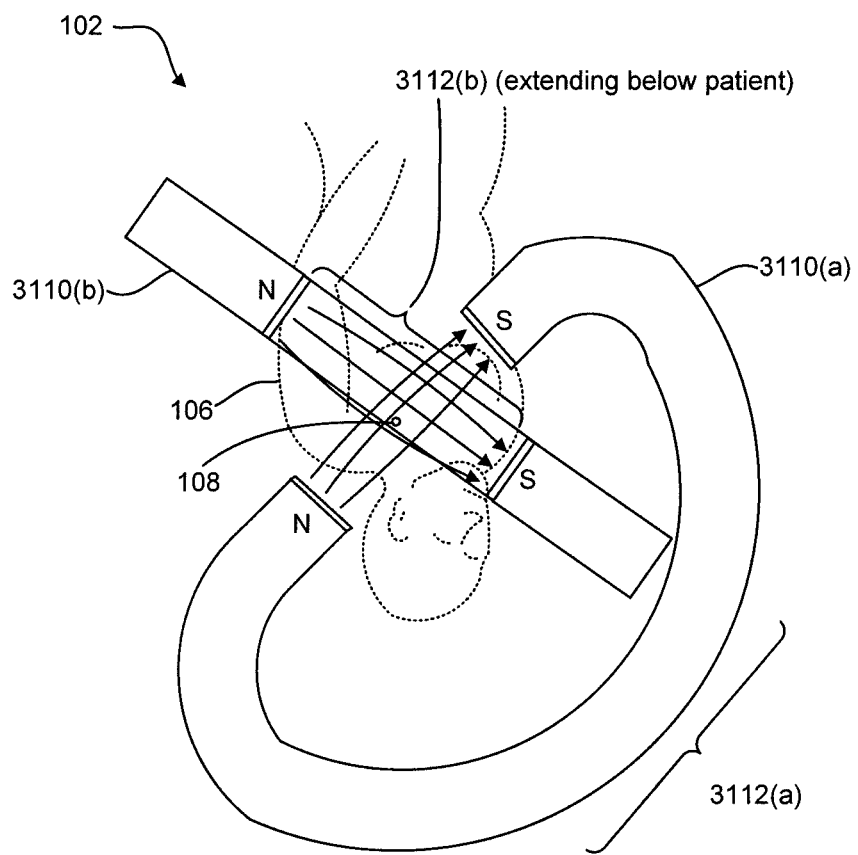
FIG. 31 is a schematic diagram of an external magnetic adjustment device that includes two electromagnets according to one embodiment.

FIG. 31 is a schematic diagram of an external magnetic adjustment device 102 that includes two electromagnets 3110(a), 3110(b) according to one embodiment. Using electromagnets 3110(a), 3110(b) allows the magnetic field generated by the external magnetic adjustment device 102 to be turned off when not in use. Further, in certain embodiments, the electromagnets 3110(a), 3110(b) are driven to provide a constant absolute value for the total magnetic field (as discussed below) as the direction of the total magnetic field is rotated at a selected frequency. In addition, or in other embodiments, the electromagnets 3110(a), 3110(b) may be electronically driven so as to selectively adjust the magnitude of the total magnetic field.

As shown in FIG. 31, the electromagnets 3110(a), 3110(b) according to one embodiment are C-shaped. The C-shape reduces or eliminates the magnitude of the magnetic field outside an area where a patient 106 is being treated. As illustrated by the magnetic field lines in FIG. 31, the magnetic field generated by each electromagnet 3110(a), 3110(b) is fairly well maintained between the opposite ends (e.g., a north "N" end and south "S" end) of the respective electromagnet 3110(a), 3110(b). Although not shown, each electromagnet 3110(a), 311(b) may include, for example, a ferromagnetic core (such as iron) wrapped with an electrically conductive wire. In certain embodiments, the gap between the ends of each C-shaped electromagnet 3110(a), 3110(b) is adjustable. For example, the respective backbones 3112(a), 3112(b) may each include a pivot or slide point.

A first electromagnet 3110(a) is positioned in a horizontal plane and a second electromagnet 3110(b) is positioned in a vertical plane. For example, the "backbone" of the first electromagnet 3110(a) may be in the horizontal plane with a patient table (not shown) and the "backbone" 3112 of the second electromagnet 3112 may pass beneath the patient table. All four magnet ends (two for each magnet 3110(a), 3110(b)) are positioned in the horizontal plane. A patient 106 may be placed on the table in an approximately 30° right-decubitus (right side downward) supine position on the table. In this position, the axis of the magnet 108 in the annuloplasty ring 100 (not shown in FIG. 31) is approximately vertical, and the combined magnetic field is approximately centered around the patient's heart.

Figure 32:
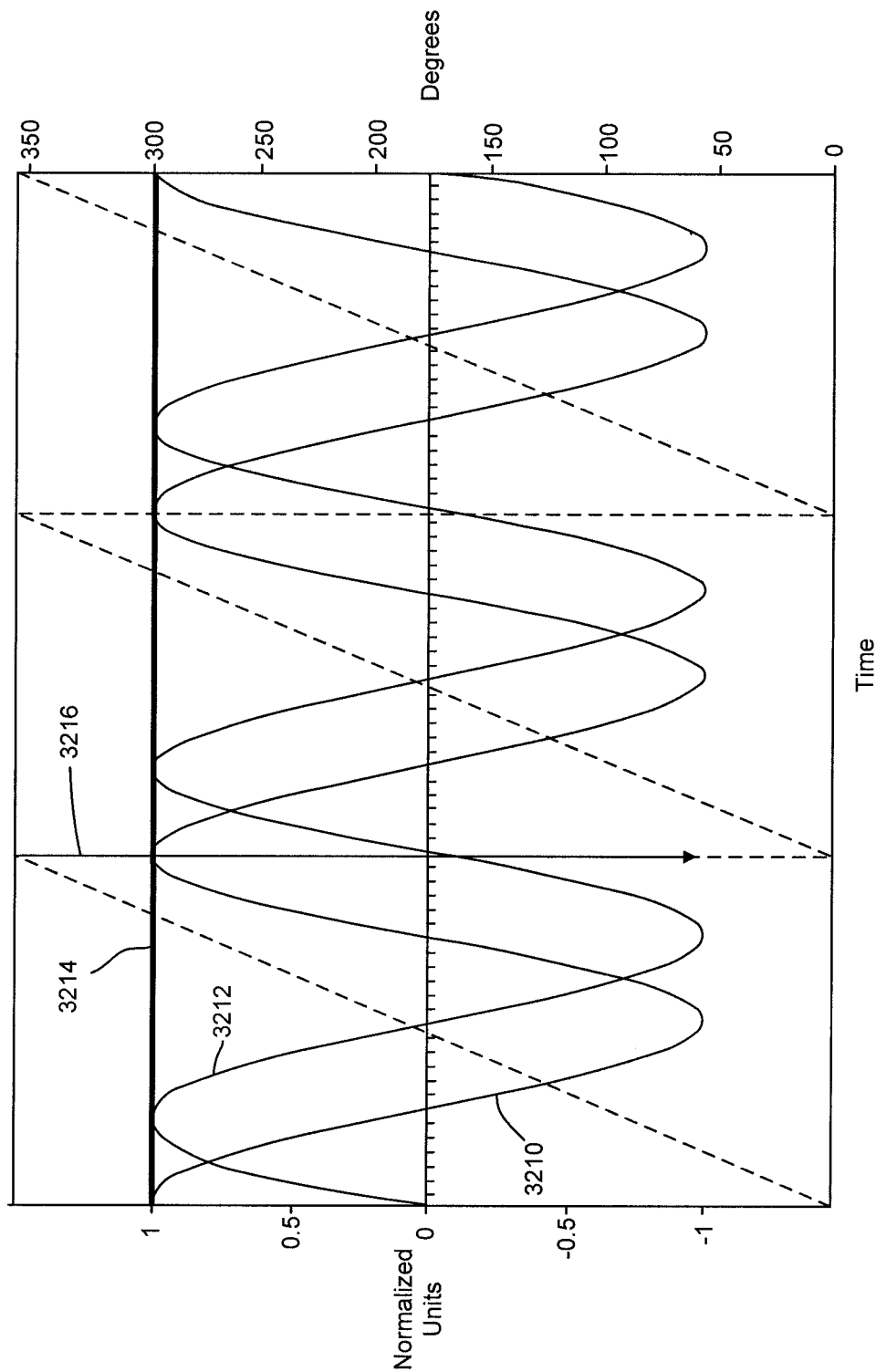
FIG. 32 graphically illustrates various parameters of the magnetic fields generated by the external magnetic adjustment device shown in FIG. 31 according to one embodiment.

FIG. 32 graphically illustrates various parameters of the magnetic fields generated by the external magnetic adjustment device 102 shown in FIG. 31 according to one embodiment. A first graph 3210 illustrates an X-direction component (e.g., that contributed by the magnet 3110(a)) of the combined magnetic field in arbitrary (normalized) units. A second graph 3212 illustrates a Y-direction component (e.g., that contributed by the magnet 3110(b)) of the combined magnetic field in arbitrary (normalized) units. As shown, the first graph 3210 and the second graph 3212 are 90° out of phase from one another. By driving the X and Y-directions of the magnetic fields in this manner, the absolute value of the total field strength of the magnetic field is constant, as illustrated by a third graph 3214. A fourth graph 3216 (shown as a dashed line) illustrates the direction of the total field in degrees. As time progresses, the direction of the total field cycles between 0° and 360° to turn the magnet 108 in the annuloplasty ring 100 implanted within the patient 106.

Example Magnetic Brake Embodiment

Figure 33A:
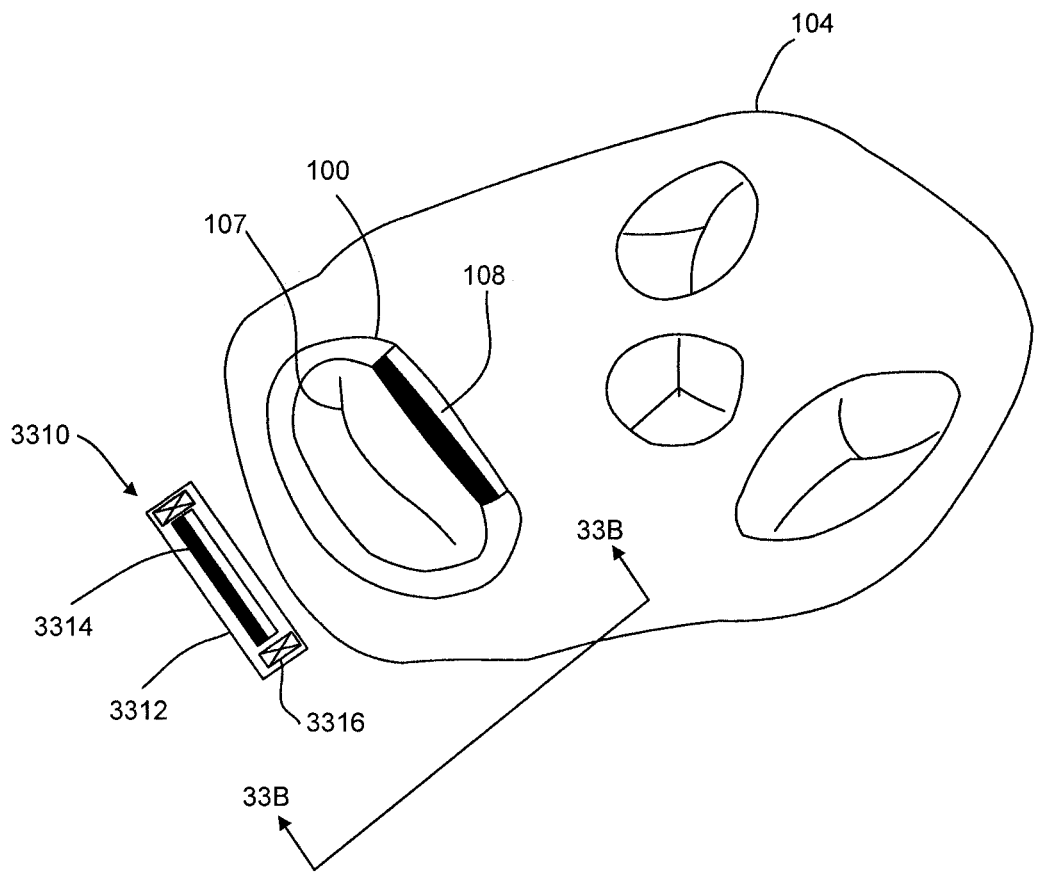
FIG. 33A is a schematic diagram of a superior section view of a heart rating an annuloplasty ring implanted in the heart and a magnetic brake assembly implanted outside of the heart according to one embodiment.

In certain embodiments, vibrations from a patient's beating heart may cause undesirable rotation of the magnet 108 and inadvertent adjustment of the annuloplasty ring 100. Thus, in one embodiment, a magnetic brake is implanted within a patient in an area outside of the patient's heart. For example, FIG. 33A is a schematic diagram of a superior section view of a heart 104 illustrating an annuloplasty ring 100 implanted in the heart 104 and a magnetic brake assembly 3310 implanted outside of the heart 104 according to one embodiment. The annuloplasty ring 100 is attached to or near the mitral valve 107 annulus.

Figure 33B:
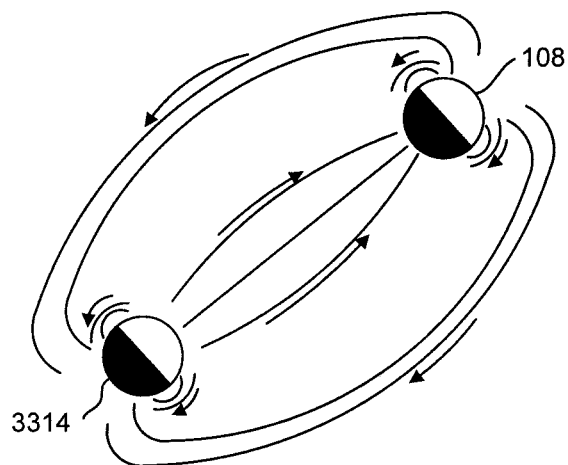
FIG. 33B is a schematic diagram illustrating an end view of a brake magnet and an internal magnet in the annuloplasty ring shown in FIG. 33A according to one embodiment.

The magnetic brake assembly 3310 includes a housing 3312 and a brake magnet 3316 coupled to bearings 3316 in the housing such that the brake magnet 3314 may rotate therein. As discussed above with respect to the internal magnet 108 of the annuloplasty ring 100 and the external magnets 110 of the magnetic adjustment device 102 (shown, e.g., in FIG. 1B, FIG. 3, FIG. 4, FIG. 6, and FIG. 28), the brake magnet 3314 may include a cylindrical magnet having magnetic poles divided along a plane running the length of the cylinder. As shown in FIG. 33B, which is a schematic diagram illustrating an end view of the brake magnet 3314 and the internal magnet 108 in the annuloplasty ring 100 shown in FIG. 33A, the magnetic field of the brake magnet 3314 interacts with the magnetic field of the internal magnet 108 of the annuloplasty ring 100 to prevent rotation of either magnet 3314, 108. Thus, in the absence of the external magnetic field generated by the external adjustment device 102, the internal magnet 108 and the brake magnet 3314 are in "phase lock." The annuloplasty ring 100 may still be adjusted when desired, however, because the external adjustment device 102 generates a sufficiently large rotating magnetic field to overcome the coupling between the internal magnet 108 and the brake magnet 3314.

Figure 34B:
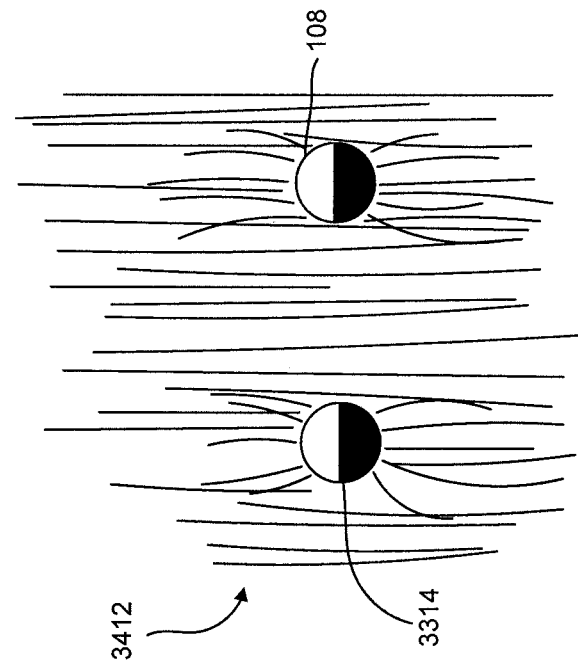
FIGS. 34A and 34B schematically illustrate end views of the brake magnet and the internal magnet of the annuloplasty device according to one embodiment.
Figure 34A:
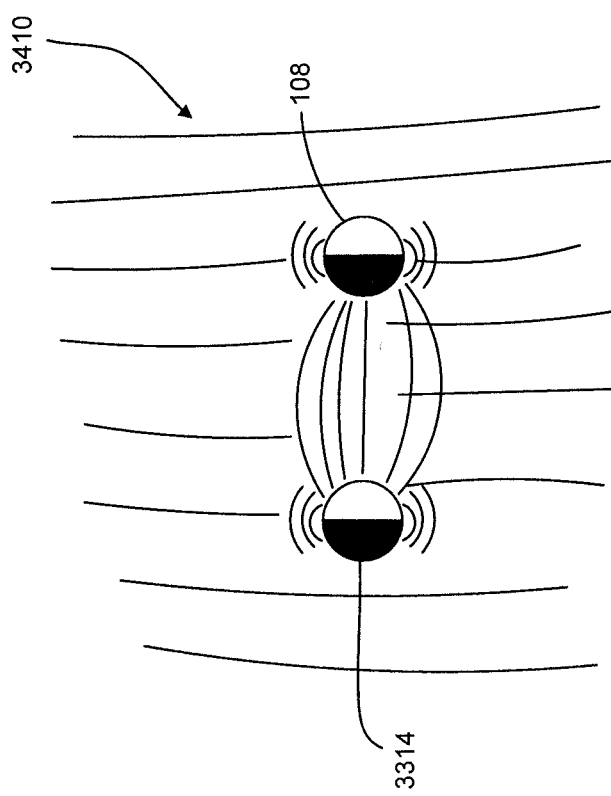

For example, FIGS. 34A and 34B schematically illustrate end views of the brake magnet 3314 and the interne magnet 108 of the annuloplasty device 100 according to one embodiment. In the illustrated examples, a first magnetic pole (e.g., north) is represented by a white semicircle and a second magnetic pole (e.g., south) is represented by a black semicircle. In FIG. 34A, field lines 3410 corresponding to an external magnetic field are represented as having a lower density than field lines 3412 shown in FIG. 34B. Thus, in the example of FIG. 34A the external magnetic field is relatively weak such that the magnetic poles of the magnets 3314, 108 may overcome the magnetic field to align with each other. In the example of FIG. 34A, however, the external adjustment device 102 may be activated to produce a relatively stronger external magnetic field that overcomes the attraction between the magnets 3314, 108. Accordingly, both magnets 3314, 108 align their respective poles with the strong external magnetic field. In other words, both the internal magnet 108 of the annuloplasty ring 100 and the brake magnet 3314 are rotated during selective adjustment of the annuloplasty ring's size.

It will be understood by those having skill in the art that many changes may be made to the details of the above-described embodiments without departing from the underlying principles of the invention. The scope of the present invention should, therefore, be determined only by the following claims.

What is claimed is:

1. A system for treating a heart valve, the system comprising:
    an adjustable annuloplasty ring configured to be attached to or near a cardiac valve annulus, the adjustable annuloplasty ring comprising:
        a tubular body member;
        one or more adjustable members, the tubular body member and the one or more adjustable members forming a ring shape; and
        an internal magnet within the tubular body member, the internal magnet configured to rotate in response to a rotating external magnetic field;
        wherein the internal magnet is coupled to the one or more adjustable members to change a dimension of the ring shape as the internal magnet rotates,
        wherein the adjustable annuloplasty ring is approximately D-shaped as defined by: an anterior/posterior (AP) dimension and a commissure to commissure (CC) dimension, and wherein changing the dimension of the ring shape includes changing the AP dimension of the ring without substantial change to the CC dimension of the ring; and
        wherein the adjustable annuloplasty ring further comprises:
            a magnet housing in the tubular body member; and
            a drive cable connected with the magnet housing, and wherein rotation of the magnet housing turns the drive cable.

2. The system of claim 1, wherein changing the AP dimension of the ring includes symmetrically changing a left side and a right side of the annuloplasty ring.

3. The system of claim 1, wherein the adjustable annuloplasty ring further comprises a drive spindle connected at a first end thereof with the drive cable and connected at a second end thereof with a lead screw, wherein turning the drive cable turns the drive spindle.

4. The system of claim 3, wherein the adjustable annuloplasty ring further comprises:
    a first fixed arm connected with a first end of the tubular body member, and a second fixed arm coupled with a second end of the tubular body member;
    a first swivel arm connected with the first fixed arm and a second swivel arm connected with the second fixed arm;
    a drive nut connected with the second swivel arm and the lead screw; and
    a spindle nut connected with the first swivel arm and the lead screw.

5. The system of claim 4, wherein rotating the lead screw causes the lead screw to rotate into or out of the drive nut, causing the first swivel arm and the second swivel arm to pivot at respective joints to change the AP dimension of the ring.

6. The system of claim 1, wherein the annuloplasty ring is sized to be inserted through a trocar.

7. The system of claim 6, wherein the one or more adjustable members includes a hinged arm including a latch for engaging a superelastic wire after implantation through the trocar.

8. The system of claim 7, wherein the latch includes a socket configured to receive a lock pin attached to a free end of the superelastic wire.

9. A system for changing a dimension of a portion of a subject, the system comprising:
    an adjustable implant configured for implantation within a patient comprising:
        a tubular body member;
        an internal magnet disposed within the tubular body member, the internal magnet configured to rotate in response to a rotating external magnetic field originating external to the subject; and
        an adjustable member operatively coupled to the internal magnet, wherein the internal magnet is configured to rotate in response to the moving magnetic field and change a dimension of the adjustable implant as the internal magnet rotates, and wherein the tubular body member and the adjustable member substantially form an annulus and are configured to be placed around at least the portion of the subject,
        wherein the adjustable annuloplasty implant is approximately D-shaped as defined by: an anterior/posterior (AP) dimension and a commissure to commissure (CC) dimension, and wherein changing the dimension of the adjustable implant shape includes changing the AP dimension of the adjustable implant without substantial change to the CC dimension of the adjustable implant; and
        wherein the adjustable implant is sized to be inserted through a trocar,
        wherein the adjustable implant further comprises:
            a magnet housing in the tubular body member; and
            a drive cable connected with the magnet housing, and
            wherein rotation of the magnet housing turns the drive cable.

10. The system of claim 9, wherein the adjustable implant further comprises a drive spindle connected at a first end thereof with the drive cable and connected at a second end thereof with a lead screw, wherein turning the drive cable turns the drive spindle.

11. The system of claim 10, wherein the adjustable implant further comprises:
    a first fixed arm connected with a first end of the tubular body member, and a
    second fixed arm coupled with a second end of the tubular body member;
    a first swivel arm connected with the first fixed arm and a second swivel arm connected with the second fixed arm;
    a drive nut connected with the second swivel arm and the lead screw; and
    a spindle nut connected with the first swivel arm and the lead screw, wherein rotating the lead screw causes the lead screw to rotate into or out of the drive nut, causing the first swivel arm and the second swivel arm to pivot at respective joints to change the AP dimension of the adjustable implant.

12. The system of claim 9, wherein changing the AP dimension of the adjustable implant includes symmetrically changing a left side and a right side of the annuloplasty adjustable implant.

13. The system of claim 9, wherein the one or more adjustable members includes a hinged arm including a latch for engaging a superelastic wire after implantation through the trocar, and wherein the latch includes a socket configured to receive a lock pin attached to a free end of the superelastic wire.

14. A system for treating a heart valve, the system comprising:
- an adjustable annuloplasty ring configured to be attached to or near a cardiac valve annulus, comprising:
  - a tubular body member;
  - one or more adjustable members, the tubular body member and the one or more adjustable members forming a ring shape;
  - an internal magnet within the tubular body member, the internal magnet configured to rotate in response to a rotating external magnetic field;
  - a first lead screw coupled to a first end of the internal magnet by a first drive cable, wherein rotation of the internal magnet rotates the first drive cable which communicates said rotation to the first lead screw; and
  - a drive nut coupled to the one or more adjustable members, wherein threads of the drive nut engage threads of the first lead screw, and wherein rotation of the first lead screw advances the first lead screw through the drive nut to pull or push the one or more adjustable members changing a dimension of the ring shape,
- wherein the adjustable annuloplasty ring is approximately D-shaped as defined by: an anterior/posterior (AP) dimension and a commissure to commissure (CC) dimension, and wherein changing the dimension of the ring shape includes changing the AP dimension of the ring without substantial change to the CC dimension of the ring.

15. The system of claim 14, wherein changing the AP dimension of the ring includes symmetrically changing a left side and a right side of the annuloplasty ring.

* * * * *